(12) United States Patent
Moinet et al.

(10) Patent No.: US 8,431,556 B2
(45) Date of Patent: Apr. 30, 2013

(54) C-21-KETO LUPANE DERIVATIVES PREPARATION AND USE THEREOF

(75) Inventors: Christophe Moinet, Noyal Chatillon (FR); Marc Courchesne, Laval (CA); Liliane Halab, Laval (CA); Nathalie Chauret, Ile Bizard (CA); Laval Chan Chun Kong, Kirkland (CA)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 288 days.

(21) Appl. No.: 12/830,294

(22) Filed: Jul. 3, 2010

(65) Prior Publication Data

US 2011/0077228 A1    Mar. 31, 2011

Related U.S. Application Data

(63) Continuation of application No. PCT/CA2008/002291, filed on Dec. 23, 2008.

(60) Provisional application No. 61/018,766, filed on Jan. 3, 2008, provisional application No. 61/039,680, filed on Mar. 26, 2008.

(51) Int. Cl.
  *A61K 31/56* (2006.01)
  *C07J 53/00* (2006.01)

(52) U.S. Cl.
  USPC .......................................... 514/177; 552/510

(58) Field of Classification Search ................. 552/510; 514/177
  See application file for complete search history.

*Primary Examiner* — Barbara P Badio
(74) *Attorney, Agent, or Firm* — Daniel A. Pearson

(57) ABSTRACT

The invention relates to 21-keto triterpene compounds of formula (I):
wherein $R^1$, X and Y are as defined herein, and pharmaceutically acceptable salts and solvates thereof. These compounds exhibit significant anti-HIV activity. Thus, the invention also relates to methods for prevention or treatment of HIV infections by administering therapeutically effective amounts of a compound of formula (I), or a pharmaceutically acceptable salt or solvate thereof to a subject in need of such treatment.

21 Claims, No Drawings

C-21-KETO LUPANE DERIVATIVES PREPARATION AND USE THEREOF

The present application is a continuation of International Application No. PCT/CA2008/002291, filed on Dec. 23, 2008, which claims the benefit, under 35 U.S.C. §120, to U.S. Provisional Application Ser. No. 61/018,766, filed Jan. 3, 2008, and to U.S. Provisional Application Ser. No. 61/039,680, filed Mar. 26, 2008, the entire disclosures of each of which are incorporated herein by reference.

Infection by the Human immunodeficiency virus (HIV) can lead to the Acquired ImmunoDeficiency Syndrome (AIDS), an incurable and life threatening condition which requires life-long treatment. It is estimated that the HIV/AIDS pandemic has resulted in the deaths of more than 25 million people since it was first recognized in 1981 and according to a UNAIDS report, an estimated 40 million people worldwide are infected with HIV and about 2.5 million lost their lives to AIDS in 2005. There is presently no effective vaccine for HIV. HIV primarily infects T cells, macrophages and other important components of the immune system resulting in the gradual loss of cell-mediated immunity and as result, HIV patients become increasingly more susceptible to numerous opportunistic infections and tumors and if left untreated, death usually results within 10 years following infection.

The viral life cycle initiates with attachment of HIV gp120 surface protein to the CD4 receptors present of the T-cells. This event triggers a conformational change which exposes an additional binding site on gp120 and results with an interaction with the chemokine co-receptors (CCR5 and CXCR4). Another conformational change arising from co-receptor binding results in fusion of the cellular and viral membranes and release of the virion into the cell. After uncoating and release of the viral genome in the cytoplasm, viral reverse transcriptase (RT) then converts RNA into double stranded DNA which is then integrated into the host genome by the action of HIV integrase. The proviral DNA is then transcribed and translated by host cellular system to express HIV RNA and HIV proteins which are then directed to the cell membrane where they assemble and bud as immature virions. During or soon after the budding process, the viral protease cleaves specific sites in Gag and Gag-Pol releasing essential viral proteins and enzymes such as capsid, nucleocapsid, reverse transcriptase, integrase and spacer peptides SP1 and SP2. This last step is crucial for generating functional viral enzymes and also for the formation of the mature conical HIV capsid.

A number of antiviral agents have been developed to interfere with various stages of viral replication. For example, viral entry can be blocked with T-20 or Maraviroc and post entry steps such as reverse transcription can be blocked with nucleoside RT inhibitors (examples: Lamivudine, Tenofovir, Zidovudine, Didanosine, Emtricitabine, Abacavir) or non-nucleoside RT inhibitors (examples: Nevirapine, Efavirenz and Delavirdine). Integration can be blocked by Raltegravir and HIV proteolytic activity can be inhibited by protease inhibitors such as Saquinavir, Indinavir, Amprenavir, Darunavir, Lopinavir, Atazanavir, and Nelfinavir. Other experimental agents such as Vicriviroc (CCR5), Elvitegravir (integrase), Etravirine (RT), Apricitabine (RT), Bevirimat (maturation) are presently under investigation. The use of combinations of antiretroviral agents have been particularly effective in halting replication to undetectable levels and have led to markedly improved health and life span of HIV/AIDS patients. Nevertheless the appearance of drug resistant viruses after long term therapy is a major concern and there is still a major need for additional drugs in order to provide additional options for these patients facing these issues.

Triterpenoid derivatives have been shown to possess anti-retroviral properties. For example, moronic acid (D. Yu, et al. J. Med. Chem. 2006, 49, 5462-5469), oleanolic acid (H. Assefa, et al. Bioorg. Med. Chem. Lett. 1999, 9, 1889-1894), platanic acid (T. Fujioka, et al. J. Nat. Prod. 1994, 57, 243-247), betulonic acid (O. B. Flekhter, et al. Russ. J. Bioorg. Chem. 2004, 30, 80-88) and betulinic acid (I.-C. Sun, et al. Bioorg. Med. Chem. Lett. 1998, 8, 1267-1272) derivatives are shown to have anti-HIV-1 activities. Other triterpenes arising from the modification of natural product precursors such as betulin have been described, for example 21-keto derivatives shown in references (M. Urban, et al. J. Nat. Prod. 2007, 70, 526-532; M. Urban, et al. Synthesis 2006, 23, 3979-3986; J. Sarek, et al. Bioorg. Med. Chem. Lett. 2005, 15, 4196-4200; J. Sarek, et al. J. Med. Chem. 2003, 46, 5402-5414; M. Hajduch, J. Sarek WO 2001/090046). However, data pertaining to their anti-HIV properties are either absent or are related to uses other than for the treatment of HIV/AIDS conditions. Furthermore, the cytotoxicity of these compounds is unsuitable for the treatment of a chronic disease such as HIV/AIDS.

This invention relates to 21-keto triterpenes and the discovery that these novel modified triterpenoid derivatives possess significant anti-HIV activity.

The present invention relates to a compound of formula (I) and pharmaceutically acceptable salts:

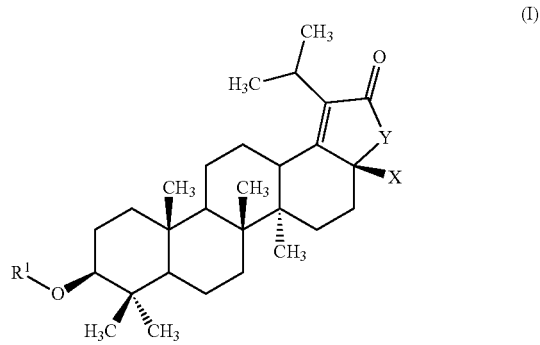

wherein
$R^1$ is H, a hydroxy protecting group or

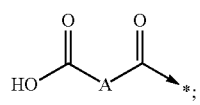

A is $C_{1-8}$ alkyl, $C_{2-8}$ alkenyl, or —$(CH_2)_{1-2}O(CH_2)_{1-2}$—;
Y is C=O or C—$R_{y1}R_{y2}$
$R_{y1}$ and $R_{y2}$ are each independently H or —$CH_3$;
X is

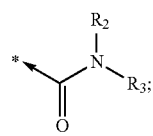

$R_2$ is H, $C_{1-12}$ alkyl which is unsubstituted or substituted one or more times by $R^{10}$, $C_{2-12}$ alkenyl which is unsubstituted or substituted one or more times by $R^{10}$, or $C_{2-12}$ alkynyl which is unsubstituted or substituted one or more times by $R^{10}$;

$R_3$ is H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 member heteroaryl which is unsubstituted or substituted one or more times by $R^{11}$, 6-18 member heteroaralkyl which is unsubstituted or substituted one or more times by $R^{11}$, 3-12 member heterocycle which is unsubstituted or substituted one or more times by $R^{12}$, or 4-18 member heterocycle-alkyl which is unsubstituted or substituted one or more times by $R^{12}$;

$R_2$ and $R_3$ can also be taken together to form 5-12 member heteroaryl which is unsubstituted or substituted one or more times by $R^{11}$, or a 3-12 member heterocycle which is unsubstituted or substituted one or more times by $R^{12}$;

$R^{10}$ is halogen, oxo, $C_{1-6}$ alkoxy, —$NH_2$, —$NH(C_{1-4}$ alkyl), —$N(C_{1-4}$ alkyl)$_2$, —$C(O)NH_2$, —$C(O)NH(C_{1-4}$ alkyl), —$C(O)N(C_{1-4}$ alkyl)$_2$, —NHC(O)H, —$N(C_{1-4}$ alkyl)C(O) H, —$N(C_{1-4}$ alkyl)C(O)$C_{1-4}$ alkyl, —NHC(O)$C_{1-4}$ alkyl, —NHC(O)O$C_{1-4}$ alkyl, —$N(C_{1-4}$ alkyl)C(O)O$C_{1-4}$ alkyl, —NHC(O)$NH_2$, —$N(C_{1-4}$ alkyl)C(O)$NH_2$, —NHC(O) NH$C_{1-4}$ alkyl, —$N(C_{1-4}$ alkyl)C(O)NH$C_{1-4}$ alkyl, —$N(C_{1-4}$ alkyl)C(O)N($C_{1-4}$alkyl)$_2$, —NHC(O)N($C_{1-4}$ alkyl)$_2$, —C(O)H, —C(O)$C_{1-4}$ alkyl, C(O)OH, —C(O) O$C_{1-4}$ alkyl, —OC(O)$C_{1-4}$ alkyl, —OC(O)NH($C_{1-4}$ alkyl), —OC(O)N($C_{1-4}$alkyl)$_2$, —C(NOH)$C_{1-4}$ alkyl, —C(NOH) H, —C(NO$C_{1-4}$ alkyl)$C_{1-4}$ alkyl, —C(NO$C_{1-4}$ alkyl)H, hydroxyl, nitro, azido, cyano, —S(O)$_{0-3}$H, —S(O)$_{0-3}C_{1-4}$ alkyl, —$SO_2NH_2$, —$SO_2NH(C_{1-4}$ alkyl), —$SO_2N(C_{1-4}$ alkyl)$_2$, alkyl)SO$_2C_{1-4}$ alkyl, —NHSO$_2C_{1-4}$ alkyl, —P(O) (OH)$_2$, —P(O)(O$C_{1-4}$alkyl)OH, —P(O)(O$C_{1-4}$alkyl)$_2$, amidino, or guanidino;

$R^{11}$ is halogen, $C_{1-6}$ alkyl, halogenated $C_{1-6}$ alkyl, $C_{2-6}$ alkenyl, $C_{2-6}$ alkynyl, $C_{1-6}$ alkoxy, —$NH_2$, —$NH(C_{1-4}$ alkyl), —$N(C_{1-4}$ alkyl)$_2$, —$C(O)NH_2$, —$C(O)NH(C_{1-4}$ alkyl), —$C(O)N(C_{1-4}$ alkyl)$_2$, —NHC(O)H, —$N(C_{1-4}$ alkyl)C(O) H, —$N(C_{1-4}$ alkyl)C(O)$C_{1-4}$ alkyl, —NHC(O)$C_{1-4}$ alkyl, —NHC(O)O$C_{1-4}$ alkyl, —NHC(O)O$C_{1-4}$ alkyl, —$N(C_{1-4}$ alkyl)C(O)O$C_{1-4}$ alkyl, —NHC(O)$NH_2$, —$N(C_{1-4}$ alkyl)C (O)$NH_2$, —NHC(O)NH$C_{1-4}$ alkyl, —$N(C_{1-4}$ alkyl)C(O) NH$C_{1-4}$ alkyl, —$N(C_{1-4}$ alkyl)C(O)N($C_{1-4}$ alkyl)$_2$, —NHC (O)N($C_{1-4}$ alkyl)$_2$, —C(O)H, —C(O)$C_{1-4}$ alkyl, C(O)OH, —C(O)O$C_{1-4}$ alkyl, —OC(O)$C_{1-4}$ alkyl, —OC(O)NH ($C_{1-4}$ alkyl), —OC(O)N($C_{1-4}$ alkyl)$_2$, —C(NOH)$C_{1-4}$ alkyl, —C(NOH)H, —C(NO$C_{1-4}$ alkyl)$C_{1-4}$ alkyl, —C(NO$C_{1-4}$ alkyl)H, hydroxyl, nitro, azido, cyano, —S(O)$_{0-3}$H, —S(O)$_{0-3}C_{1-4}$ alkyl, —$SO_2NH_2$, —$SO_2NH$ ($C_{1-4}$ alkyl), —$SO_2N(C_{1-4}$ alkyl)$_2$, —$N(C_{1-4}$ alkyl) SO$_2C_{1-4}$alkyl, —NHSO$_2C_{1-4}$ alkyl, —P(O)(OH)$_2$, —P(O) (O$C_{1-4}$alkyl)OH, —P(O)(O$C_{1-4}$alkyl)$_2$, amidino, or guanidino; and $R^{12}$ is halogen, oxo, $C_{1-6}$ alkyl, halogenated $C_{1-6}$ alkyl, $C_{2-6}$ alkenyl, $C_{2-6}$ alkynyl, $C_{1-6}$ alkoxy, —$NH_2$, —$NH(C_{1-4}$ alkyl), —$N(C_{1-4}$ alkyl)$_2$, —$C(O)NH_2$, —$C(O)NH(C_{1-4}$ alkyl), —$C(O)N(C_{1-4}$ alkyl)$_2$, —NHC(O)H, —$N(C_{1-4}$ alkyl)C(O)H, —$N(C_{1-4}$ alkyl)C(O)$C_{1-4}$ alkyl, —NHC(O) $C_{1-4}$ alkyl, —NHC(O)O$C_{1-4}$ alkyl, —$N(C_{1-4}$ alkyl)C(O) O$C_{1-4}$ alkyl, —NHC(O)$NH_2$, —$N(C_{1-4}$ alkyl)C(O)$NH_2$, —NHC(O)NH$C_{1-4}$ alkyl, —$N(C_{1-4}$ alkyl)C(O)NH$C_{1-4}$ alkyl, —$N(C_{1-4}$ alkyl)C(O)N($C_{1-4}$ alkyl)$_2$, —NHC(O)N ($C_{1-4}$ alkyl)$_2$, —C(O)H, —C(O)$C_{1-4}$ alkyl, C(O)OH, —C(O)O$C_{1-4}$ alkyl, —OC(O)$C_{1-4}$ alkyl, —OC(O)NH ($C_{1-4}$ alkyl), —OC(O)N($C_{1-4}$ alkyl)$_2$, —C(NOH)$C_{1-4}$ alkyl, —C(NOH)H, —C(NO$C_{1-4}$ alkyl)$C_{1-4}$ alkyl, —C(NO$C_{1-4}$ alkyl)H, hydroxyl, nitro, azido, cyano, —S(O)$_{0-3}$H, —S(O)$_{0-3}C_{1-4}$ alkyl, —$SO_2NH_2$, —$SO_2NH$ ($C_{1-4}$ alkyl), —$SO_2N(C_{1-4}$ alkyl)$_2$, —$N(C_{1-4}$ alkyl) SO$_2C_{1-4}$alkyl, —NHSO$_2C_{1-4}$ alkyl, —P(O)(OH)$_2$, —P(O) (O$C_{1-4}$alkyl)OH, —P(O)(O$C_{1-4}$alkyl)$_2$, amidino, or guanidino.

In further embodiments, the compounds of the inventions are represented by formula (I) wherein the following embodiments are present alone or in combination:

Y is C═O
Y is C—$R_{y1}R_{y2}$ and $R_{y1}$ and $R_{y2}$ are —$CH_3$
Y is C—$R_{y1}R_{y2}$ and $R_{y1}$ and $R_{y2}$ are H.
Y is —$CH_2$
$R_1$ is

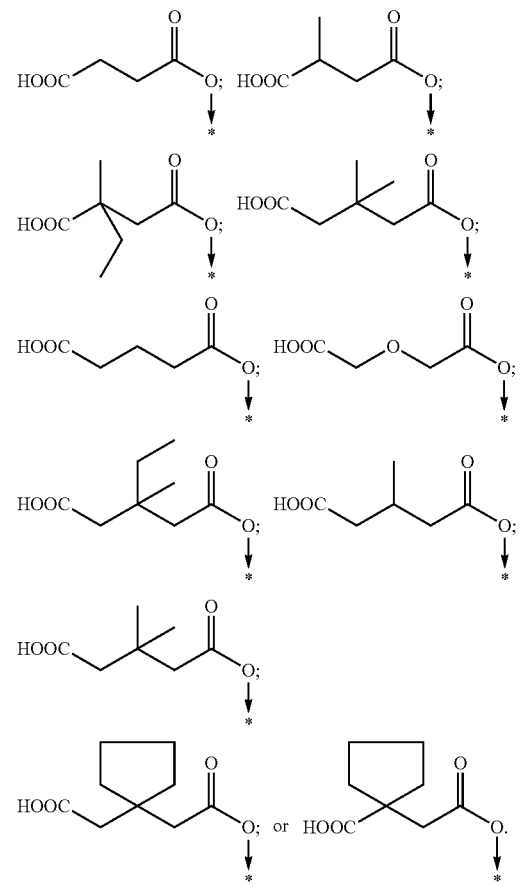

$R_1$ is succinyl, glutaryl, 3'-methylglutaryl, 3'-methylsuccinyl, 3',3'-dimethylsuccinyl, 3',3'-dimethylglutaryl, 2',2'-dimethylmalonyl, 2',3'-dihydroxysuccinyl 2',3'-dimethylsuccinyl, 2',2',3',3'-tetramethylsuccinyl, 2'-methylsuccinyl, or 2',2'-dimethylsuccinyl.

$R_1$ is succinyl, glutaryl, 3'-methylglutaryl, 3'-methylsuccinyl, 3',3'-dimethylsuccinyl, 3',3'-dimethylglutaryl, 2',2'-dimethylmalonyl, 2',3'-dihydroxysuccinyl, 2',2',3',3'-tetramethylsuccinyl or 2',2'-dimethylsuccinyl.

$R_1$ is 3',3'-dimethylsuccinyl.

In a further embodiment, $R_1$ is H, or a hydroxy protecting group.

In a further embodiment, $R_1$ is H.

$R_2$ is H or $C_{1-12}$ alkyl which is unsubstituted or substituted one or more times by $R^{10}$.

$R_2$ is H or $C_{1-6}$ alkyl which is unsubstituted or substituted one or more times by $R^{10}$.

$R_2$ is H, methyl, ethyl, propyl, isopropyl, butyl, sec-butyl, tert-butyl, cyclopropyl, cyclobutyl, cyclopentyl, or cyclohexyl.

$R_2$ is methyl, ethyl, propyl, isopropyl, butyl, sec-butyl, or tert-butyl.

$R_2$ is methyl.

$R_2$ is H.

$R_2$ and $R_3$ taken together form a 5-6 member heteroaryl which is unsubstituted or substituted one or more times by $R^{11}$ or a 5-6 member heterocycle which is unsubstituted or substituted one or more times by $R^{12}$.

$R_2$ and $R_3$ taken together form a piperidyl, a piperazinyl, or a morpholinyl which is unsubstituted or substituted one or more times by $R^{11}$.

$R_2$ and $R_3$ taken together form a diazabicyclo[3.2.1]octane which is unsubstituted or substituted one or more times by $R^{11}$.

$R_3$ is $C_{1-12}$ alkyl which is unsubstituted or substituted one or more times by $R^{10}$, $C_6$ aryl which is unsubstituted or substituted one or more times by $R^{11}$, $C_{7-9}$ aralkyl which is unsubstituted or substituted one or more times by $R^{11}$, 5-6 member heteroaryl which is unsubstituted or substituted one or more times by $R^{11}$, 7-8 member heteroaralkyl which is unsubstituted or substituted one or more times by $R^{11}$, 5-6 member heterocycle which is unsubstituted or substituted one or more times by $R^{12}$, or 7-8 member heterocycle-alkyl which is unsubstituted or substituted one or more times by $R^{12}$.

$R_3$ is $C_{1-6}$ alkyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 member heteroaryl which is unsubstituted or substituted one or more times by $R^{11}$, 7-8 member heteroaralkyl which is unsubstituted or substituted one or more times by $R^{11}$, 5-6 member heterocycle which is unsubstituted or substituted one or more times by $R^{12}$, or 7-8 member heterocycle-alkyl which is unsubstituted or substituted one or more times by $R^{12}$.

$R_3$ is $C_{1-6}$ alkyl which is unsubstituted or substituted one or more times by $R^{10}$, benzyl which is unsubstituted or substituted one or more times by $R^{11}$, 7-8 member heteroaralkyl which is unsubstituted or substituted one or more times by $R^{11}$, 5-6 member heterocycle which is unsubstituted or substituted one or more times by $R^{12}$, or 7-8 member heterocycle-alkyl which is unsubstituted or substituted one or more times by $R^{12}$.

$R_3$ is $C_{1-6}$ alkyl which is unsubstituted or substituted one or more times by $R^{10}$, benzyl which is unsubstituted or substituted one or more times by $R_{11}$, 7-8 member heteroaralkyl which is unsubstituted or substituted one or more times by $R^{11}$, or 7-8 member heterocycle-alkyl which is unsubstituted or substituted one or more times by $R^{12}$.

$R_3$ is $C_{1-6}$ alkyl which is unsubstituted or substituted one or more times by $R^{10}$, benzyl which is unsubstituted or substituted one or more times by $R^{11}$, or 7-8 member heterocycle-alkyl which is unsubstituted or substituted one or more times by $R^{12}$.

$R_3$ is $C_{1-6}$ alkyl which is unsubstituted or substituted one or more times by $R^{10}$.

$R_3$ is 5-6 member heteroaryl which is unsubstituted or substituted one or more times by $R^{11}$.

$R_3$ is 5-6 member heterocycle which is unsubstituted or substituted one or more times by $R^{12}$.

$R_3$ is 7-8 member heterocycle-alkyl which is unsubstituted or substituted one or more times by $R^{12}$.

$R_3$ is methyl, ethyl, propyl, isopropyl, butyl, sec-butyl, tert-butyl, cyclopropyl, cyclobutyl, cyclopentyl, cyclohexyl or cyclohexyl($CH_2$)—.

$R_3$ is benzyl which is unsubstituted or substituted one or more times by $R^{11}$.

$R_3$ is benzyl.

$R_3$ is pyridinyl($CH_2$)— which is unsubstituted or substituted one or more times by $R^{11}$.

$R_3$ is pyridinyl($CH_2$)—.

$R_3$ is ethyl, iso-propyl, tert-butyl, cyclopentyl, cyclopentyl($CH_2$)—, cyclohexyl, cyclohexyl($CH_2$)—, phenyl, benzyl, pyridinyl, pyridinyl($CH_2$)—, piperidynyl, piperazinyl, thiophenyl, morpholino, oxadiazole, pyrimidinyl, pyranyl, pyrazinyl, thiazole, and pyrazole, which are unsubstituted or substituted by one or more substituents chosen from a halogen, $C_{1-4}$ alkyl, $C_{1-4}$ alkyloxy, $CF_3$, $COC_{1-4}$ alkyl, COOH, $COOC_{1-4}$ alkyl, cyano, $NH_2$, nitro, NH($C_{1-6}$ alkyl), and N($C_{1-6}$ alkyl)$_2$.

$R_3$ is piperidinyl which is unsubstituted or substituted one or more times by $R^{12}$.

$R_3$ is piperidinyl.

$R_3$ is pyrimidinyl which is unsubstituted or substituted one or more times by $R^{11}$.

$R_3$ is pyrimidinyl.

$R_3$ is pyridine which is unsubstituted or substituted one or more times by $R^{11}$.

$R_3$ is pyridine.

$R_3$ is pyrazole which is unsubstituted or substituted one or more times by $R^{11}$.

$R_3$ is methyl pyrazole $R_3$ is pyperazinyl.

$R_3$ is phenyl which is unsubstituted or substituted one or more times by $R^{11}$.

$R_3$ is fluorophenyl.

$R_3$ is phenyl.

$R_3$ is cyclohexyl($CH_2$)— which is unsubstituted or substituted one or more times by $R^{10}$.

$R_3$ is cyclohexyl($CH_2$)— which is unsubstituted or substituted one or more times by halogen.

$R^{10}$ is halogen, oxo, $C_{1-6}$ alkoxy, —$NH_2$, —NH($C_{1-4}$ alkyl), —N($C_{1-4}$alkyl)$_2$, —$CONH_2$, —CONH($C_{1-4}$ alkyl), —CON($C_{1-4}$ alkyl)$_2$, —NHCOH, —N($C_{1-4}$ alkyl)COH, —N($C_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —N($C_{1-4}$ alkyl)CONHC$_{1-4}$ alkyl, —N($C_{1-4}$ alkyl)CON($C_{1-4}$ alkyl)$_2$, —NHCON($C_{1-4}$ alkyl)$_2$, —C(O)H, —C(O)$C_{1-4}$ alkyl, carboxy, —C(O)O$C_{1-4}$ alkyl, —C(NOH)$C_{1-4}$ alkyl, —C(NOH)H, —C(NO$C_{1-4}$ alkyl)$C_{1-4}$ alkyl, —C(NO$C_{1-4}$ alkyl)H, hydroxyl, nitro, azido, cyano, —S(O)$_{0-2}$H, —S(O)$_{0-2}C_{1-4}$ alkyl, —$SO_2NH_2$, —$SO_2$NH($C_{1-4}$ alkyl), —$SO_2$N($C_{1-4}$ alkyl)$_2$, —N($C_{1-4}$ alkyl)$SO_2C_{1-4}$ alkyl, —NHSO$_2C_{1-4}$ alkyl, —P(O)(OH)$_2$ or P(O)(O$C_{1-4}$alkyl)$_2$;

$R^{10}$ is halogen, oxo, $C_{1-6}$ alkoxy, —$NH_2$, —NH($C_{1-4}$ alkyl), —N($C_{1-4}$ alkyl)$_2$, —$CONH_2$, —CONH($C_{1-4}$ alkyl), —CON($C_{1-4}$ alkyl)$_2$, —NHCOH, —N($C_{1-4}$ alkyl)COH, —N($C_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —N($C_{1-4}$alkyl)CONHC$_{1-4}$ alkyl, —N($C_{1-4}$ alkyl)CON($C_{1-4}$ alkyl)$_2$, —NHCON($C_{1-4}$ alkyl)$_2$, —C(O)H, —C(O)$C_{1-4}$ alkyl, carboxy, —C(O)O$C_{1-4}$ alkyl, —C(NOH)$C_{1-4}$ alkyl, —C(NOH)H, hydroxyl, nitro, azido, cyano, —S(O)$_{0-2}$H, —S(O)$_{0-2}C_{1-4}$ alkyl, —$SO_2NH_2$, —$SO_2$NH($C_{1-4}$ alkyl), —$SO_2$N($C_{1-4}$ alkyl)$_2$, —N($C_{1-4}$ alkyl)$SO_2C_{1-4}$ alkyl, —NHSO$_2C_{1-4}$ alkyl, or —P(O)(OH)$_2$.

$R^{10}$ is halogen, oxo, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)C$_{1-4}$ alkyl, carboxy, —C(O)OC$_{1-4}$ alkyl, hydroxyl, C$_{1-4}$ alkoxy, nitro, nitroso, azido, or cyano.

$R^{10}$ is halogen, oxo, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)C$_{1-4}$ alkyl, carboxy, —C(O)OC$_{1-4}$ alkyl, hydroxyl, C$_{1-4}$ alkoxy, nitro, azido, or cyano.

$R^{10}$ is halogen, oxo, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)C$_{1-4}$ alkyl, carboxy, —C(O)OC$_{1-4}$ alkyl, hydroxyl, or C$_{1-4}$ alkoxy.

$R^{10}$ is halogen, oxo, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —N(C$_{1-4}$ alkyl)COC$_{1-4}$ alkyl, —NHCOC$_{1-4}$ alkyl, carboxy, —C(O)OC$_{1-4}$ alkyl, hydroxyl, C$_{1-4}$ alkoxy, or cyano.

$R^{11}$ is halogen, C$_{1-6}$ alkyl, halogenated C$_{1-6}$ alkyl, C$_{2-6}$ alkenyl, C$_{2-6}$ alkynyl, C$_{1-6}$ alkoxy, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —N(C$_{1-4}$ alkyl)CONHC$_{1-4}$ alkyl, —N(C$_{1-4}$ alkyl)CON(C$_{1-4}$ alkyl)$_2$, —NHCON(C$_{1-4}$ alkyl)$_2$, —C(O)H, —C(O)C$_{1-4}$ alkyl, carboxy, —C(O)OC$_{1-4}$ alkyl, —C(NOH)C$_{1-4}$ alkyl, —C(NOH)H, —C(NOC$_{1-4}$ alkyl)C$_{1-4}$ alkyl, —C(NOC$_{1-4}$ alkyl)H, hydroxyl, nitro, azido, cyano, —S(O)$_{0-2}$H, —S(O)$_{0-2}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, —P(O)(OH)$_2$ or P(O)(OC$_{1-4}$alkyl)$_2$; and $R^{11}$ is halogen, C$_{1-6}$ alkyl, halogenated C$_{1-6}$ alkyl, C$_{2-6}$ alkenyl, C$_{2-6}$ alkynyl, C$_{1-6}$ alkoxy, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$, alkyl, —NHCOC$_{1-4}$ alkyl, —NHCOOC$_{1-4}$ alkyl, —NHCONHC$_{1-4}$ alkyl, —N(C$_{1-4}$ alkyl)CONHC$_{1-4}$ alkyl, —N(C$_{1-4}$ alkyl)CON(C$_{1-4}$ alkyl)$_2$, —NHCON(C$_{1-4}$ alkyl)$_2$, —C(O)H, —C(O)C$_{1-4}$ alkyl, carboxy, —C(O)OC$_{1-4}$ alkyl, —C(NOH)C$_{1-4}$ alkyl, —C(NOH)H, hydroxyl, nitro, azido, cyano, —S(O)$_{0-2}$H, —S(O)$_{0-2}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, or —P(O)(OH)$_2$.

$R^{11}$ is halogen, C$_{1-6}$ alkyl, halogenated C$_{1-6}$ alkyl, C$_{2-6}$ alkenyl, C$_{2-6}$ alkynyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)C$_{1-4}$ alkyl, carboxy, —C(O)OC$_{1-4}$ alkyl, hydroxyl, C$_{1-6}$ alkoxy, nitro, nitroso, azido, or cyano.

$R^{11}$ is halogen, C$_{1-6}$ alkyl, halogenated C$_{1-6}$ alkyl, C$_{2-6}$ alkenyl, C$_{2-6}$ alkynyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)C$_{1-4}$ alkyl, carboxy, —C(O)OC$_{1-4}$ alkyl, hydroxyl, C$_{1-6}$ alkoxy, nitro, azido, or cyano.

$R^{11}$ is halogen, C$_{1-6}$ alkyl, halogenated C$_{1-6}$ alkyl, C$_{2-6}$ alkenyl, C$_{2-6}$ alkynyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)C$_{1-4}$ alkyl, carboxy, —C(O)OC$_{1-4}$ alkyl, hydroxyl, or C$_{1-6}$ alkoxy.

$R^{11}$ is halogen, C$_{1-6}$ alkyl, halogenated C$_{1-6}$ alkyl, C$_{2-6}$ alkenyl, C$_{2-6}$ alkynyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —N(C$_{1-4}$ alkyl)COC$_{1-4}$ alkyl, —NHCOC$_{1-4}$ alkyl, carboxy, —C(O)OC$_{1-4}$ alkyl, hydroxyl, or C$_{1-6}$ alkoxy.

$R^{12}$ is halogen, oxo, C$_{1-6}$ alkyl, halogenated C$_{1-6}$ alkyl, C$_{2-6}$ alkenyl, C$_{2-6}$ alkynyl, C$_{1-6}$ alkoxy, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —N(C$_{1-4}$ alkyl)CONHC$_{1-4}$ alkyl, —N(C$_{1-4}$ alkyl)CON(C$_{1-4}$ alkyl)$_2$, —NHCON(C$_{1-4}$ alkyl)$_2$, —C(O)H, —C(O)C$_{1-4}$ alkyl, carboxy, —C(O)OC$_{1-4}$ alkyl, —C(NOH)C$_{1-4}$ alkyl, —C(NOH)H, —C(NOC$_{1-4}$ alkyl)C$_{1-4}$ alkyl, —C(NOC$_{1-4}$ alkyl)H, hydroxyl, nitro, azido, cyano, —S(O)$_{0-2}$H, —S(O)$_{0-2}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, —P(O)(OH)$_2$ or P(O)(OC$_{1-4}$alkyl)$_2$.

$R^{12}$ is halogen, oxo, C$_{1-6}$ alkyl, halogenated C$_{1-6}$ alkyl, C$_{2-6}$ alkenyl, C$_{2-6}$ alkynyl, C$_{1-6}$ alkoxy, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$, alkyl, —NHCOC$_{1-4}$ alkyl, —NHCOOC$_{1-4}$ alkyl, —NHCONHC$_{1-4}$ alkyl, —N(C$_{1-4}$ alkyl)CONHC$_{1-4}$ alkyl, —N(C$_{1-4}$ alkyl)CON(C$_{1-4}$ alkyl)$_2$, —NHCON(C$_{1-4}$ alkyl)$_2$, —C(O)H, —C(O)C$_{1-4}$ alkyl, carboxy, —C(O)OC$_{1-4}$ alkyl, —C(NOH)C$_{1-4}$ alkyl, —C(NOH)H, hydroxyl, nitro, azido, cyano, —S(O)$_{0-2}$H, —S(O)$_{0-2}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, or —P(O)(OH)$_2$.

$R^{12}$ is halogen, oxo, C$_{1-6}$ alkyl, halogenated C$_{1-6}$ alkyl, C$_{2-6}$ alkenyl, C$_{2-6}$ alkynyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)C$_{1-4}$ alkyl, carboxy, —C(O)OC$_{1-4}$ alkyl, hydroxyl, C$_{1-6}$ alkoxy, nitro, nitroso, azido, or cyano.

$R^{12}$ is halogen, oxo, C$_{1-6}$ alkyl, halogenated C$_{1-6}$ alkyl, C$_{2-6}$ alkenyl, C$_{2-6}$ alkynyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)C$_{1-4}$ alkyl, carboxy, —C(O)OC$_{1-4}$ alkyl, hydroxyl, C$_{1-6}$ alkoxy, nitro, azido, or cyano.

$R^{12}$ is halogen, oxo, C$_{1-6}$ alkyl, halogenated C$_{1-6}$ alkyl, C$_{2-6}$ alkenyl, C$_{2-6}$ alkynyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —NHCOH, —N(C$_{1-4}$ alkyl)COH, —N(C$_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)C$_{1-4}$ alkyl, carboxy, —C(O)OC$_{1-4}$ alkyl, hydroxyl, or C$_{1-6}$ alkoxy.

$R^{12}$ is halogen, oxo, C$_{1-6}$ alkyl, halogenated C$_{1-6}$ alkyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —N(C$_{1-4}$ alkyl)COC$_{1-4}$ alkyl, —NHCOC$_{1-4}$ alkyl, carboxy, —C(O)OC$_{1-4}$ alkyl, hydroxyl, or C$_{1-6}$ alkoxy.

It will be appreciated by those skilled in the art that the compounds in accordance with the present invention can exists as stereoisomers (for example, optical (+ and −), geometrical (cis and trans) and conformational isomers (axial and equatorial). All such stereoisomers are included in the scope of the present invention.

It will be appreciated by those skilled in the art that the compounds in accordance with the present invention can contain a chiral center. The compounds of formula (I) may thus exist in the form of two different optical isomers (i.e. (+) or (−) enantiomers). All such enantiomers and mixtures thereof including racemic mixtures are included within the scope of the invention. The single optical isomers or enantiomers can be obtained by method well known in the art, such as chiral HPLC, enzymatic resolution and chiral auxiliary.

In one embodiment, the compounds of the present invention are provided in the form of a single enantiomer at least 95%, at least 97% and at least 99% free of the corresponding enantiomer.

In a further embodiment the compound of the present invention are in the form of the (+) enantiomer at least 95% free of the corresponding (−) enantiomer.

In a further embodiment the compound of the present invention are in the form of the (+) enantiomer at least 97% free of the corresponding (−) enantiomer.

In a further embodiment the compound of the present invention are in the form of the (+) enantiomer at least 99% free of the corresponding (−) enantiomer.

In a further embodiment, the compounds of the present invention are in the form of the (−) enantiomer at least 95% free of the corresponding (+) enantiomer.

In a further embodiment the compound of the present invention are in the form of the (−) enantiomer at least 97% free of the corresponding (+) enantiomer.

In a further embodiment the compound of the present invention are in the form of the (−) enantiomer at least 99% free of the corresponding (+) enantiomer.

There is also provided pharmaceutically acceptable salts of the compounds of the present invention. By the term pharmaceutically acceptable salts of compounds are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not themselves pharmaceutically acceptable, may be useful as intermediates in obtaining the compounds of the invention and their pharmaceutically acceptable acid addition salts.

Salts derived from amino acids are also included (e.g. L-arginine, L-Lysine).

Salts derived from appropriate bases include alkali metals (e.g. sodium, lithium, potassium), alkaline earth metals (e.g. calcium, magnesium), ammonium, $NR_4+$ (where R is $C_{1-4}$ alkyl) salts, choline, meglumine and tromethamine.

A reference hereinafter to a compound according to the invention includes that compound and its pharmaceutically acceptable salts.

In one embodiment of the invention, the pharmaceutically acceptable salt is a sodium salt.

In one embodiment of the invention, the pharmaceutically acceptable salt is a lithium salt.

In one embodiment of the invention, the pharmaceutically acceptable salt is a potassium salt.

In one embodiment of the invention, the pharmaceutically acceptable salt is a tromethamine salt.

In one embodiment of the invention, the pharmaceutically acceptable salt is an L-arginine salt.

In one embodiment of the invention, the pharmaceutically acceptable salt is meglumine salt.

It will be appreciated by those skilled in the art that the compounds in accordance with the present invention can exist in different polymorphic forms. As known in the art, polymorphism is the ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

It will further be appreciated by those skilled in the art that the compounds in accordance with the present invention can exist in different solvate forms, for example hydrates. Solvates of the compounds of the invention may also form when solvent molecules are incorporated into the crystalline lattice structure of the compound molecule during the crystallization process.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "alkyl" represents a linear, branched or cyclic hydrocarbon moiety. The terms "alkenyl" and "alkynyl" represent a linear, branched or cyclic hydrocarbon moiety which has one or more double bonds or triple bonds in the chain, respectively. Examples of alkyl, alkenyl, and alkynyl groups include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl, butenyl, isobutenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclopropyl, cyclobutyl, cyclopentyl, cyclohexenyl, cyclohexdienyl and cyclohexyl. Where indicated the "alkyl," "alkenyl," and "alkynyl" can be optionally substituted such as in the case of haloalkyls in which one or more hydrogen atom is replaced by a halogen, e.g., an alkylhalide. Examples of haloalkyls include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl. Aside from halogens, where indicated, the alkyl, alkenyl or alkynyl groups can also be optionally substituted by, for example, oxo, $-NR_dR_e$, $-CONR_dR_e$, $=NO-R_e$, $-NR_d COR_e$, carboxy, $-C(=NR_d)NR_eR_f$, azido, cyano, $C_{1-6}$ alkyloxy, $C_{2-6}$ alkenyloxy, $C_{2-6}$ alkynyloxy, $-N(R_d)C(=NR_e)-NR_fR_g$, hydroxyl, nitro, nitroso, $-N(R_h)CONR_iR_j$, $-S(O)_{0-2}R_a$, $-C(O)R_a$, $-C(O)OR_a$, $-SO_2NR_aR_b$, $-NR_aSO_2R_b$, $-NR_aSO_2NR_bR_c$, $-CR_aN=OR_b$, $-ONR_e R_f$ and/or $-NR_aCOOR_b$, wherein $R_a$-$R_j$, are each independently H, $C_{1-4}$ alkyl, $C_{2-4}$ alkenyl or $C_{2-4}$ alkynyl.

The terms "cycloalkyl" and "cycloalkenyl" represent a cyclic hydrocarbon alkyl or alkenyl, respectively, and are meant to include monocyclic (e.g., cyclohexyl), spiro (e.g., spiro[2.3]hexanyl), fused (e.g., bicyclo[4.4.0]decanyl), and bridged (e.g., bicyclo[2.2.1]heptanyl) hydrocarbon moieties. Where indicated, the "cycloalkyl", and "cycloalkenyl" groups can also be optionally substituted as defined in "alkyl" and "alkenyl" definition, The terms "alkoxy," "alkenyloxy," and "alkynyloxy" represent an alkyl, alkenyl or alkynyl moiety, respectively, which is covalently bonded to the adjacent atom through an oxygen atom. Like the alkyl, alkenyl and alkynyl groups, where indicated the alkoxy, alkenyloxy and alkynyloxy groups can also be optionally substituted. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy. The alkoxy, alkenyloxy, and alkynyloxy groups can be optionally substituted by, for example, halogens, oxo, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, $C_{1-6}$ alkyl, $C_{2-6}$ alkenyl, $C_{2-6}$ alkynyl, —$N(R_h)CONR_iR_j$, $S(O)_{0-2}R_a$, $C(O)R_a$, $C(O)OR_a$, =NO—$R_e$, —$SO_2NR_aR_b$, —$NR_aSO_2R_b$, —$NR_aSO_2NR_bR_c$, —$CR_aN=OR_b$, —$ONR_eR_f$ and/or —$NR_aCOOR_b$, wherein $R_a$-$R_j$ are each independently H, $C_{1-4}$ alkyl, $C_{2-4}$ alkenyl or $C_{2-4}$ alkynyl.

The term "aryl" represents a carbocyclic moiety containing at least one benzenoid-type ring (i.e., may be monocyclic or polycyclic), and which where indicated may be optionally substituted with one or more substituents. Examples include but are not limited to phenyl, tolyl, dimethylphenyl, aminophenyl, anilinyl, naphthyl, anthryl, phenanthryl or biphenyl. The aryl groups can be optionally substituted by, for example, halogens, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, —$N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, —$S(O)_{0-2}R_a$, optionally substituted 5-12 member heteroaryl, optionally substituted 6-18 member heteroaralkyl, optionally substituted 3-12 member heterocycle, optionally substituted 4-18 member heterocycle-alkyl, —$C(O)R_a$, —$C(O)OR_a$, —$SO_2NR_aR_b$, —$NR_aSO_2R_b$, —$NR_aSO_2NR_bR_c$, —$CR_aN=OR_b$, —$ONR_eR_f$ and/or —$NR_aCOOR_b$, wherein $R_a$-$R_j$ are each independently H, $C_{1-4}$ alkyl, $C_{2-4}$ alkenyl or $C_{2-4}$ alkynyl.

The terms "aryloxy," represent an aryl moiety substituted with an oxygen, wherein the point of attachment to the molecule it substitutes is on the oxygen. Where indicated the aryloxy group can also be optionally substituted by one or more substituents, for example, halogens, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, —$N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, $S(O)_{0-2}R_a$, optionally substituted 5-12 member heteroaryl, optionally substituted 6-18 member heteroaralkyl, optionally substituted 3-12 member heterocycle, optionally substituted 4-18 member heterocycle-alkyl, $C(O)R_a$, $C(O)OR_a$, $SO_2NR_aR_b$, $NR_aSO_2R_b$, $NR_aSO_2NR_bR_c$, $CR_aN=OR_b$, —$ONR_eR_f$ or $NR_aCOOR_b$, wherein $R_a$-$R_j$ are each independently H, $C_{1-4}$ alkyl, $C_{2-4}$ alkenyl, or $C_{2-4}$ alkynyl.

The term "aralkyl" represents an aryl group attached to the adjacent atom by an alkyl, alkenyl or alkynyl. Like the aryl groups, where indicated the aralkyl groups can also be optionally substituted. Examples include but are not limited to benzyl, benzhydryl, trityl, phenethyl, 3-phenylpropyl, 2-phenylpropyl, 4-phenylbutyl and naphthylmethyl. Where indicated, the aralkyl groups can be optionally substituted by, for example, halogens, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, —$N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, —$S(O)_{0-2}R_e$, optionally substituted 5-12 member heteroaryl, optionally substituted 6-18 member heteroaralkyl, optionally substituted 3-12 member heterocycle, optionally substituted 4-18 member heterocycle-alkyl, —$C(O)R_e$, —$C(O)OR_e$, —$SO_2NR_aR_b$, —$NR_aSO_2R_b$, —$NR_aSO_2NR_bR_c$, —$CR_aN=OR_b$, —$ONR_eR_f$ and/or —$NR_eCOOR_b$, wherein $R_a$-$R_j$ are each independently H, $C_{1-4}$ alkyl, $C_{2-4}$ alkenyl or $C_{2-4}$ alkynyl.

The term "heterocycle" represents an optionally substituted, non aromatic, saturated or partially saturated wherein said cyclic moiety is interrupted by at least one heteroatom selected from oxygen (O), sulfur (S) or nitrogen (N). It is understood that in a 3-12 member heterocycle moiety, the 3-12 member represents the total of the ring atoms present in the heterocycle moiety. Heterocycles may be monocyclic or polycyclic rings. Examples include but are not limited to azetidinyl, dioxolanyl, morpholinyl, morpholino, oxetanyl, piperazinyl, piperidyl, piperidino, cyclopentapyrazolyl, cyclopentaoxazinyl, cyclopentafuranyl, tetrahydrofuranyl, tetrahydrothiofuranyl, tetrahydrothiofuranyl, tetrahydropyranyl, tetrahydrothiopyranyl, tetrahydrothiopyranyl dioxyde, thiazolinyl, oxazolinyl, pyranyl, thiopyranyl, aziridinyl, azepinyl, dioxazepinyl, diazepinyl, oxyranyl, oxazinyl, pyrrolidinyl, thiopyranyl, thiolane, pyrazolidinyl, dioxanyl, and imidazolidinyl. Where indicated, the heterocyclic groups can be optionally substituted by, for example, halogens, oxo, —$NR_dR_e$, —$CONR_dR_e$, =NO—$R_e$, —$NR_dCOR_e$, carboxy, —$C(=NR_d)NR_eR_f$, azido, cyano, —$N(R_d)C(=NR_e)NR_fR_g$, hydroxyl, nitro, nitroso, —$N(R_h)CONR_iR_j$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, —$S(O)_{0-2}R_a$, $C_{6-10}$ aryl, $C_{6-10}$ aryloxy, $C_{7-10}$ arylalkyl, $C_{6-10}$ aryl-$C_{1-10}$ alkyloxy, —$C(O)R_a$, —$C(O)OR_e$, —$SO_2NR_aR_b$, —$NR_eSO_2R_b$, —$NR_eSO_2NR_bR_c$, —$CR_aN=OR_b$, —$ONR_eR_f$ and/or —$NR_aCOOR_b$, wherein $R_a$-$R_j$ are each independently H, $C_{1-4}$ alkyl, $C_{2-4}$ alkenyl or $C_{2-4}$ alkynyl.

The term "heterocycle-alkyl" represents an optionally substituted heterocycle group attached to the adjacent atom by an alkyl, alkenyl or alkynyl group. It is understood that in a 5-18 member heterocycle-alkyl moiety, the 5-18 member represents the total of the ring atoms present in the heterocycle moiety and the carbon atoms present in the alkyl, alkenyl or alkynyl group. For example, the following groups are encompassed by a 7 member heterocycle-alkyl (* represents the attachment point):

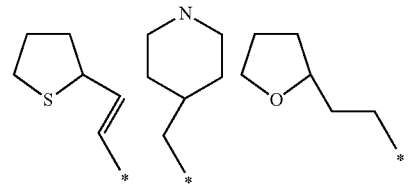

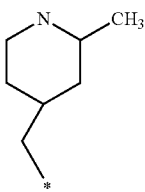

Where indicated the heterocycle-alkyl groups can be optionally substituted by, for example, halogens, oxo, —NR$_d$R$_e$, —CONR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, —S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, —C(O)R$_e$, —C(O)OR$_a$, =NO—R$_e$, —SO$_2$NR$_a$R$_b$, —NR$_a$SO$_2$R$_b$, —NR$_a$SO$_2$NR$_b$R$_c$, —CR$_a$N=OR$_b$, —ONR$_e$R$_f$ and/or —NR$_a$COOR$_b$, wherein R$_a$-R$_j$ are each independently H, C$_{1-4}$ alkyl, C$_{2-4}$ alkenyl or C$_{2-4}$ alkynyl.

The term "heteroaryl" represents an optionally substituted aromatic cyclic moiety wherein said cyclic moiety is interrupted by at least one heteroatom selected from oxygen (O), sulfur (S) or nitrogen (N). It is understood that in a 5-12 member heteroaryl moiety, the 5-12 member represents the total of the ring atoms present in the heteroaryl moiety. Heteroaryls may be monocyclic or polycyclic rings. Examples include but are not limited to dithiadiazinyl, furanyl, isooxazolyl, isothiazolyl, imidazolyl, oxadiazolyl, dioxazole, oxatriazole, oxazolyl, pyrazinyl, pyridazinyl, pyrimidinyl, pyridyl, pyrazolyl, pyrrolyl, thiatriazolyl, tetrazolyl, thiadiazolyl, triazolyl, thiazolyl, thienyl, tetrazinyl, thiadiazinyl, triazinyl, thiazinyl, furoisoxazolyl, imidazothiazolyl, thienoisothiazolyl, thienothiazolyl, imidazopyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolinyl, isoindolinyl, furopyrimidinyl, furopyridyl, benzofuranyl, isobenzofuranyl, thienopyrimidinyl, thienopyridyl, benzothienyl, benzoxazinyl, benzothiazinyl, quinazolinyl, naphthyridinyl, quinolinyl, isoquinolinyl, benzopyranyl, pyridopyridazinyl and pyridopyrimidinyl. Where indicated the heteroaryl groups can be optionally substituted by, for example, halogens, —NR$_d$R$_e$, —CONR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, —S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, —C(O)R$_a$, —C(O)OR$_a$, —SO$_2$NR$_a$R$_b$, —NR$_a$SO$_2$R$_b$, —NR$_a$SO$_2$NR$_b$R$_c$, —CR$_a$N=OR$_b$, —ONR$_e$R$_f$ and/or —NR$_a$COOR$_b$, wherein R$_a$-R$_j$ are each independently H, C$_{1-4}$ alkyl, C$_{2-4}$ alkenyl or C$_{2-4}$ alkynyl.

The term "heteroaralkyl" represents an optionally substituted heteroaryl group attached to the adjacent atom by an alkyl, alkenyl or alkynyl group. Where indicated the heteroaralkyl groups can be optionally substituted by, for example, halogens, —NR$_d$R$_e$, —CONR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, —S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, —C(O)R$_a$, —C(O)OR$_a$, —SO$_2$NR$_a$R$_b$, —NR$_a$SO$_2$R$_b$, —NR$_a$SO$_2$NR$_b$R$_c$, —CR$_a$N=OR$_b$, —ONR$_e$R$_f$ and/or —NR$_a$COOR$_b$, wherein R$_a$-R$_j$ are each independently H, C$_{1-4}$ alkyl, C$_{2-4}$ alkenyl or C$_{2-4}$ alkynyl. It is understood that in a 6-18 member heteroaralkyl moiety, the 6-18 member represents the total of the ring atoms present in the heteroaryl moiety and the carbon atoms present in the alkyl, alkenyl or alkynyl group. For example, the following groups are encompassed by a 7 member heteroaralkyl (* represents the attachment point):

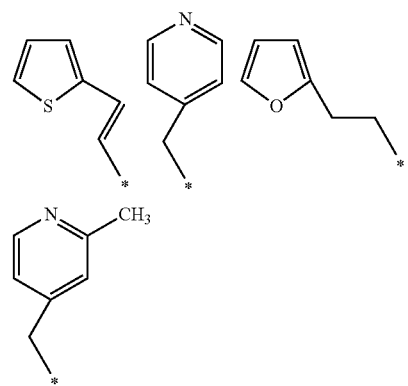

"Halogen atom" is specifically a fluorine atom, chlorine atom, bromine atom or iodine atom.

The term "oxo" represents =O.

A dash ("—") that is not between two letters or symbols is used to indicate a point of attachment for a substitutent. For example, —CONR$_d$R$_e$ is attached through the carbon of the amide.

A bond represented by a combination of a solid and dashed line, ie. ⚊⚊, may be either a single or double bond.

The term "guanidino" represents —N(R$_d$)C(=NR$_e$)NR$_f$R$_g$ wherein R$_d$, R$_e$, R$_f$ and R$_g$ are each independently selected from H, C$_{1-10}$ alkyl, C$_{2-10}$ alkenyl, C$_{2-10}$ alkynyl, C$_{6-12}$ aryl, and C$_{7-12}$ aralkyl, or R$_f$ and R$_g$ are taken together with the nitrogen to which they are attached to form an optionally substituted 4 to 10 member heterocycle or an optionally substituted 5-12 member heteroaryl.

The term "amidino" represents —C(=NR$_d$)NR$_e$R$_f$ wherein R$_d$, R$_e$ and R$_f$ are each independently selected from H, C$_{1-10}$ alkyl, C$_{2-10}$ alkenyl, C$_{2-10}$ alkynyl, C$_{6-12}$ aryl, and C$_{7-12}$ aralkyl, or R$_e$ and R$_f$ are taken together with the nitrogen to which they are attached to form an optionally substituted 4 to 10 member heterocycle or an optionally substituted 5-12 member heteroaryl.

The term "hydroxyl protecting group" is well known in the field of organic chemistry. Such protecting groups may be found in "Protective Groups in Organic Synthesis" second edition, Wiley-interscience publication, by T. W. Greene and P. G. M. Wuts. Examples of hydroxy protecting groups include but are not limited to benzyl, acetyl, benzoyl, pivaloyl and isopropyloxycarbonyl.

When there is a sulfur atom present, the sulfur atom can be at different oxidation levels, i.e., S, SO, or SO$_2$. All such oxidation levels are within the scope of the present invention.

The term "independently" means that a substituent can be the same or a different definition for each item.

In still another aspect, there is provided a method for prevention or treatment of HIV infections in a subject in need of such treatment comprising administering to the subject a therapeutically effective amount of a compound of formula (I) or a composition of the invention.

In still another aspect, there is provided a method for delaying the onset of AIDS or treating AIDS in a subject in need of such treatment comprising administering to the subject a therapeutically effective amount of a compound of formula (I) or a composition of the invention.

In still another aspect, there is provided a method for blocking cellular entry of HIV in a subject or for the prevention or treatment of HIV infections in a subject in need of such treatment comprising administering to the subject a pharmaceutical combination comprising at least one compound of formula (I) and at least one further therapeutic agent.

In still another aspect, there is provided a method for delaying the onset of AIDS or treating AIDS in a subject in need of such treatment comprising administering to the subject a pharmaceutical combination comprising at least one compound of formula (I) and at least one further therapeutic agent.

In another embodiment, the pharmaceutical combination of this invention may contain at least one further therapeutic agent which is an antiviral agent.

In one embodiment, the pharmaceutical combination of this invention may contain at least one further antiviral agent which is chosen from nucleoside and nucleotide analog reverse transcriptase inhibitors, non-nucleoside reverse transcriptase inhibitors, protease inhibitors, attachment and fusion inhibitors, integrase inhibitors, and maturation inhibitors.

In one embodiment, the pharmaceutical combinations of this invention may contain at least one other antiviral agent which is a nucleoside and nucleotide analog reverse transcriptase inhibitors chosen from 3TC (lamivudine, Epivir®), AZT (zidovudine, Retrovir®), Emtricitabine (Coviracil®, formerly FTC), d4T (2',3'-dideoxy-2',3'-didehydro-thymidine, stavudine and Zerit®), tenofovir (Viread®), 2',3'-dideoxyinosine (ddl, didanosine, Videx®), 2',3'-dideoxycytidine (ddC, zalcitabine, Hivid®), Combivir® (AZT/3TC or zidovudine/lamivudine combination), Trivizir® (AZT/3TC/abacavir or zidovudine/lamivudine/abacavir combination), abacavir (1592U89, Ziagen®), Epzicom® (abacavir and lamivudine), Truvada® (Tenofovir and emtricitabine), SPD-754 (apricitabine), Elvucitabine (ACH-126,443, (Beta-L-Fd4C), Alovudine (MIV-310), DAPD (amdoxovir), Racivir, phosphazid, stampidine, CMX-157, PPI-801/802 (formerly MIV-410), MIV-210, fozivudine tidoxil, KP-1461, Fosalvudine (HDP 99.0003), 9-[(2-hydroxymethyl)-1,3-dioxolan-4-yl]guanine, and 2-amino-9-[(2-hydroxymethyl)-1,3-dioxolan-4-yl]adenine.

In another embodiment, the pharmaceutical combination of this invention may contain at least one other antiviral agent which is a non-nucleoside reverse transcriptase inhibitor chosen from Nevirapine (Viramune®, NVP, BI-RG-587), delavirdine (Rescriptor®, DLV), efavirenz (DMP 266, Sustiva®), (+)-Calanolide A, Capravirine (AG1549, formerly S-1153), DPC083, MIV-150, TMC120, Intelence (Etravirine®, TMC125), TMC-278 or BHAP (delavirdine), calanolides, GW695634, RDEA806, RDEA427, RDEA640, UK-453061, BILR355, VRX 840773 and L-697,661 (2-Pyridinone 3benzoxazolMeNH derivative).

In another embodiment, the pharmaceutical combination of this invention may contain at least one other antiviral agent which is a protease inhibitor chosen from nelfinavir (Viracept®, NFV), amprenavir (141W94, Agenerase®), indinavir (MK-639, IDV, Crixivan®), saquinavir (Invirase®, Fortovase®, SQV), ritonavir (Norvir®, RTV), lopinavir (ABT-378, Kaletra®), Atazanavir (Reyataz®, BMS232632), mozenavir (DMP-450), fosamprenavir (GW433908), R0033-4649, Tipranavir (Aptivus®, PNU-140690), Darunavir (Prezista®, TMC114), SPI-256, Brecanavir (GW640385), P-1946, MK-8122 (formerly PPL-100) and VX-385.

In another embodiment, the pharmaceutical combination of this invention may contain at least one other antiviral agent which is an attachment and fusion inhibitor chosen from T-20 (enfuvirtide, Fuzeon®), T-1249, TRI-999, TRI-1144, Schering C (SCH-C), Vicriviroc (Schering D, SCH-D), FP21399, PRO-140, PRO 542, PRO 452, TNX-355, Aplaviroc (GW873140, AK602), TBR-220 (formerly TAK-220), TBR-652 (formerly TAK-652), PF-232798, Maraviroc (Selzentry®, UK-427,857) or soluble CD4, CD4 fragments, CD4-hybrid molecules, BMS-806, BMS-488043, AMD3100, AMD070, AMD887, INCB9471, INCB15050, KRH-2731, KRH-3140, SJ-3366, SP-01A, sifuvirtide, and KRH-3955.

In another embodiment, the pharmaceutical combination of this invention may contain at least one other antiviral agent which is an integrase inhibitor chosen from S-1360, L-870, 810, elvitegravir (GS9137, JKT 303), GS9137, L-870,812, raltegravir (Isentress®, MK-0518), MK-2048, GSK1349572, and C-2507.

In another embodiment, the pharmaceutical combination of this invention may contain at least one other antiviral agent which is a maturation inhibitor chosen from Vivecon (MPC-9055) and Bevirimat (PA-457).

In another embodiment, the pharmaceutical combination of this invention may contain at least one other antiviral agent which is a zinc finger inhibitor and is azodicarbonamide (ADA).

In another embodiment, the pharmaceutical combination of this invention may contain at least one other antiviral agent which is an antisense drug and is HGTV43.

In another embodiment, the pharmaceutical combination of this invention may contain at least one other antiviral agent which is an immunomodulator, immune stimulator or cytokine chosen from interleukin-2 (IL-2, Aldesleukin, Proleukin), granulocyte macrophage colony stimulating factor (GM-CSF), erythropoietin, Multikine, Ampligen, thymomodulin, thymopentin, foscarnet, HE2000, Reticulose, Murabutide, Resveratrol, HRG214, HIV-1 Immunogen (Remune), WF10 and EP HIV-1090.

In another embodiment, the pharmaceutical combination of this invention may contain at least one other antiviral agent chosen from 2',3'-dideoxyadenosine, 3'-deoxythymidine, 2',3'-dideoxy-2',3'-didehydrocytidine and ribavirin; acyclic nucleosides such as acyclovir and ganciclovir; interferons such as alpha-, beta- and gamma-interferon; glucuronation inhibitors such as probenecid; and TIBO drugs, HEPT, Pictovir® (VGX-410) and TSAO derivatives.

In another embodiment, the pharmaceutical combination of this invention may contain an inhibitor of the cytochrome P450.

In another embodiment, the pharmaceutical combination of this invention may contain an inhibitor of the cytochrome P450 chosen from atazanavir, clarithromycin, indinavir, itraconazole, ketoconazole, nefazodone, nelfinavir, ritonavir, saquinavir, telithromycin, amprenavir, erythromycin, fluconazole, fosamprenavir, grapefruit juice, fluvoxamine, fluoxetine, macrolide antibiotics, sertraline sulfaphenazole, Troleandomycin, cyclosporine, clomethiazole, atazanavir, mibefradil, vitamin E, bergamottin, dihydroxybergamottin, and pharmaceutically acceptable salts thereof.

In another embodiment, the pharmaceutical combination of this invention may contain an inhibitor of the cytochrome P450 which is ritonavir or a pharmaceutically acceptable salt thereof.

The combinations referred to above may conveniently be presented for use in the form of a pharmaceutical formulation and thus pharmaceutical formulations comprising a combination as defined above together with a pharmaceutically acceptable carrier thereof comprises a further aspect of the invention.

The individual components of such combinations may be administered either sequentially or simultaneously in separate or combined pharmaceutical formulations.

The individual components of such combinations may be administered either sequentially or simultaneously in separate or combined pharmaceutical formulations.

In a further embodiment, the compound of formula (I) and at least one further therapeutic agent are administered sequentially.

In a further embodiment, the compound of formula (I) and at least one further therapeutic agent are administered simultaneously.

Thus, a further embodiment of the invention is a kit for use in administering a combinations, the kit comprising: a first containment means for storing a compound according to formula I in the form of a pharmaceutical formulation further comprising a pharmaceutically acceptable carrier; and a second containment means for storing at least one further therapeutic agent in the form of a pharmaceutical formulation further comprising a pharmaceutically acceptable carrier.

In one embodiment, the present invention further provides a pharmaceutical composition comprising at least one compound having the formula (I) or a pharmaceutically acceptable salt thereof, or a pharmaceutically acceptable hydrate thereof, or a pharmaceutically acceptable solvate thereof, and at least one pharmaceutically acceptable carrier or excipient.

The terms "host" or "patient" or "subject" means a human, male or female, for example, a child, an adolescent, or an adult.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician. In general however a suitable dose will be in the range of from about 0.1 to about 750 mg/kg of body weight per day, for example, in the range of 0.5 to 60 mg/kg/day, or, for example, in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 µM, about 2 to 50 µM, about 3 to about 30 µM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

When a compound of the present invention or a pharmaceutically acceptable salt thereof is used in combination with a second therapeutic agent active against the same virus, the dose of each compound may be either the same as or differ from that when the compound is used alone. Appropriate doses will be readily appreciated by those skilled in the art.

While it is possible that, for use in therapy, a compound of the invention may be administered as the raw chemical, it is preferable to present the active ingredient as a pharmaceutical composition. The invention thus further provides a pharmaceutical composition comprising a compound of the present invention or a pharmaceutically acceptable salt thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension, or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Compositions suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration wherein the carrier is a solid are for example presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Compositions suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

Compounds according to the present invention include:

| | |
|---|---|
| 9-1 | 3β-O-(3',3'-Dimethylsuccinyl)-21-oxolup-18-en-28-oic acid N-benzylamide; |
| 9-2 | 3β-O-(3',3'-Dimethylsuccinyl)-21-oxolup-18-en-28-oic acid N-methylamide; |
| 9-3 | 3β-O-(3',3'-Dimethylsuccinyl)-21-oxolup-18-en-28-oic acid N-isopropylamide; |
| 9-4 | 3β-O-(3',3'-Dimethylsuccinyl)-21-oxolup-18-en-28-oic acid N-cyclohexylamide; |
| 9-5 | 3β-O-(3',3'-Dimethylsuccinyl)-21-oxolup-18-en-28-oic acid N-cyclohexyl methylamide; |
| 9-6 | 3β-O-(3',3'-Dimethylsuccinyl)-21-oxolup-18-en-28-oic acid N-piperidinyl acetamide; |
| 9-7 | 3β-O-(3',3'-Dimethylsuccinyl)-21-oxolup-18-en-28-oic acid N-morpholyl acetamide; |
| 9-8 | 3β-O-(3',3'-Dimethylsuccinyl)-21-oxolup-18-en-28-oic acid N-(4-acetyl piperazinyl) acetamide; |
| 9-9 | 3β-O-(3',3'-Dimethylsuccinyl)-21-oxolup-18-en-28-oic acid N-(4-methyl piperazinyl) acetamide; |
| 9-10 | 3β-O-(3',3'-Dimethylsuccinyl)-21-oxolup-18-en-28-oic acid N-benzamide; |
| 9-11 | 3β-O-(3',3'-Dimethylsuccinyl)-21-oxolup-18-en-28-oic acid N-methyl-N-benzylamide; |
| 9-12 | 3β-O-(3',3'-Dimethylsuccinyl)-21-oxolup-18-en-28-oic acid N-2-chloro-benzylamide; |
| 9-13 | 3β-O-(3',3'-Dimethylsuccinyl)-21-oxolup-18-en-28-oic acid N-3-chloro-benzylamide; |
| 9-14 | 3β-O-(3',3'-Dimethylsuccinyl)-21-oxolup-18-en-28-oic acid N-4-chloro-benzylamide; |
| 9-15 | 3β-O-(3',3'-Dimethylsuccinyl)-21-oxolup-18-en-28-oic acid N-4-methoxy-benzylamide; |
| 9-16 | 3β-O-(3',3'-Dimethylsuccinyl)-21-oxolup-18-en-28-oic acid N-pyridin-2-ylmethylamide; |
| 9-17 | 3β-O-(3',3'-Dimethylsuccinyl)-21-oxolup-18-en-28-oic acid N-pyridin-3-ylmethylamide; |
| 9-18 | 3β-O-(3',3'-Dimethylsuccinyl)-21-oxolup-18-en-28-oic acid N-pyridin-4-ylmethylamide; |
| 9-19 | 3β-O-(3',3'-Dimethylsuccinyl)-21-oxolup-18-en-28-oic acid N-[2-(4-methoxy-phenyl)-ethyl]-acetamide; |
| 9-20 | 3β-O-(3',3'-Dimethylsuccinyl)-21-oxolup-18-en-28-oic acid N-(2-acetylamino-ethyl)-carbamic acid tert-butyl ester; |
| 9-21 | 3β-O-(3',3'-Dimethylsuccinyl)-21-oxolup-18-en-28-oic acid N-(2-amino-ethyl)-acetamide; |
| 9-22 | 3β-O-(3',3'-Dimethylsuccinyl)-21-oxolup-18-en-28-oic acid N-(2-acetylamino-ethyl)-acetamide; |
| 9-23 | 3β-O-(3',3'-Dimethylsuccinyl)-21-oxolup-18-en-28-oic acid N-[2-(3-isopropyl-ureido)-ethyl]-acetamide; |
| 9-24 | 3β-O-(3',3'-Dimethylsuccinyl)-21-oxolup-18-en-28-oic acid N-(2-acetylamino-ethyl)-carbamic acid methyl ester; |

-continued

| | |
|---|---|
| 9-25 | 3β-O-(3',3'-Dimethylsuccinyl)-21-oxolup-18-en-28-oic acid N-pyridin-2-yl-acetamide; |
| 9-26 | 3β-O-(3',3'-Dimethylsuccinyl)-21-oxolup-18-en-28-oic acid N-pyridin-3-yl-acetamide; |
| 9-27 | 3β-O-(3',3'-Dimethylsuccinyl)-21-oxolup-18-en-28-oic acid N-1-acetyl-piperazine-4-carboxylic acid tert-butyl ester; |
| 9-28 | 3β-O-(3',3'-Dimethylsuccinyl)-21-oxolup-18-en-28-oic acid N-piperazinyl-acetamide; |
| 9-29 | 3β-O-(3',3'-Dimethylsuccinyl)-21-oxolup-18-en-28-oic acid N-1-(4-hydroxy-piperidin-1-yl)-acetamide; |
| 9-30 | 3β-O-(3',3'-Dimethylsuccinyl)-21-oxolup-18-en-28-oic acid N-1-acetylamino-piperidine-4-carboxylic acid tert-butyl ester; |
| 9-31 | 3β-O-(3',3'-Dimethylsuccinyl)-21-oxolup-18-en-28-oic acid N-(4-aminopiperidine)-acetamide; |
| 9-32 | 3β-O-(3',3'-Dimethylsuccinyl)-21-oxolup-18-en-28-oic acid N-(4-amino-N-1-acetyl-piperidine)-acetamide; |
| 9-33 | 3β-O-(3',3'-Dimethylsuccinyl)-21-oxolup-18-en-28-oic acid N-(1-phenyl-ethyl)-acetamide; |
| 9-34 | 3β-O-(3',3'-Dimethylsuccinyl)-21-oxolup-18-en-28-oic acid N-(1-methyl-1-phenyl-ethyl)-acetamide; |
| 9-35 | 3β-O-(3',3'-Dimethylsuccinyl)-21-oxolup-18-en-28-oic acid N-(tert-butyl)-acetamide; |
| 9-36 | 3β-O-(3',3'-Dimethylsuccinyl)-21-oxolup-18-en-28-oic acid N-(8-amino-3,8-diaza-bicyclo[3.2.1]octane-3-benzamide)-acetamide; |
| 9-37 | 3β-O-(3',3'-Dimethylsuccinyl)-21-oxolup-18-en-28-oic acid N-4-piperazi-2-one acetamide; |
| 9-38 | 3β-O-(3',3'-Dimethylsuccinyl)-21-oxolup-18-en-28-oic acid N-pyrimidin-2-yl-acetamide; |
| 9-39 | 3β-O-(3',3'-Dimethylsuccinyl)-21-oxolup-18-en-28-oic acid N-(4-N'-isopropylureido-1-piperazine)-acetamide; |
| 9-40 | 3β-O-(3',3'-Dimethylsuccinyl)-21-oxolup-18-en-28-oic acid N-1-acetyl-piperazine-4-carboxylic acid methyl ester; |
| 9-41 | 3β-O-(3',3'-Dimethylsuccinyl)-21-oxolup-18-en-28-oic acid N-(4-amino carboxylic acid tert-butyl-ester-1-piperidine)-acetamide; |
| 9-42 | 3β-O-(3',3'-Dimethylsuccinyl)-21-oxolup-18-en-28-oic acid N-(4-amino-1-piperidine)-acetamide; |
| 9-43 | 3β-O-(3',3'-Dimethylsuccinyl)-21-oxolup-18-en-28-oic acid N-(4-acetylamino-1-piperidine)-acetamide; |
| 9-44 | 3β-O-(3',3'-Dimethylsuccinyl)-21-oxolup-18-en-28-oic acid N-[(4-amino-N'-isopropylureido)-1-piperidine]-acetamide; |
| 9-45 | 3β-O-(3',3'-Dimethylsuccinyl)-21-oxolup-18-en-28-oic acid N-(4-amino carboxylic acid methyl ester-1-piperidine)-acetamide; |
| 9-46 | 3β-O-(3',3'-Dimethylsuccinyl)-21-oxolup-18-en-28-oic acid N-4-(1-methyl-piperazi-2-one)-acetamide; |
| 9-47 | 3β-O-(3',3'-Dimethylsuccinyl)-21-oxolup-18-en-28-oic acid N-2-methyl-phen-1-yl acetamide; |
| 9-48 | 3β-O-(3',3'-Dimethylsuccinyl)-21-oxolup-18-en-28-oic acid N-3-methyl-phen-1-yl acetamide; |
| 9-49 | 3β-O-(3',3'-Dimethylsuccinyl)-21-oxolup-18-en-28-oic acid N-4-methyl-phen-1-yl acetamide; |
| 9-50 | 3β-O-(3',3'-Dimethylsuccinyl)-21-oxolup-18-en-28-oic acid N-8-acetylamino-3,8-diaza-bicyclo[3.2.1]octane-3-carboxylic acid tert-butyl ester; |
| 9-51 | 3β-O-(3',3'-Dimethylsuccinyl)-21-oxolup-18-en-28-oic acid N-pyrimidin-5-yl-acetamide; |
| 9-52 | 3β-O-(3',3'-Dimethylsuccinyl)-21-oxolup-18-en-28-oic acid N-pyridin-4-yl-acetamide; |
| 9-53 | 3β-O-(3',3'-Dimethylsuccinyl)-21-oxolup-18-en-28-oic acid N-3-amino-1-methyl-1H-pyrazole-acetamide; |
| 9-54 | 3β-O-(3',3'-Dimethylsuccinyl)-21-oxolup-18-en-28-oic acid N-5-amino-1-methyl-1H-pyrazole acetamide; |
| 9-55 | 3β-O-(3',3'-Dimethylsuccinyl)-21-oxolup-18-en-28-oic acid N-4-methyl-pyrimidin-5-yl-acetamide; |
| 9-56 | 3β-O-(3',3'-Dimethylsuccinyl)-21-oxolup-18-en-28-oic acid N-4-methyl-pyrimidin-2-yl-acetamide; |
| 9-57 | 3β-O-(3',3'-Dimethylsuccinyl)-21-oxolup-18-en-28-oic acid N-4-amino-1-methyl-1H-pyrazole acetamide; |
| 9-58 | 3β-O-(3',3'-Dimethylsuccinyl)-21-oxolup-18-en-28-oic acid N-4,6-dimethyl-pyrimidin-2-yl-acetamide; |
| 9-59 | 3β-O-(3',3'-Dimethylsuccinyl)-21-oxolup-18-en-28-oic acid N-pyrazin-2-yl-acetamide; |
| 9-60 | 3β-O-(3',3'-Dimethylsuccinyl)-21-oxolup-18-en-28-oic acid N-quinolin-3-yl-acetamide; |
| 9-61 | 3β-O-(3',3'-Dimethylsuccinyl)-21-oxolup-18-en-28-oic acid N-(2-pyrrolidin-1-yl-ethyl)-acetamide; |
| 9-62 | 3β-O-(3',3'-Dimethylsuccinyl)-21-oxolup-18-en-28-oic acid N-(5-methyl-[1,3,4]oxadiazol-2-yl)-acetamide; |
| 9-63 | 3β-O-(3',3'-Dimethylsuccinyl)-21-oxolup-18-en-28-oic acid N-isoquinolin-4-yl-acetamide; |

-continued

| | |
|---|---|
| 9-64 | 3β-O-(3',3'-Dimethylsuccinyl)-21-oxolup-18-en-28-oic acid N-pyrimidin-4-yl-acetamide; |
| 9-65 | 3β-O-(3',3'-Dimethylsuccinyl)-21-oxolup-18-en-28-oic acid N-2-trifluoromethyl-phen-1-yl acetamide; |
| 9-66 | 3β-O-(3',3'-Dimethylsuccinyl)-21-oxolup-18-en-28-oic acid N-(1-methyl-1H-tetrazol-5-yl)-acetamide; |
| 9-67 | 3β-O-(3',3'-Dimethylsuccinyl)-21-oxolup-18-en-28-oic acid N-(4-amino carboxylic acid ethyl ester-1-piperidine)-acetamide; |
| 9-68 | 3β-O-(3',3'-Dimethylsuccinyl)-21-oxolup-18-en-28-oic acid N-(4-amino carboxylic acid isopropyl ester-1-piperidine)-acetamide; |
| 9-69 | 3β-O-(3',3'-Dimethylsuccinyl)-21-oxolup-18-en-28-oic acid N-cyclopropylmethyl acetamide; |
| 9-70 | 3β-O-(3',3'-Dimethylsuccinyl)-21-oxolup-18-en-28-oic acid N-azetidine-1 acetamide; |
| 9-71 | 3β-O-(3',3'-Dimethylsuccinyl)-21-oxolup-18-en-28-oic acid N-(2,2,2-trifluoro-ethyl)-acetamide; |
| 9-72 | 3β-O-(3',3'-Dimethylsuccinyl)-21-oxolup-18-en-28-oic acid N-4-trifluoro-pyrimidin-2-yl-acetamide; |
| 9-73 | 3β-O-(3',3'-Dimethylsuccinyl)-21-oxolup-18-en-28-oic acid N-(1-cyclopropyl-1-methyl-ethyl)-acetamide; |
| 9-74 | 3β-O-(3',3'-Dimethylsuccinyl)-21-oxolup-18-en-28-oic acid N-(4-dimethylamino-piperidin-1-yl)-acetamide; |
| 9-75 | 3β-O-(3',3'-Dimethylsuccinyl)-21-oxolup-18-en-28-oic acid N-(2,2,2-trifluoro-1-methyl-ethyl)-acetamide; |
| 9-76 | 3β-O-(3',3'-Dimethylsuccinyl)-21-oxolup-18-en-28-oic acid N-(5-methyl-[1,3,4]thiadiazol-2-yl)-acetamide; |
| 9-77 | 3β-O-(3',3'-Dimethylsuccinyl)-21-oxolup-18-en-28-oic acid N-(2,2,2-trifluoro-1,1-dimethyl-ethyl)-acetamide; |
| 9-78 | 3β-O-(3',3'-Dimethylsuccinyl)-21-oxolup-18-en-28-oic acid N-tert-butyl-N-methyl-acetamide; |
| 9-79 | 3β-O-(3',3'-Dimethylsuccinyl)-21-oxolup-18-en-28-oic acid N-(R)-2-acetylaminomethyl-pyrrolidine-1-carboxylic acid tert-butyl ester; |
| 9-80 | 3β-O-(3',3'-Dimethylsuccinyl)-21-oxolup-18-en-28-oic acid N-(S)-2-acetylaminomethyl-pyrrolidine-1-carboxylic acid tert-butyl ester; |
| 9-81 | 3β-O-(3',3'-Dimethylsuccinyl)-21-oxolup-18-en-28-oic acid N-((R)-1-pyrrolidin-2-ylmethyl)-acetamide; |
| 9-82 | 3β-O-(3',3'-Dimethylsuccinyl)-21-oxolup-18-en-28-oic acid N-((S)-1-pyrrolidin-2-ylmethyl)-acetamide; |
| 9-83 | 3β-O-(3',3'-Dimethylsuccinyl)-21-oxolup-18-en-28-oic acid N-((R)-1-methyl-pyrrolidin-2-ylmethyl)-acetamide; |
| 9-84 | 3β-O-(3',3'-Dimethylsuccinyl)-21-oxolup-18-en-28-oic acid N-((S)-1-methyl-pyrrolidin-2-ylmethyl)-acetamide; |
| 9-85 | 3β-O-(3',3'-Dimethylsuccinyl)-21-oxolup-18-en-28-oic acid N-(4,4-difluoro-cyclohexyl) acetamide; |
| 9-86 | 3β-O-(3',3'-Dimethylsuccinyl)-21-oxolup-18-en-28-oic acid N-2-chloro-phen-1-yl acetamide; |
| 9-87 | 3β-O-(3',3'-Dimethylsuccinyl)-21-oxolup-18-en-28-oic acid N-2-isopropyl-phen-1-yl acetamide; |
| 9-88 | 3β-O-(3',3'-Dimethylsuccinyl)-21-oxolup-18-en-28-oic acid N-4-fluoro-phen-1-yl acetamide; |
| 9-89 | 3β-O-(3',3'-Dimethylsuccinyl)-21-oxolup-18-en-28-oic acid N-quinazolin-2-yl acetamide; |
| 9-90 | 3β-O-(3',3'-Dimethylsuccinyl)-21-oxolup-18-en-28-oic acid N-(1-methyl-1H-tetrazol-3-yl)-acetamide; |
| 9-91 | 3β-O-(3',3'-Dimethylsuccinyl)-21-oxolup-18-en-28-oic acid N-(5-methyl-isoxazol-3-yl)-acetamide; |
| 9-92 | 3β-O-(3',3'-Dimethylsuccinyl)-21-oxolup-18-en-28-oic acid N-(1,3-dihydro-isoindol-2-yl)-acetamide; |
| 9-93 | 3β-O-(3',3'-Dimethylsuccinyl)-21-oxolup-18-en-28-oic acid N-(4,4-difluoro-cyclohexylmethyl)-acetamide; |
| 9-94 | 3β-O-(3',3'-Dimethylsuccinyl)-21-oxolup-18-en-28-oic acid N-4,4-difluoro-piperidine acetamide; |
| 9-95 | 3β-O-(3',3'-Dimethylsuccinyl)-21-oxolup-18-en-28-oic acid N-8-acetylamino-3,8-diaza-bicyclo[3.2.1]octane-3-acetamide. | and pharmaceutically acceptable salts thereof.

Analytical HPLC is carried out under standard conditions using a Phenomenex Gemini C18 column, 250×4.6 mm, 3 μm, 110 Å for the methods A, B, C, D and E. Elution is performed using a linear gradient over 40 minutes with a flow rate of 1 mL/min. as described in the following table (Solvent A is 0.01% TFA in H$_2$O; solvent B is 0.01% TFA in CH$_3$CN):

| Methods | A | B | C | D | E |
|---|---|---|---|---|---|
| Solvent B | 50 to 90% | 60 to 100% | 30 to 70% | 20 to 60% | 40 to 80% |

Analytical HPLC is carried out under standard conditions using a Waters Symmetry C18 column, 50×4.6 mm, 3.5 μm, for the method F and a Varian Pursuit C18 column, 50×4.6 mm, 3.5 μm, for the methods G and H. Elution is performed using a linear gradient over 20 minutes with a flow rate of 1 mL/min. as described in the following table (Solvent A is 0.01% TFA in H$_2$O; solvent B is 0.01% TFA in CH$_3$CN):

| Methods | F | G | H |
|---|---|---|---|
| Solvent B | 50 to 95% | 40 to 85% | 50 to 95% |

Analytical LC/MS is carried out under standard conditions using a Symmetry Shield RP18 column, 2.1×50 mm, 3.5 μM for methods a and b. Elution is performed using a linear gradient over 20 minutes with a flow rate of 0.5 mL/min. as described in the following table (Solvent A is 0.01% TFA in H$_2$O; solvent B is 0.01% TFA in CH$_3$CN):

| Methods | a | b |
|---|---|---|
| Solvent B | 5 to 85% | 40 to 95% |

The following abbreviations may be used as follows:

| | |
|---|---|
| br | broad |
| DCE | 1,2-dichloroethane |
| DCM | dichloromethane |
| DMAP | 4-Dimethylaminopyridine |
| DMF | Dimethylformamide |
| Eq. | equivalent |
| HCl | hydrochloric acid |
| NaOH | Sodium hydroxide |
| ND | not determined |
| PCC | Pyridinium chlorochromate |
| Sept. | Septuplet |
| TFA | Trifluoroacetic acid |
| THF | Tetrahydrofuran |

Scheme 1

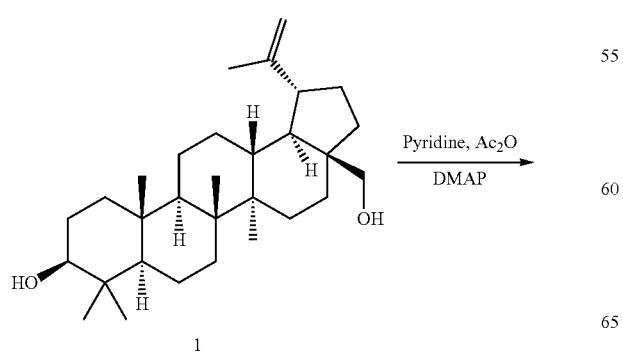

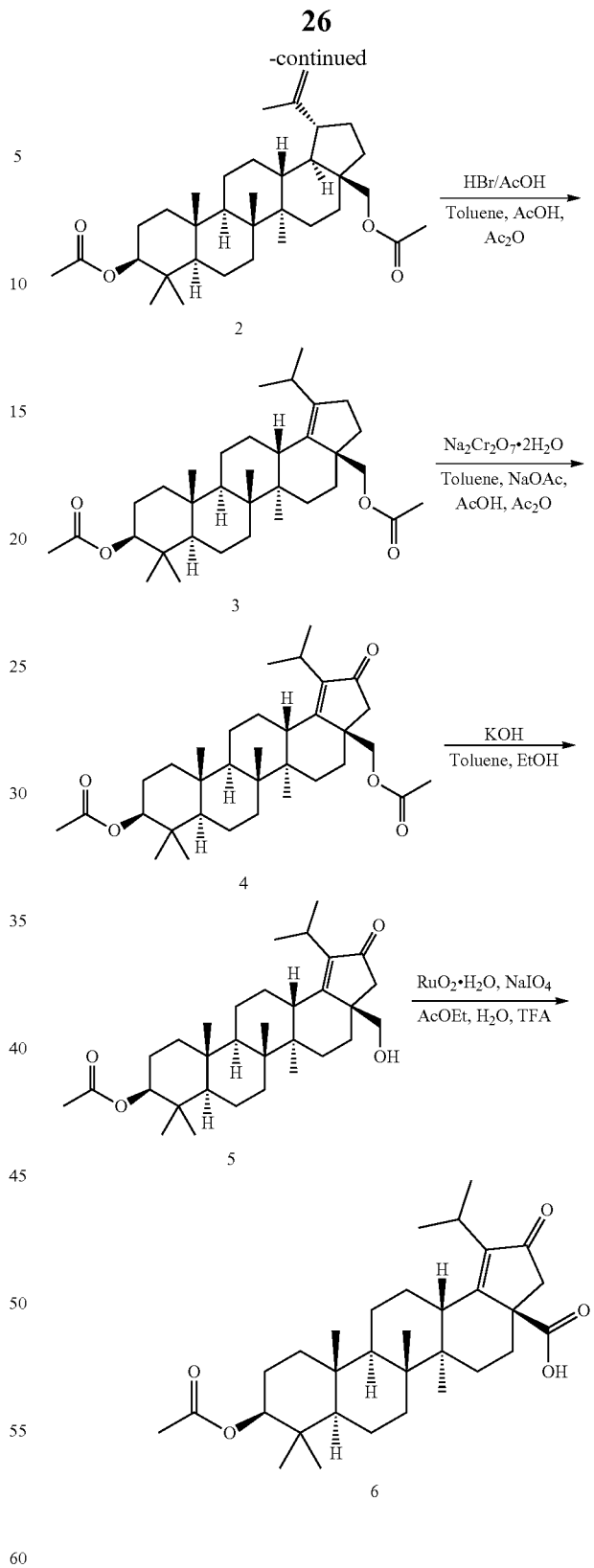

Lup-20(29)-ene-3β,28-diyl diacetate 2

To a mixture of Betulin 1 (100 g, 0.225 mol) in 120 mL of anhydrous pyridine is added DMAP (2.68 g, 0.022 mol) and 48 mL (0.495 mol) of acetic anhydride. The reaction mixture is stirred at room temperature for 5 hours and diluted with iced water. The mixture is then extracted with DCM (3×200 mL) and the combined organic layers are washed back with aqueous HCl 1N (3×200 mL), brine and dried over sodium sulfate. The pale yellow solid is taken up with methanol (400 mL), filtered off and rinsed with methanol (2×400 mL) to give the title compound 2 (102.35 g, 86.3%) as a colorless solid.

Lup-18-ene-3β,28-diyl diacetate 3

A solution of 90 mL of HBr in acetic acid (33%) is added to a mixture of 2 (45.03 g, 85.48 mmol) in 90 mL of toluene, 90 mL of acetic anhydride and 90 mL of acetic acid previously heated at 90° C. The reaction mixture is stirred and heated at this temperature for 4 hours. After cooling, 46 g of sodium acetate is added and the mixture is evaporated to dryness. The pale brownish residue is re-evaporated from methanol (50 mL) and the residue is triturated with methanol, filtered off and washed with methanol to obtain 42.35 g of a pale brownish solid. After recrystallization in ethyl acetate (0.5 L) and cooling on ice for 0.5 hour, the title compound 3 (25.78 g, 60.4%) is isolated as a colorless solid.

21-Oxo-lup-18-ene-3β,28-diyl diaceate 4

A mixture of 3 (22 g, 41.76 mmol), sodium acetate (19.5 g, 238 mmol) and sodium dichromate dihydrate (14.9 g, 50.1 mmol) in 280 mL of anhydrous toluene, 350 mL of acetic acid and 76 mL of acetic anhydride is stirred overnight at 60° C. After cooling, water (500 mL) and ethyl acetate (350 mL) are added and the layers are separated. The organic layer is washed successively with water (500 mL), a saturated solution of sodium carbonate (3×250 mL), water (500 mL) and brine (3×200 mL), dried over sodium sulfate and concentrated in vacuo. The gummy yellow solid is triturated with methanol and filtered off to yield the title compound 4 (21.41 g, 94.8%) as a colorless solid.

28-Hydroxy-21-oxolup-18-en-3β-yl acetate 5

A solution of compound 4 (12.07 g, 22.3 mmol) and potassium hydroxide (1.49 g, 26.76 mmol) in a mixture 1:1 of toluene and ethanol (0.72 L) is stirred vigorously at room temperature for 1 hour. The reaction mixture is neutralized with aqueous HCl 1N (27 mL) and evaporated to dryness. The solid is taken up with water and a minimum of acetone then filtered off. The precipitate is washed with water and dried to yield the title compound 5 (10.24 g, 92%) as a colorless solid.

3β-Acetoxy-21-oxolup-18-en-28-oic acid 6 (see WO2003/045971)

A suspension of compound 5 (10.24 g, 20.5 mmol) in ethyl acetate (720 mL) is added to a mixture of ruthenium oxide (IV) hydrate (272 mg, 2.05 mmol) and sodium periodate (26.3 g, 123 mmol) in water (650 mL) and TFA (11 mL). The biphasic mixture is stirred vigorously overnight at room temperature. Ethanol (100 mL) is added and the separated organic layer is filtered through a short column of silica gel. Water (400 mL) is added and the organic layer is dried over sodium sulfate, and concentrated in vacuo. The yellow solid is taken up with diethyl ether, filtered off and washed with diethyl ether to give the title compound 6 (4.96 g, 47.2%) as a colorless solid.

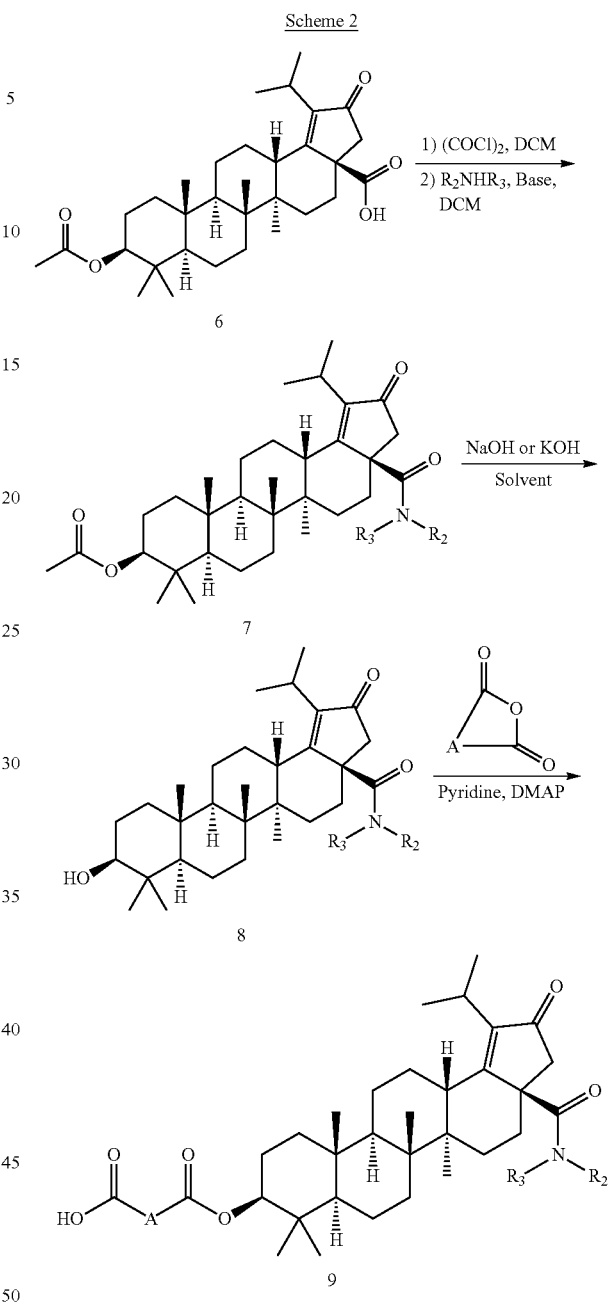

Scheme 2

General Procedure:

Step 1: To a solution of compound 6 in DCM is added a solution of oxalyl chloride (2 eq.) and few drops of DMF. The reaction mixture is stirred for 1 to 2 hours at room temperature and evaporated in vacuo to yield the acid chloride used as crude.

Step 2: To a mixture of acid chloride in DCM is added the amine $R_2NHR_3$ (1.1 to 3 eq.) and a base such as triethylamine or diisopropylamine (1.1 to 3 eq.). The reaction is stirred at room temperature until completion (microwaves at 150° C. for 20 minutes in DCE is used for amines with low reactivity). The crude is purified by flash chromatography on silica gel to yield the amide 7.

Step 3: The amide 7 is deprotected in solvents such as methanol, THF or dioxane using an aqueous solution of inorganic base such as sodium hydroxide or potassium hydroxide (10 to 20 eq.) at temperature ranging from 20 to 60° C. to give the alcohol 8.

Step 4: To the alcohol 8 in pyridine is added a cyclic anhydride and DMAP (3 to 10 equivalents). The reaction mixture is heated at temperature ranging from 90 to 140° C. until completion to yield after standard acidic aqueous work up and purification by flash chromatography on silica gel the acid 9.

3β-O-(3',3'-Dimethylsuccinyl)-21-oxolup-18-en-28-oic acid N-benzylamide 9-1

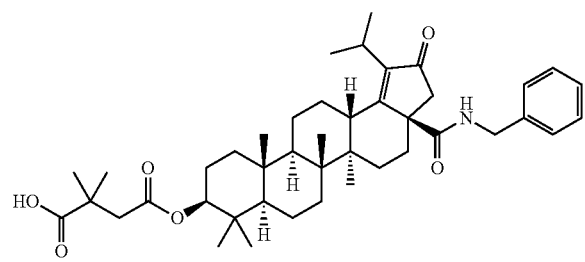

Step 1: To a solution of compound 6 (500 mg, 0.975 mmol) in 5 mL of anhydrous DCM is added a solution of oxalyl chloride (2M in DCM, 0.975 mL, 1.95 mmol) and 2 drops of DMF. The reaction mixture is stirred for 1 hour at room temperature and evaporated in vacuo to yield 3β-acetoxy-21-oxolup-18-en-28-oic acid chloride as an orange solid used as crude material.

Step 2: To a solution of previously prepared 3β-acetoxy-21-oxolup-18-en-28-oic acid chloride in 5 mL of anhydrous DCM is added triethylamine (150 μL, 1.073 mmol) and benzylamine (112 μL, 1.024 mmol). The reaction mixture is stirred at room temperature until completion, diluted with DCM, washed with HCl 1N and dried over sodium sulfate. The crude is purified by flash chromatography (Biotage) on silica gel (ethyl acetate/hexanes 0 to 50%) to yield 3β-acetoxy-21-oxolup-18-en-28-oic acid N-benzylamide 7-1 (574 mg, 98%) as a colorless solid.

1H NMR (400 MHz, CDCl$_3$): δ [ppm] 7.34-7.21 (m, 5H), 5.61 (m, 1H), 4.59 (dxd, 1H), 4.46 (dxd, 1H), 4.19 (dxd, 1H), 3.20 (sept., 1H), 2.65-2.54 (m, 2H), 2.46 (d, 1H), 2.17 (d, 1H), 2.03 (s, 3H), 1.88-0.82 (m, 16H), 1.20 (d, 3H), 1.18 (d, 3H), 0.90 (br s, 6H), 0.88 (s, 3H), 0.84 (s, 3H), 0.83 (s, 3H), 0.77 (m, 1H).

Step 3: To a solution of 3β-acetoxy-21-oxolup-18-en-28-oic acid N-benzylamide (574 mg, 0.953 mmol) in a 4:1 mixture of dioxane/water (25 mL) is added an aqueous solution of 4N NaOH (2.38 mL). The mixture is stirred for 4 hours at 50° C., then HCl 4N (2.38 mL) is added and dioxane is evaporated in vacuo. The remaining aqueous solution is extracted with ethyl acetate (3x) and the combined organic layers are washed with brine, dried over sodium sulfate, filtered and concentrated. The crude material is purified by flash chromatography (Biotage) on silica gel (ethyl acetate/hexanes 0 to 80%) to isolate 3β-hydroxy-21-oxolup-18-en-28-oic acid N-benzylamide 8-1 (307 mg, 58%) as a white solid.

1H NMR (400 MHz, CDCl$_3$): δ [ppm] 7.34-7.21 (m, 5H), 5.62 (m, 1H), 4.59 (dxd, 1H), 4.20 (dxd, 1H), 3.19 (sept., 2H), 2.65-2.55 (m, 2H), 2.46 (d, 1H), 2.16 (d, 1H), 1.88-0.82 (m, 16H), 1.20 (d, 3H), 1.17 (d, 3H), 0.95 (s, 3H), 0.90 (s, 3H), 0.88 (s, 3H), 0.85 (s, 3H), 0.75 (s, 3H), 0.67 (m, 1H).

Step 4: To a solution of 3β-hydroxy-21-oxolup-18-en-28-oic acid N-benzylamide (110 mg, 0.196 mmol) in 3 mL of pyridine is added 2,2-dimethyl succinic anhydride (75.3 mg, 0.588 mmol) and DMAP (28.6 mg, 0.235 mmol). The reaction mixture is stirred overnight under reflux. Then 75.3 mg of 2,2-dimethyl succinic anhydride is added twice every 3 hours to complete the reaction. The solvent is evaporated in vacuo and the residue is taken up with ethyl acetate (50 mL) and HCl 1N (10 mL). The organic layer is washed with water (2×30 mL), brine (30 mL) and dried over sodium sulfate. The crude material is purified by flash chromatography (Biotage) on silica gel (ethyl acetate/hexanes 0 to 50%) to give the title compound 9-1 (118.6 mg, 88%) as a colorless solid.

1H NMR (400 MHz, CDCl$_3$): δ [ppm] 7.34-7.21 (m, 5H), 5.61 (dxd, 1H), 4.59 (dxd, 1H), 4.50 (dxd, 1H), 4.20 (dxd, 1H), 3.19 (sept., 1H), 2.67 (d, 1H), 2.65-2.54 (m, 2H), 2.56 (d, 1H), 2.45 (d, 1H), 2.17 (1H), 1.85-0.74 (m, 18H), 1.3 (s, 3H), 1.29 (s, 3H), 1.2 (d, 3H), 1.18 (d, 3H), 0.89 (br s, 6H), 0.86 (s, 3H), 0.82 (s, 3H), 0.8 (s, 3H). LC/MS: m/z=688.68 (M+H$^{30}$).

The compounds of the present invention wherein Y is C(O) can be prepared as generally described in schemes 3 or 4.

Scheme 3

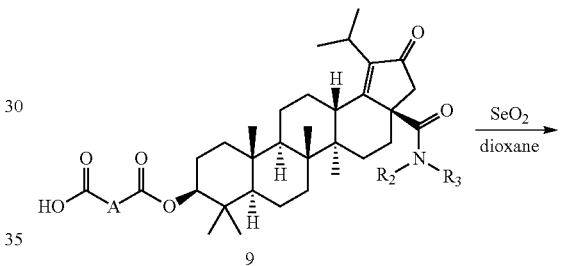

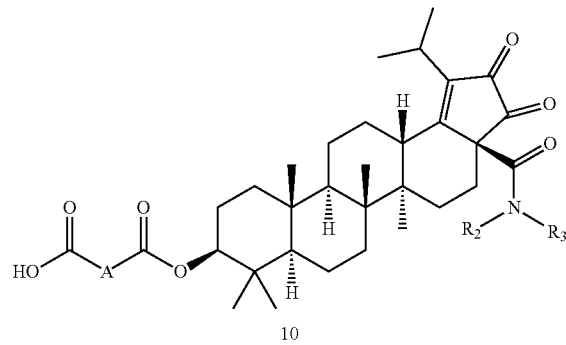

General Procedure:

Selenium dioxide (4 to 6 eq.) is added to a solution of compound 9 previously dissolved in dioxane, acetic acid and acetic anhydride. The reaction mixture is refluxed overnight, then cooled to room temperature and filtered through Celite. The residue is dissolved in DCM, washed with water, brine, dried over sodium sulfate and evaporated to dryness. The crude material is purified by flash chromatography on silica gel to yield the compound 10.

Scheme 4

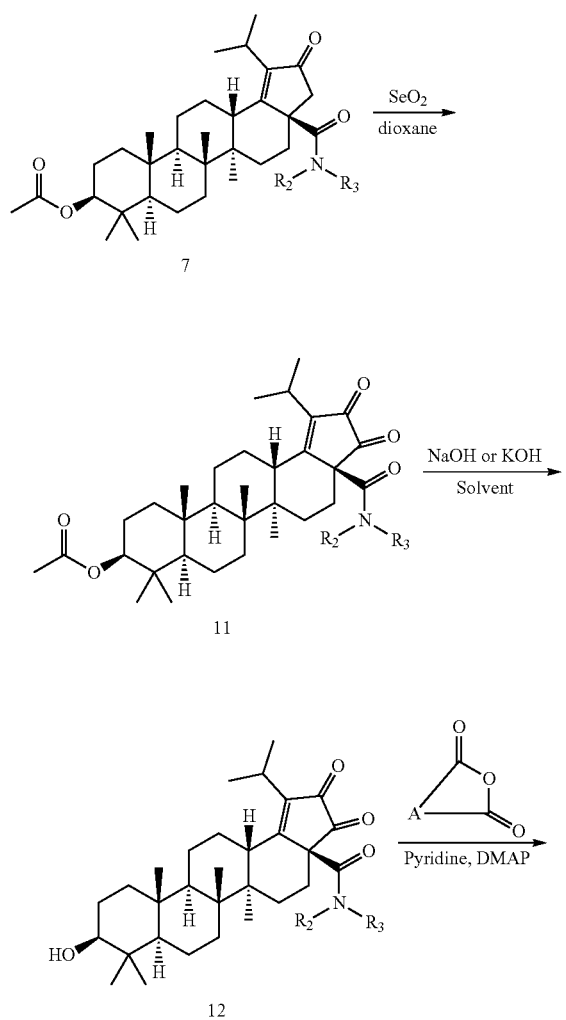

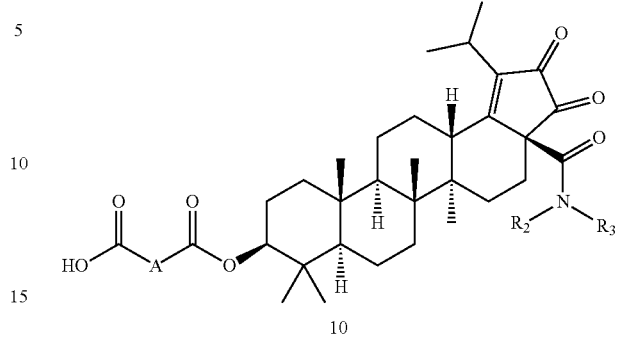

General Procedure:

Step 1: Selenium dioxide (4 to 6 eq.) is added to a solution of compound 7 previously dissolved in dioxane, acetic acid and acetic anhydride. The reaction mixture is refluxed overnight, then cooled to room temperature and filtered through Celite. The residue is dissolved in DCM, washed with water, brine, dried over sodium sulfate and evaporated to dryness. The crude material is purified by flash chromatography on silica gel to yield the compound 11.

Step 2: The ester 11 is deprotected in solvents such as methanol, THF or dioxane using an aqueous solution of inorganic base such as sodium hydroxide or potassium hydroxide (10 to 20 eq.) at temperature ranging from 20 to 60° C. to give the alcohol 12.

Step 3: To the alcohol 12 in pyridine is added a cyclic anhydride (5 to 10 eq.) and DMAP (1.1 to 2 eq.). The reaction mixture is heated at temperature ranging from 90 to 140° C. until completion to yield after standard acidic aqueous work up and purification by flash chromatography on silica gel the acid 10.

Tables 1, 2 and 3 of compounds illustrate some of the compounds of the present invention which may be synthesized using the procedures described in scheme 2. Retention time ($t_R$) for each compound are measured using the standard analytical HPLC or LC/MS methods described above.

TABLE 1

| Cpd # | Structure | Compound name |
|---|---|---|
| 7-2 | (structure) | 3β-O-Acetoxy-21-oxolup-18-en-28-oic acid N-methylamide |

TABLE 1-continued
| Cpd # | Structure | Compound name |
|---|---|---|
| 7-3 | 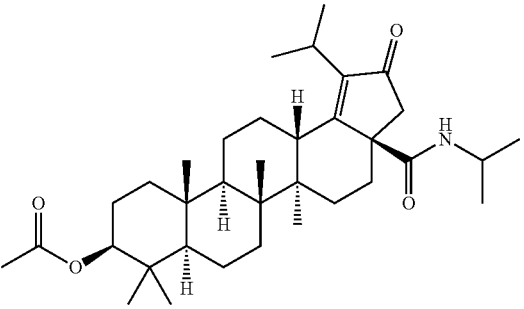 | 3β-Acetoxy-21-oxolup-18-en-28-oic acid N-isopropylamide |
| 7-4 | 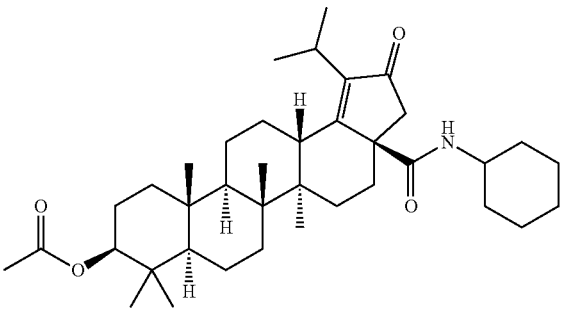 | 3β-Acetoxy-21-oxolup-18-en-28-oic acid N-cyclohexylamide |
| 7-5 | 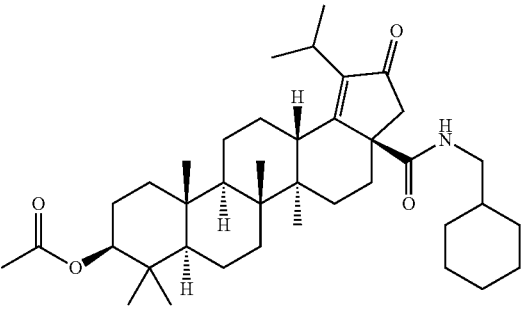 | 3β-Acetoxy-21-oxolup-18-en-28-oic acid N-cyclohexyl methylamide |
| 7-6 | 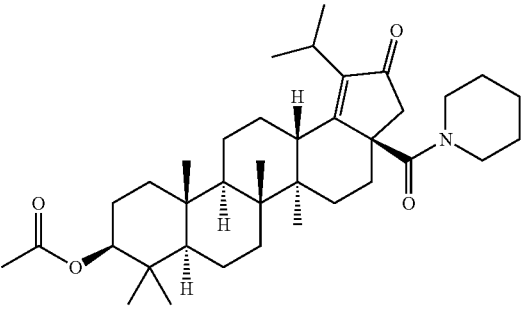 | 3β-Acetoxy-21-oxolup-18-en-28-oic acid N-piperidinyl acetamide |
| 7-7 | 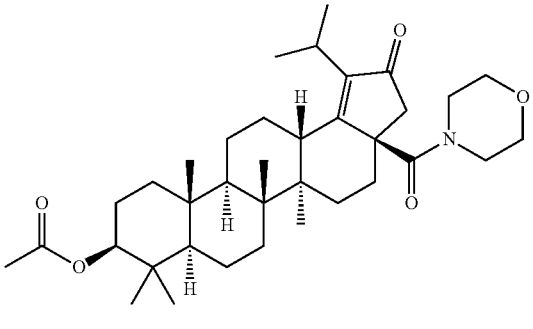 | 3β-Acetoxy-21-oxolup-18-en-28-oic acid N-morpholyl acetamide |

TABLE 1-continued

| Cpd # | Structure | Compound name |
| --- | --- | --- |
| 7-8 | 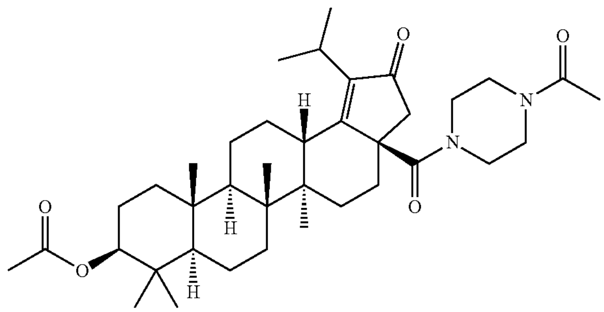 | 3β-Acetoxy-21-oxolup-18-en-28-oic acid N-(4-acetyl piperazinyl) acetamide |
| 7-9 | 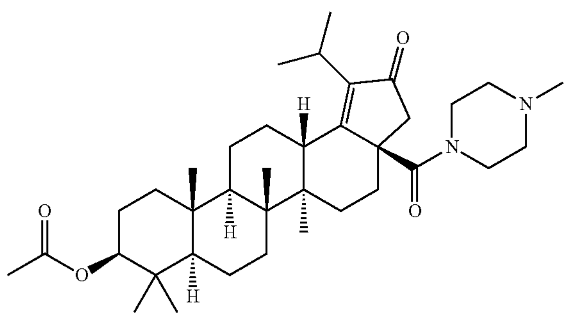 | 3β-O-Acetoxy-21-oxolup-18-en-28-oic acid N-(4-methyl piperazinyl) acetamide |
| 7-10 | 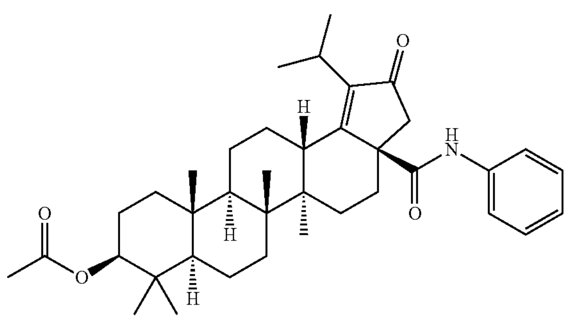 | 3β-O-Acetoxy-21-oxolup-18-en-28-oic acid N-benzamide |
| 7-11 | 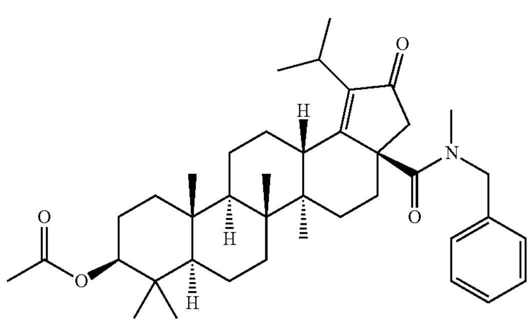 | 3β-O-Acetoxy-21-oxolup-18-en-28-oic acid N-methyl-N-benzylamide |

TABLE 1-continued

| Cpd # | Structure | Compound name |
|---|---|---|
| 7-12 | 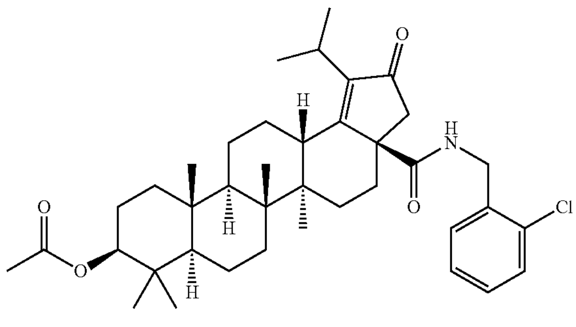 | 3β-O-Acetoxy-21-oxolup-18-en-28-oic acid N-2-chloro-benzylamide |
| 7-13 | 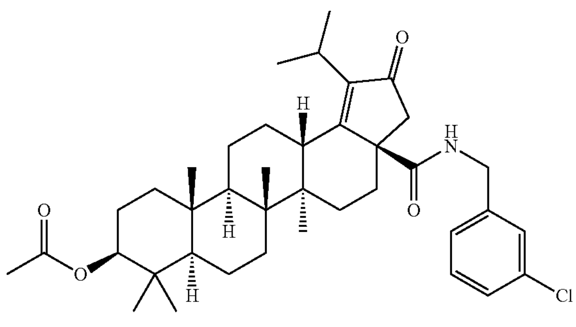 | 3β-O-Acetoxy-21-oxolup-18-en-28-oic acid N-3-chloro-benzylamide |
| 7-14 | 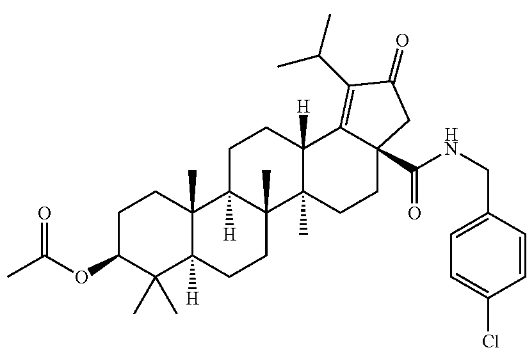 | 3β-O-Acetoxy-21-oxolup-18-en-28-oic acid N-4-chloro-benzylamide |
| 7-15 | 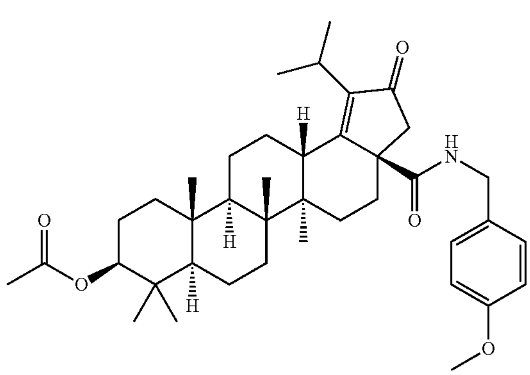 | 3β-O-Acetoxy-21-oxolup-18-en-28-oic acid N-4-methoxy-benzylamide |

TABLE 1-continued
| Cpd # | Structure | Compound name |
|---|---|---|
| 7-16 | 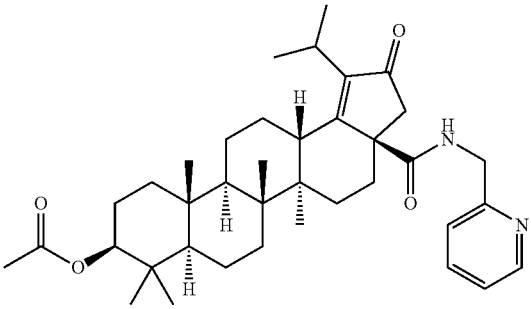 | 3β-O-Acetoxy-21-oxolup-18-en-28-oic acid N-pyridin-2-ylmethylamide |
| 7-17 | 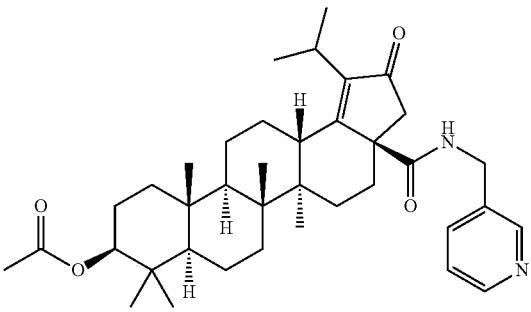 | 3β-O-Acetoxy-21-oxolup-18-en-28-oic acid N-pyridin-3-ylmethylamide |
| 7-18 | 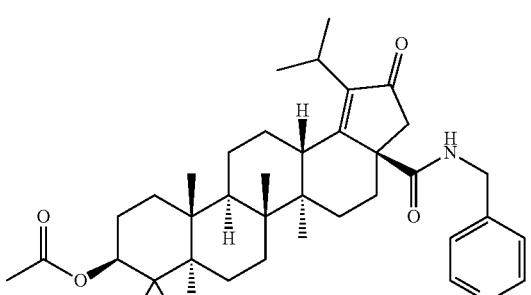 | 3β-O-Acetoxy-21-oxolup-18-en-28-oic acid N-pyridin-4-ylmethylamide |
| 7-19 | 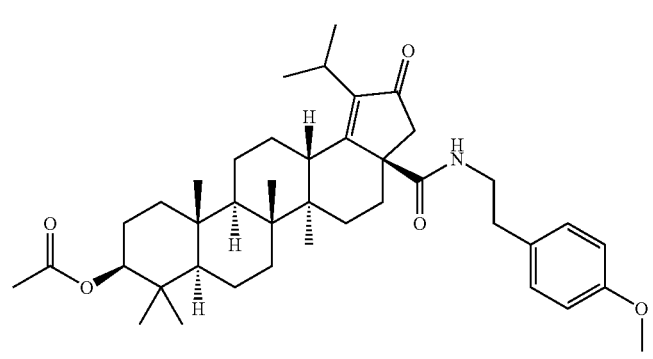 | 3β-O-Acetoxy-21-oxolup-18-en-28-oic acid N-[2-(4-methoxy-phenyl)-ethyl]-acetamide |

TABLE 1-continued

| Cpd # | Structure | Compound name |
|---|---|---|
| 7-20 | 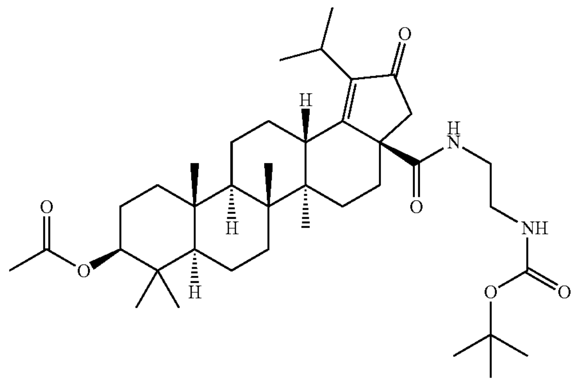 | 3β-O-Acetoxy-21-oxolup-18-en-28-oic acid N-(2-acetylamino-ethyl)-carbamic acid tert-butyl ester |
| 7-21 | 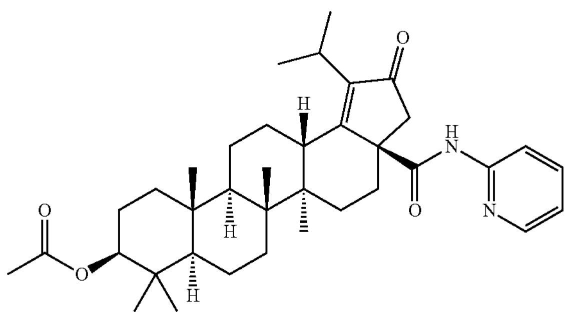 | 3β-O-Acetoxy-21-oxolup-18-en-28-oic acid N-pyridin-2-yl-acetamide |
| 7-22 | 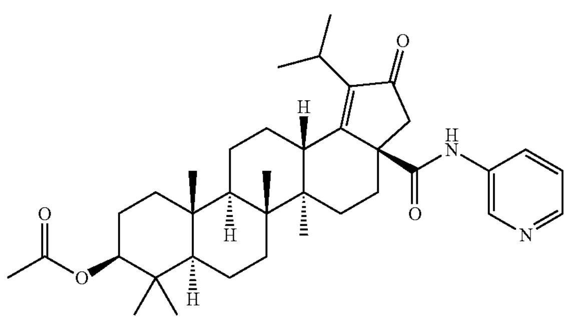 | 3β-O-Acetoxy-21-oxolup-18-en-28-oic acid N-pyridin-3-yl-acetamide |
| 7-23 | 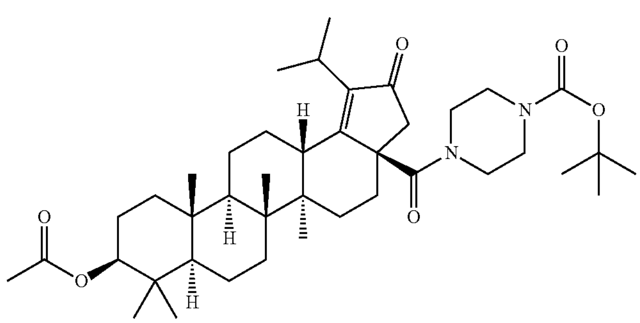 | 3β-O-Acetoxy-21-oxolup-18-en-28-oic acid N-1-acetyl-piperazine-4-carboxylic acid tert-butyl ester |

TABLE 1-continued

| Cpd # | Structure | Compound name |
|---|---|---|
| 7-24 | 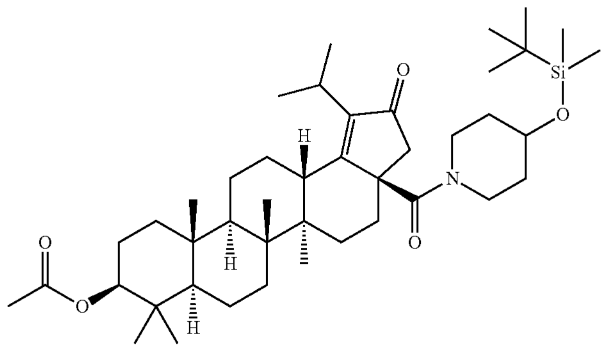 | 3β-O-Acetoxy-21-oxolup-18-en-28-oic acid N-1-(4-tert-butyl-dimethyl-silanyloxy-piperidin-1-yl)-acetamide |
| 7-25 | 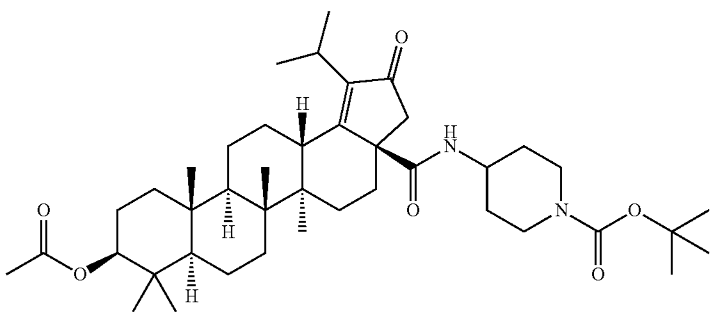 | 3β-O-Acetoxy-21-oxolup-18-en-28-oic acid N-1-acetylamino-piperidine-4-carboxylic acid tert-butyl ester |
| 7-26 | 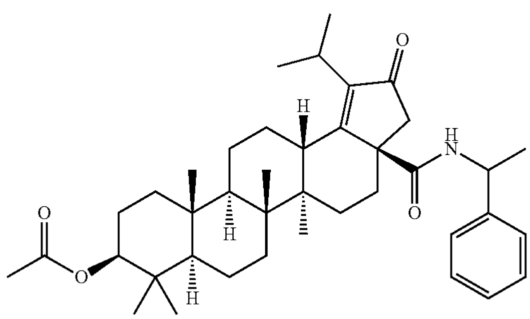 | 3β-O-Acetoxy-21-oxolup-18-en-28-oic acid N-(1-phenyl-ethyl)-acetamide |
| 7-27 | 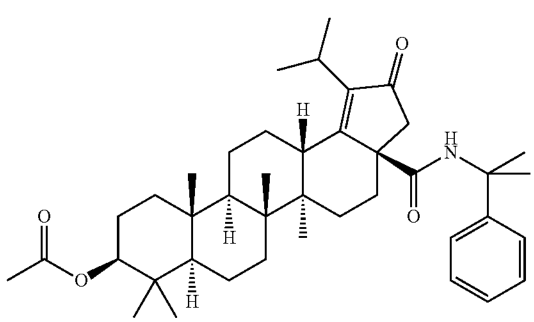 | 3β-O-Acetoxy-21-oxolup-18-en-28-oic acid N-(1-methyl-1-phenyl-ethyl)-acetamide |

TABLE 1-continued

| Cpd # | Structure | Compound name |
|---|---|---|
| 7-28 | 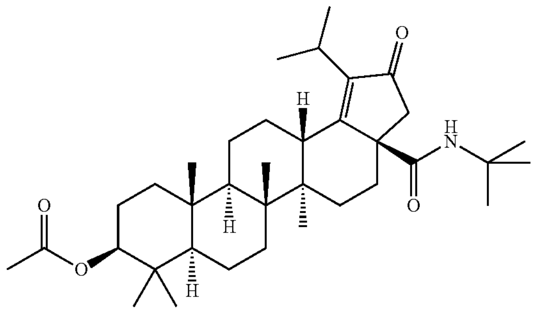 | 3β-O-Acetoxy-21-oxolup-18-en-28-oic acid N-(tert-butyl)-acetamide |
| 7-29 | 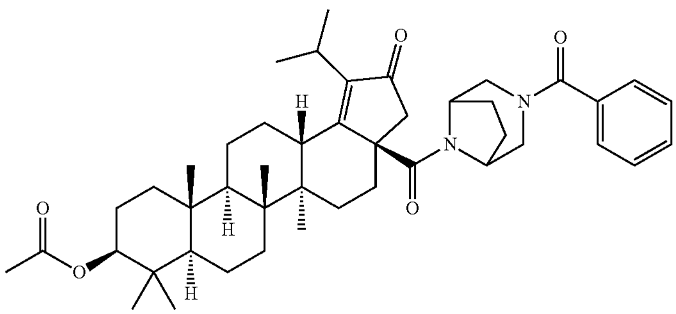 | 3β-O-Acetoxy-21-oxolup-18-en-28-oic acid N-(8-amino-3,8-diaza-bicyclo[3.2.1]octane-3-benzamide)-acetamide |
| 7-30 | 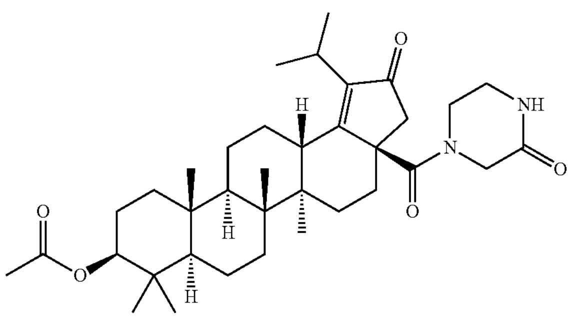 | 3β-O-Acetoxy-21-oxolup-18-en-28-oic acid N-4-piperazi-2-one-acetamide |
| 7-31 | 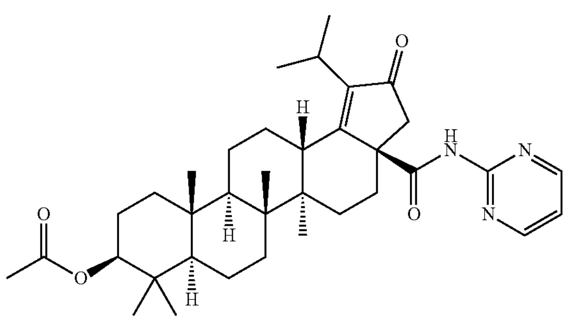 | 3β-O-Acetoxy-21-oxolup-18-en-28-oic acid N-pyrimidin-2-yl-acetamide |
| 7-32 | 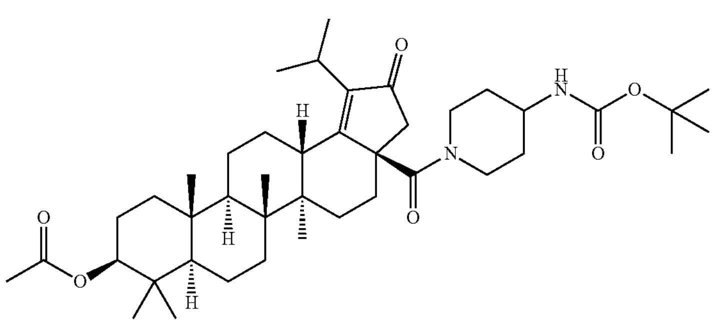 | 3β-O-Acetoxy-21-oxolup-18-en-28-oic acid N-(4-amino carboxylic acid tert-butyl-ester-1-piperidine)-acetamide |

TABLE 1-continued

| Cpd # | Structure | Compound name |
|---|---|---|
| 7-33 | 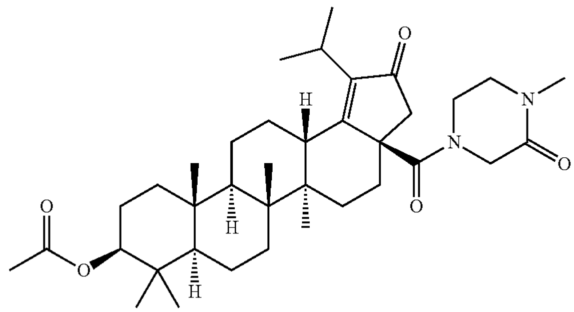 | 3β-O-Acetoxy-21-oxolup-18-en-28-oic acid N-4-(1-methyl-piperazi-2-one)-acetamide<br>LC/MS: 7.92 min.<br>(Method b)<br>M + H+ 609.43 |
| 7-34 | 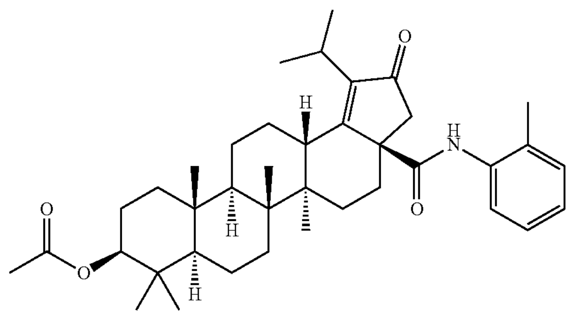 | 3β-O-Acetoxy-21-oxolup-18-en-28-oic acid N-2-methyl-phen-1-yl acetamide |
| 7-35 | 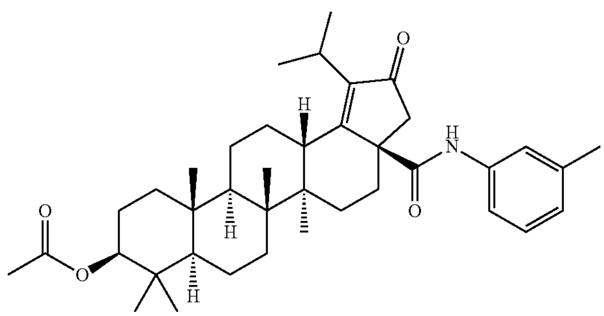 | 3β-O-Acetoxy-21-oxolup-18-en-28-oic acid N-3-methyl-phen-1-yl acetamide |
| 7-36 | 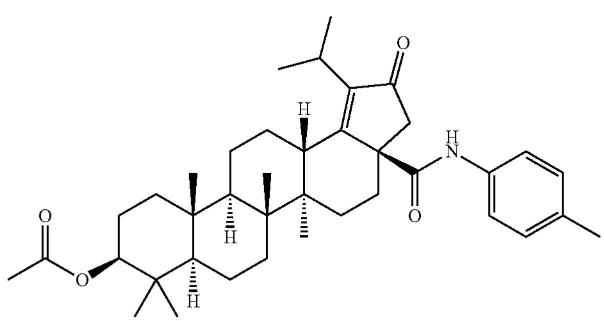 | 3β-O-Acetoxy-21-oxolup-18-en-28-oic acid N-4-methyl-phen-1-yl acetamide |
| 7-37 | 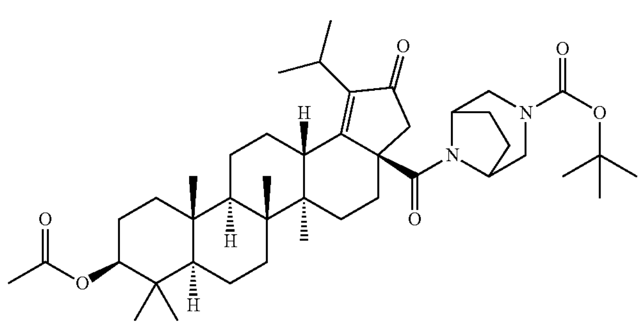 | 3β-O-Acetoxy-21-oxolup-18-en-28-oic acid N-8-acetylamino-3,8-diaza-bicyclo[3.2.1]octane-3-carboxylic acid tert-butyl ester |

TABLE 1-continued

| Cpd # | Structure | Compound name |
|---|---|---|
| 7-38 | 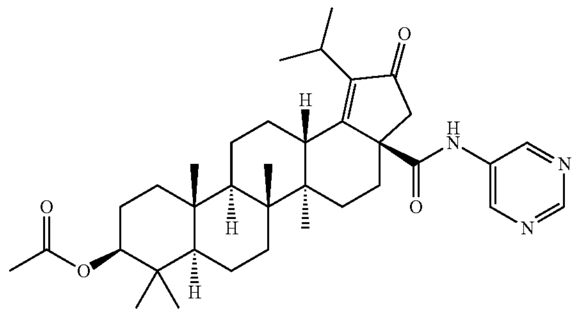 | 3β-O-Acetoxy-21-oxolup-18-en-28-oic acid N-pyrimidin-5-yl-acetamide<br>LC/MS: 10.12 min.<br>(Method b)<br>M + H$^+$ 590.35 |
| 7-39 | 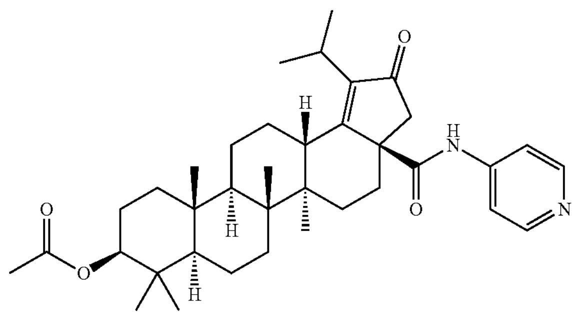 | 3β-O-Acetoxy-21-oxolup-18-en-28-oic acid N-pyridin-4-yl-acetamide<br>LC/MS: 11.63 min.<br>(Method a)<br>M + H$^+$ 589.4 |
| 7-40 | 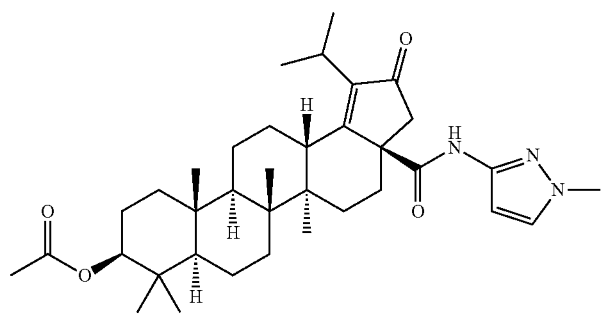 | 3β-O-Acetoxy-21-oxolup-18-en-28-oic acid N-3-amino-1-methyl-1H-pyrazole-acetamide<br>LC/MS: 10.29 min.<br>(Method b)<br>M + H$^+$ 592.42 |
| 7-41 | 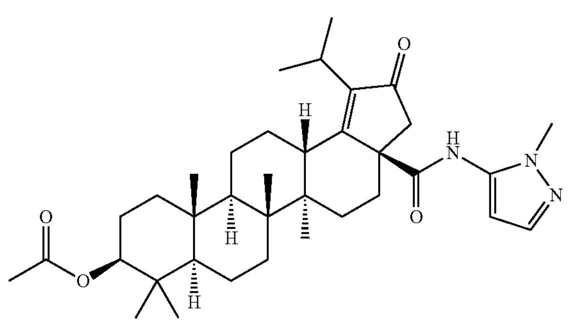 | 3β-O-Acetoxy-21-oxolup-18-en-28-oic acid N-5-amino-1-methyl-1H-pyrazole-acetamide<br>LC/MS: 9.44 min.<br>(Method b)<br>M + H$^+$ 592.41 |

| Cpd # | Structure | Compound name |
|---|---|---|
| 7-42 | 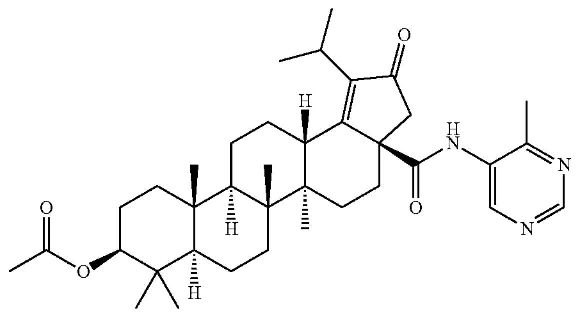 | 3β-O-Acetoxy-21-oxolup-18-en-28-oic acid N-4-methyl-pyrimidin-5-yl-acetamide |
| 7-43 | 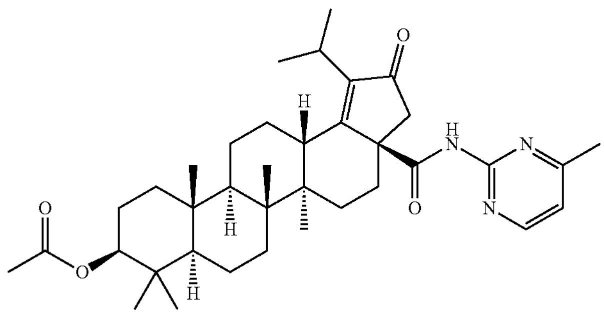 | 3β-O-Acetoxy-21-oxolup-18-en-28-oic acid N-4-methyl-pyrimidin-2-yl-acetamide |
| 7-44 | 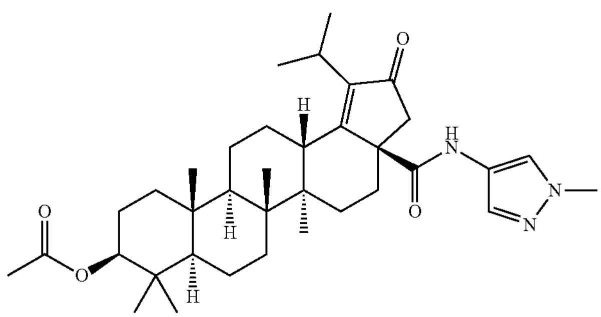 | 3β-O-Acetoxy-21-oxolup-18-en-28-oic acid N-4-amino-1-methyl-1H-pyrazole-acetamide |
| 7-45 | 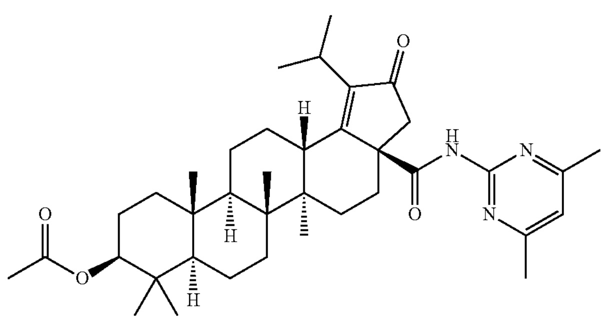 | 3β-O-Acetoxy-21-oxolup-18-en-28-oic acid N-4,6-dimethyl-pyrimidin-2-yl-acetamide |
| 7-46 | 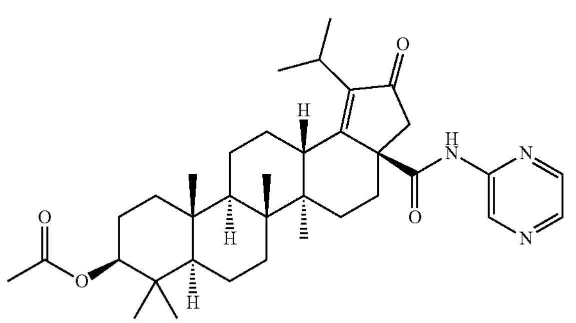 | 3β-O-Acetoxy-21-oxolup-18-en-28-oic acid N-pyrazin-2-yl-acetamide<br>LC/MS: 11.71 min.<br>(Method b)<br>M + H⁺ 590. |

TABLE 1-continued

| Cpd # | Structure | Compound name |
|---|---|---|
| 7-47 | 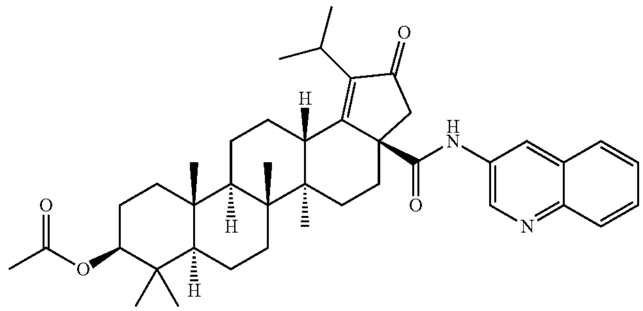 | 3β-O-Acetoxy-21-oxolup-18-en-28-oic acid N-quinolin-3-yl-acetamide<br>LC/MS: 11.15 min.<br>(Method b)<br>M + H⁺ 639.47 |
| 7-48 | 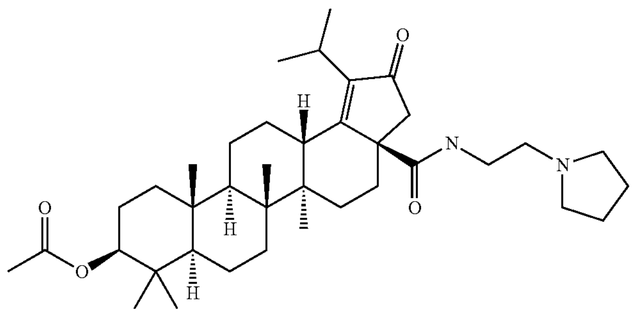 | 3β-O-Acetoxy-21-oxolup-18-en-28-oic acid N-(2-pyrrolidin-1-yl-ethyl)-acetamide<br>LC/MS: 11.19 min.<br>(Method a)<br>M + H⁺ 609.4 |
| 7-49 | 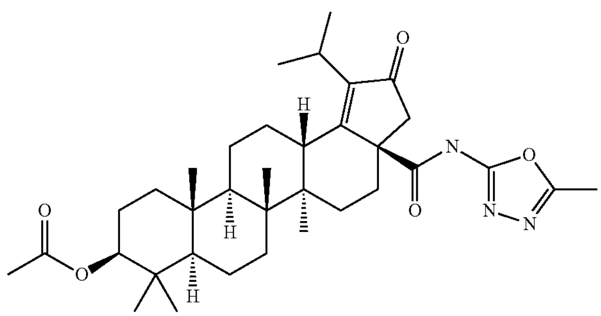 | Acetoxy-21-oxolup-18-en-28-oic acid N-(5-methyl-[1,3,4]oxadiazol-2-yl)-acetamide<br>LC/MS: 16.26 min.<br>(Method a)<br>M + H⁺ 594.22 |
| 7-50 | 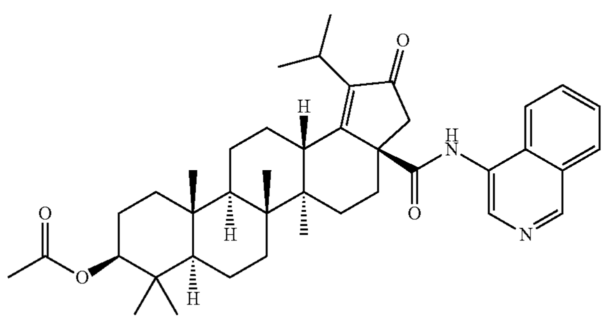 | 3β-O-Acetoxy-21-oxolup-18-en-28-oic acid N-isoquinolin-4-yl-acetamide<br>LC/MS: 15.26 min.<br>(Method a)<br>M + H⁺ 639.44 |
| 7-51 | 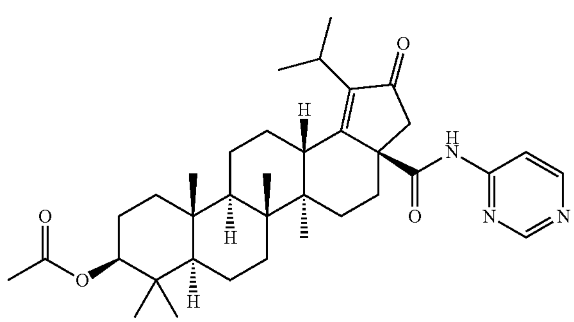 | 3β-O-Acetoxy-21-oxolup-18-en-28-oic acid N-pyrimidin-4-yl-acetamide |

TABLE 1-continued

| Cpd # | Structure | Compound name |
|---|---|---|
| 7-52 | 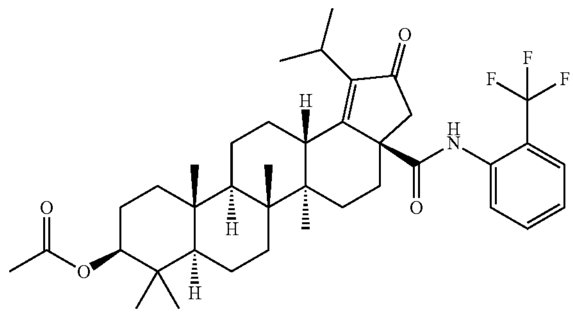 | 3β-O-Acetoxy-21-oxolup-18-en-28-oic acid N-2-trifluoromethyl-phen-1-yl acetamide<br>LC/MS: 15.87 min.<br>(Method b)<br>M + H⁺ 656.56 |
| 7-53 | 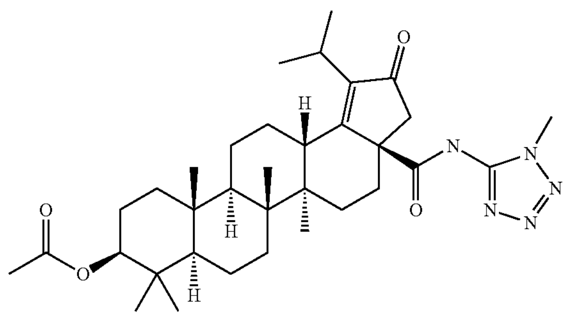 | 3β-O-Acetoxy-21-oxolup-18-en-28-oic acid N-(1-methyl-1H-tetrazol-5-yl)-acetamide<br>LC/MS: 17.22 min.<br>(Method a)<br>M + H⁺ 594.34 |
| 7-54 | 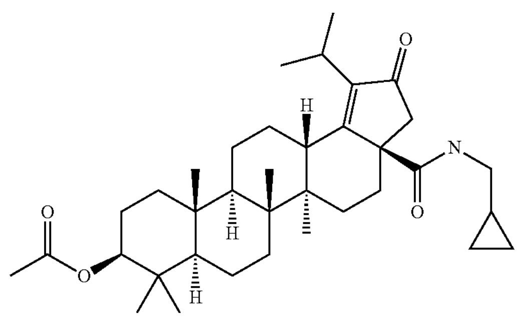 | 3β-O-Acetoxy-21-oxolup-18-en-28-oic acid N-cyclopropylmethyl acetamide<br>LC/MS: 12 min.<br>(Method b)<br>M+ 565.84 |
| 7-55 | 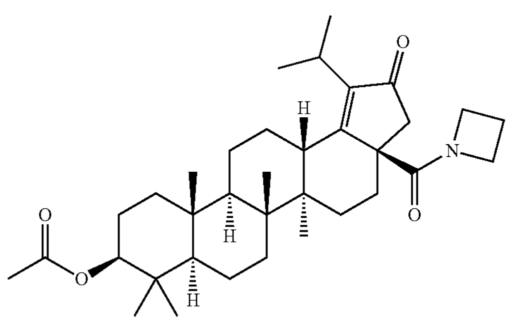 | 3β-O-Acetoxy-21-oxolup-18-en-28-oic acid N-azetidine-1-acetamide<br>LC/MS: 9.61 min.<br>(Method b)<br>M + H⁺ 552.37 |
| 7-56 | 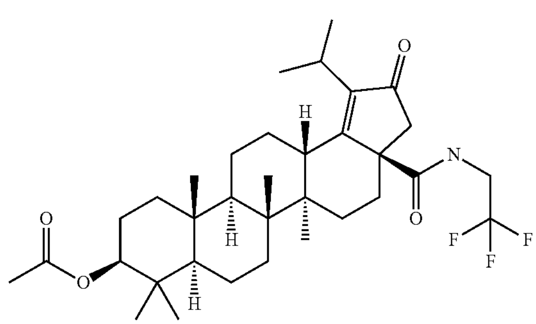 | 3β-O-Acetoxy-21-oxolup-18-en-28-oic acid N-(2,2,2-trifluoro-ethyl)-acetamide<br>LC/MS: 12.35 min.<br>(Method b)<br>M + H⁺ 594.45 |

TABLE 1-continued

| Cpd # | Structure | Compound name |
|---|---|---|
| 7-57 | 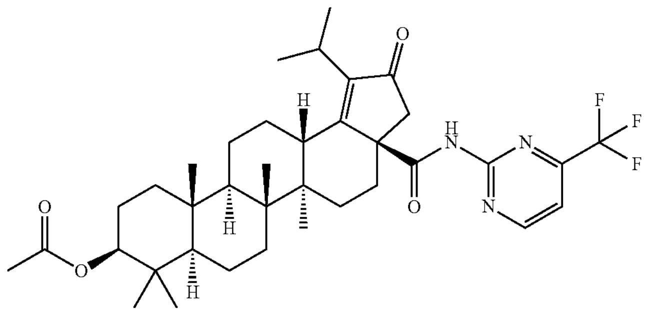 | 3β-O-Acetoxy-21-oxolup-18-en-28-oic acid N-4-trifluoro-pyrimidin-2-yl-acetamide<br>LC/MS: 19.21 min.<br>(Method a)<br>M + H⁺ 658.68 |
| 7-58 | 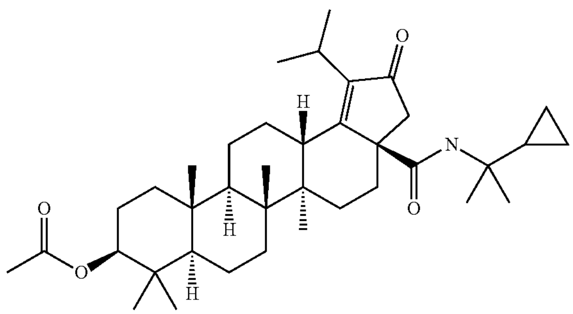 | 3β-O-Acetoxy-21-oxolup-18-en-28-oic acid N-(1-cyclopropyl-1-methyl-ethyl)-acetamide<br>LC/MS: 15.38 min.<br>(Method b)<br>M + H⁺ 594.5 |
| 7-59 | 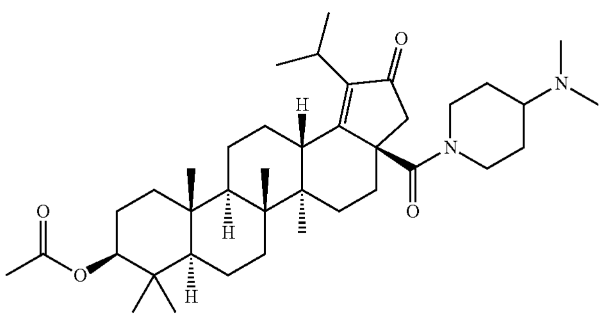 | 3β-O-Acetoxy-21-oxolup-18-en-28-oic acid N-(4-dimethylamino-piperidin-1-yl)-acetamide<br>LC/MS: 10.83 min.<br>(Method a)<br>M + H⁺ 623.65 |
| 7-60 | 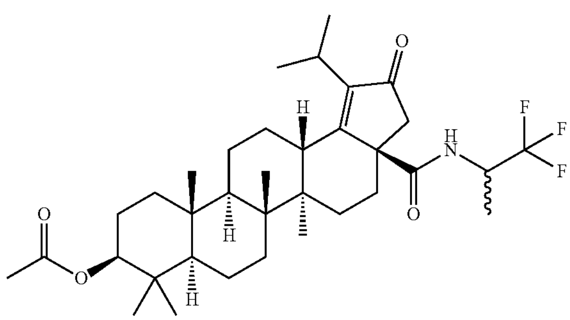 | 3β-O-Acetoxy-21-oxolup-18-en-28-oic acid N-(2,2,2-trifluoro-1-methyl-ethyl)-acetamide<br>LC/MS: 19.84 min.<br>(Method a)<br>M + H⁺ 608.5 |
| 7-61 | 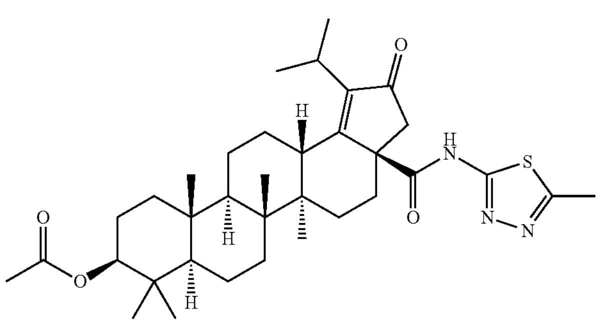 | 3β-O-Acetoxy-21-oxolup-18-en-28-oic acid N-(5-methyl-[1,3,4]thiadiazol-2-yl)-acetamide<br>LC/MS: 18 min.<br>(Method a)<br>M + H⁺ 610.47 |

TABLE 1-continued

| Cpd # | Structure | Compound name |
|---|---|---|
| 7-62 | 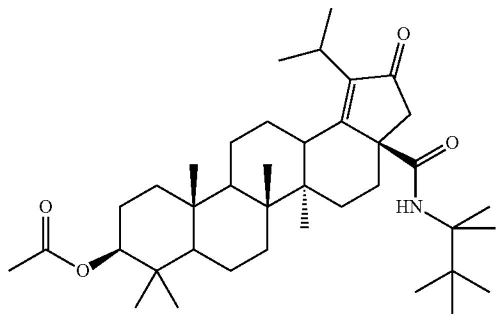 | 3β-O-Acetoxy-21-oxolup-18-en-28-oic acid N-(2,2,2-trifluoro-1,1-dimethyl-ethyl)-acetamide<br>LC/MS: 15.04 min.<br>(Method b)<br>M + H⁺ 622.54 |
| 7-63 | 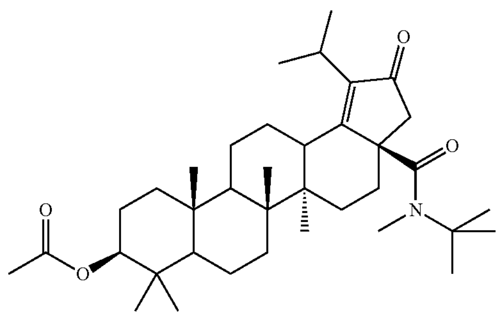 | 3β-O-Acetoxy-21-oxolup-18-en-28-oic acid N-tert-butyl-N-methyl-acetamide<br>LC/MS: 15.07 min.<br>(Method b)<br>M + H⁺ 582.47 |
| 7-64 | 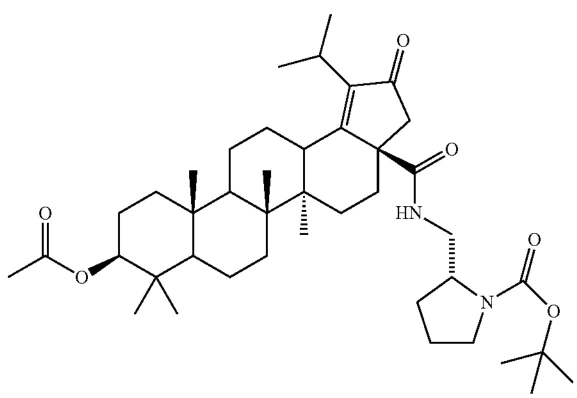 | 3β-O-Acetoxy-21-oxolup-18-en-28-oic acid N-(R)-2-acetylaminomethyl-pyrrolidine-1-carboxylic acid tert-butyl ester |
| 7-65 | 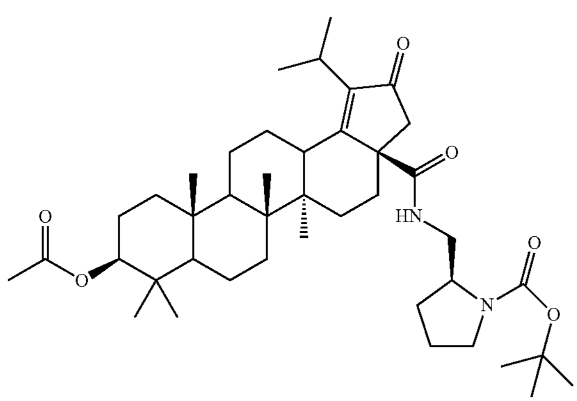 | 3β-O-Acetoxy-21-oxolup-18-en-28-oic acid N-(S)-2-acetylaminomethyl-pyrrolidine-1-carboxylic acid tert-butyl ester |

TABLE 1-continued

| Cpd # | Structure | Compound name |
|---|---|---|
| 7-66 | 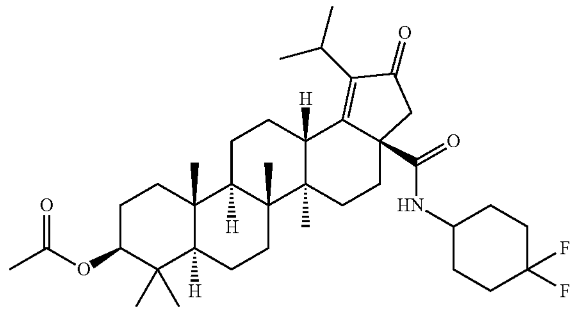 | 3β-O-Acetoxy-21-oxolup-18-en-28-oic acid N-(4,4-difluoro-cyclohexyl) acetamide<br>HPLC: 30.02 min. (B)<br>LC/MS: M + H$^+$ 630.65 |
| 7-67 | 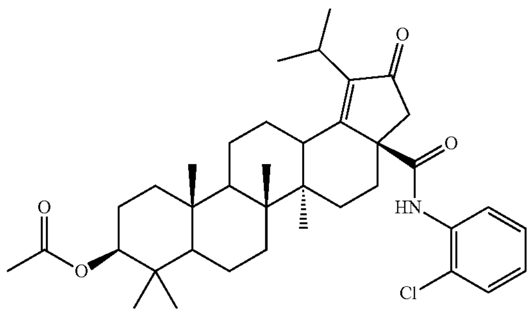 | 3β-O-Acetoxy-21-oxolup-18-en-28-oic acid N-2-chloro-phen-1-yl acetamide |
| 7-68 | 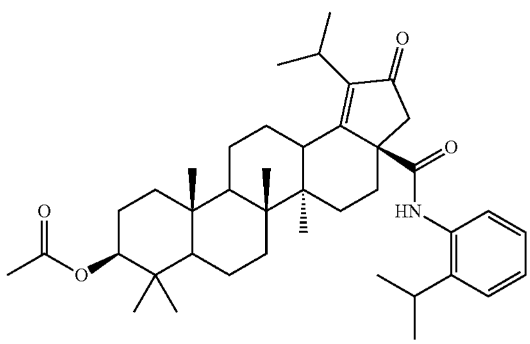 | 3β-O-Acetoxy-21-oxolup-18-en-28-oic acid N-2-isopropyl-phen-1-yl acetamide |
| 7-69 | 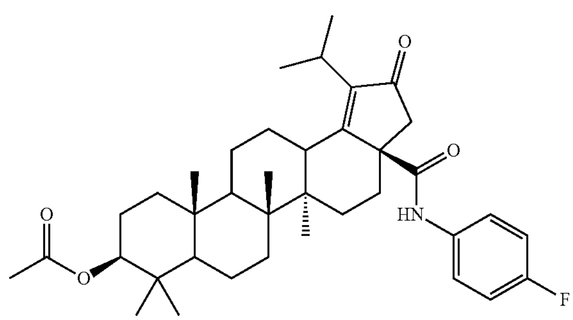 | 3β-O-Acetoxy-21-oxolup-18-en-28-oic acid N-4-fluoro-phen-1-yl acetamide |
| 7-70 | 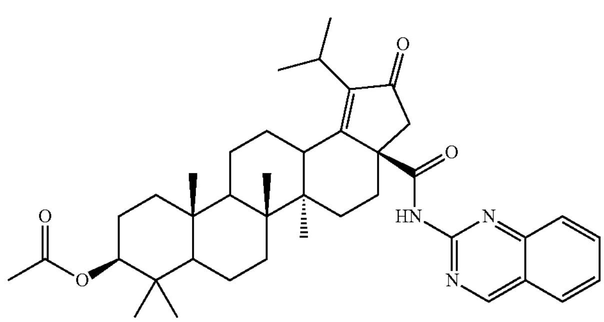 | 3β-O-Acetoxy-21-oxolup-18-en-28-oic acid N-quinazolin-2-yl acetamide |

TABLE 1-continued

| Cpd # | Structure | Compound name |
|---|---|---|
| 7-71 | 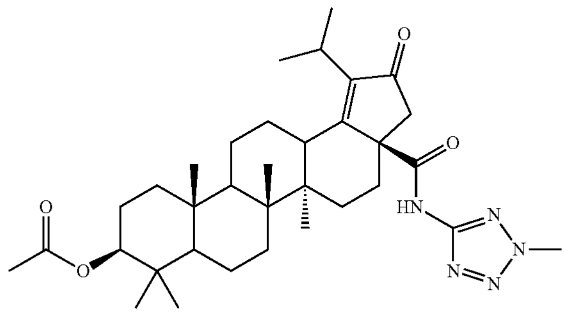 | 3β-O-Acetoxy-21-oxolup-18-en-28-oic acid N-(1-methyl-1H-tetrazol-3-yl)-acetamide |
| 7-72 | 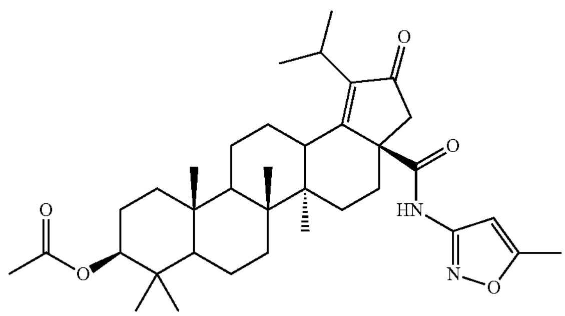 | 3β-O-Acetoxy-21-oxolup-18-en-28-oic acid N-(5-methyl-isoxazol-3-yl)-acetamide |
| 7-73 | 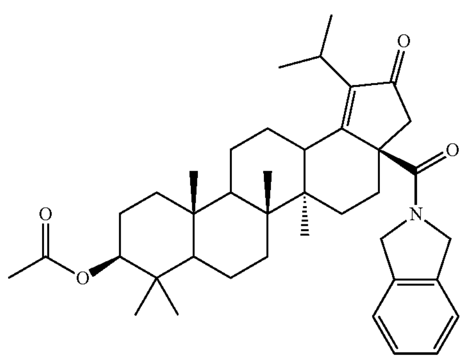 | 3β-O-Acetoxy-21-oxolup-18-en-28-oic acid N-(1,3-dihydro-isoindol-2-yl)-acetamide |
| 7-74 | 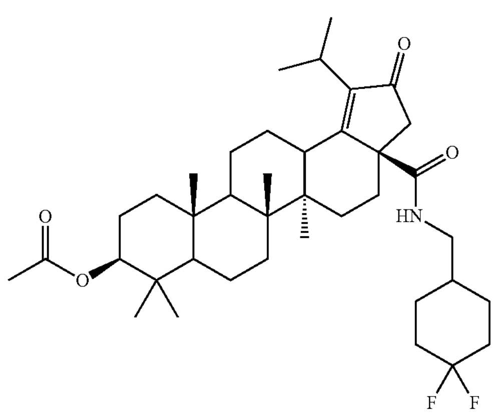 | 3β-O-Acetoxy-21-oxolup-18-en-28-oic acid N-(4,4-difluoro-cyclohexylmethyl)-acetamide<br>HPLC: 30.45 min. (B)<br>LC/MS: M + H⁺ 644.73 |

TABLE 1-continued

| Cpd # | Structure | Compound name |
|---|---|---|
| 7-75 | 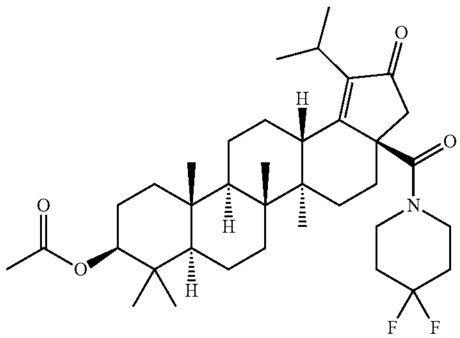 | 3β-O-Acetoxy-21-oxolup-18-en-28-oic acid N-4,4-difluoro-piperidine acetamide<br>HPLC: 31.38 min. (B)<br>LC/MS: M + H⁺ 616.58 |

TABLE 2

| Cpd # | Structure | Compound name | Analytical data |
|---|---|---|---|
| 8-2 | 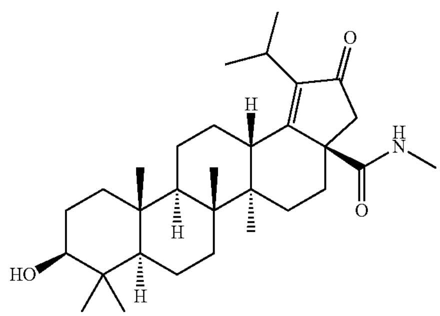 | 3β-O-Hydroxy-21-oxolup-18-en-28-oic acid N-methylamide | LC/MS: 5.84 min.<br>(Method b)<br>M + H⁺ 484.57 |
| 8-3 | 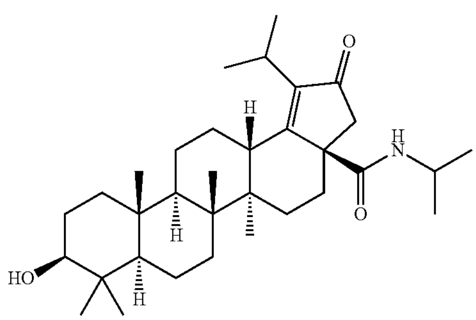 | 3β-O-Hydroxy-21-oxolup-18-en-28-oic acid N-isopropylamide | LC/MS: 8.41 min.<br>(Method b)<br>M + H⁺ 512.64 |
| 8-4 | 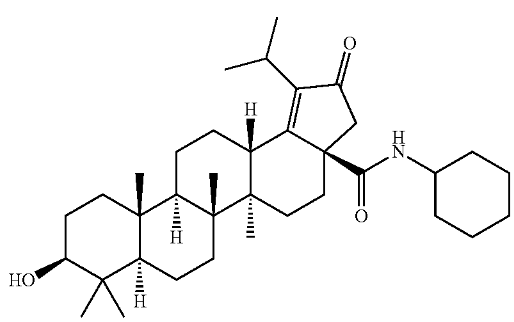 | 3β-O-Hydroxy-21-oxolup-18-en-28-oic acid N-cyclohexyl amide | LC/MS: 11.36 min.<br>(Method b)<br>M + H⁺ 552.66 |

TABLE 2-continued

| Cpd # | Structure | Compound name | Analytical data |
|---|---|---|---|
| 8-5 | 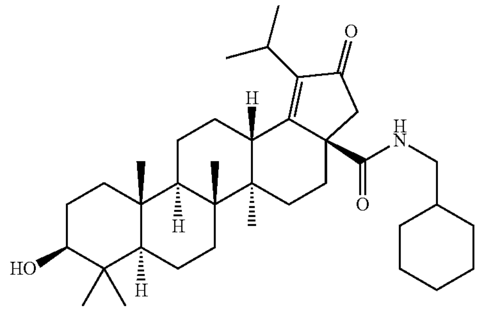 | 3β-O-Hydroxy-21-oxolup-18-en-28-oic acid N-cyclohexyl diethylamide | 1H NMR (400 MHz, CDCl$_3$): δ [ppm] 5.38 (t, 1H), 3.74 (m, 2H), 3.23 (m, 3H), 2.87 (d x d, 1H), 2.64 (m, 1H), 2.62 (m, 1H), 2.40 (d, 1H), 2.17 (d, 1H), 2.00-0.68 (m, 47H) |
| 8-6 | 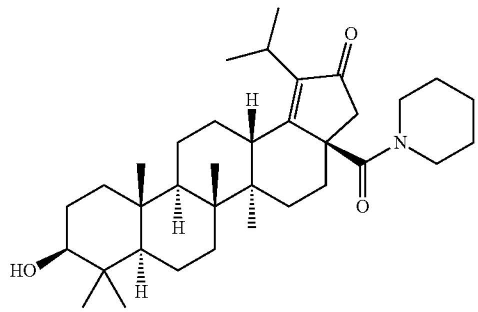 | 3β-O-Hydroxy-21-oxolup-18-en-28-oic acid N-piperidinyl acetamide | LC/MS: 10.05 min. (Method b) M + H$^+$ 538.61 |
| 8-7 | 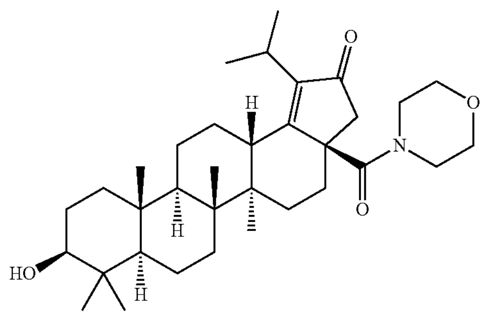 | 3β-O-Hydroxy-21-oxolup-18-en-28-oic acid N-morpholyl acetamide | LC/MS: 6.95 min. (Method b) M + H$^+$ 540.6 |
| 8-8 | 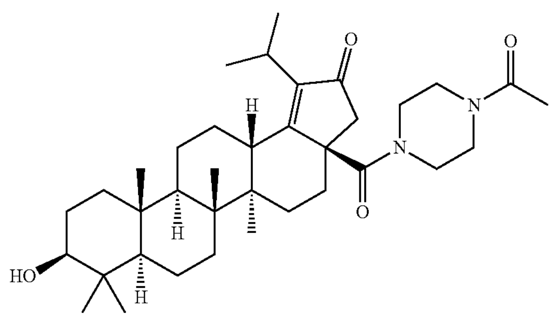 | 3β-O-Hydroxy-21-oxolup-18-en-28-oic acid N-(4-acetyl piperazinyl) acetamide | LC/MS: 4.4 min. (Method b) M + H$^+$ 581.69 |
| 8-9 | 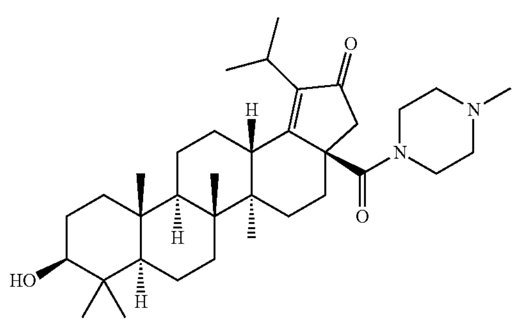 | 3β-O-Hydroxy-21-oxolup-18-en-28-oic acid N-(4-methyl piperazinyl) acetamide | LC/MS: 0.81 min. (Method b) M + H$^+$ 553.64 |

TABLE 2-continued

| Cpd # | Structure | Compound name | Analytical data |
|---|---|---|---|
| 8-10 | 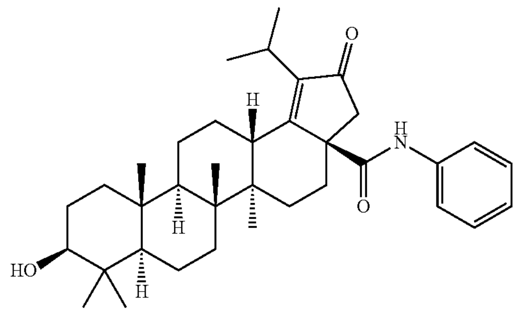 | 3β-O-Hydroxy-21-oxolup-18-en-28-oic acid N-benzamide | LC/MS: 10.92 min. (Method b) M + H⁺ 546.65 |
| 8-11 | 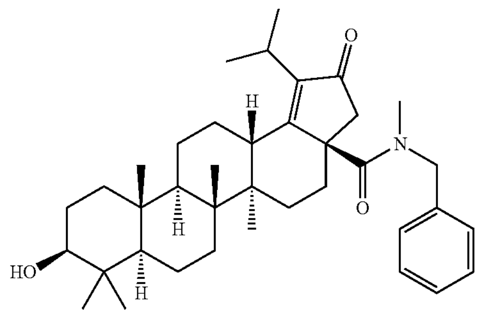 | 3β-O-Hydroxy-21-oxolup-18-en-28-oic acid N-methyl-N-benzylamide | LC/MS: 11.22 min. (Method b) M + H⁺ 574.63 |
| 8-12 | 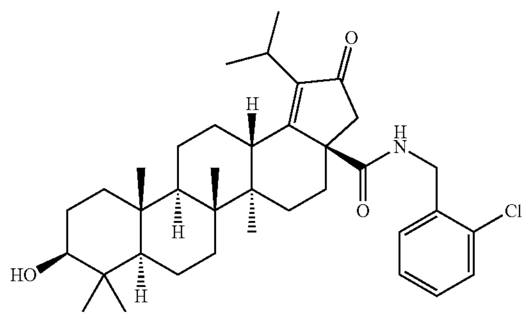 | 3β-O-Hydroxy-21-oxolup-18-en-28-oic acid N-2-chloro-benzylamide | LC/MS: 11.27 min. (Method b) M+ 594.58 |
| 8-13 | | 3β-O-Hydroxy-21-oxolup-18-en-28-oic acid N-3-chloro-benzylamide | 1H NMR (400 MHz, CDCl$_3$): δ [ppm] 7.25-7.22 (m, 3H), 7.13 (m, 1H), 5.64 (t, 1H), 4.64 (d x d, 1H), 4.10 (d x d, 1H), 3.74 (m, 1H), 3.21 (m, 2H), 2.60 (m, 2H), 2.45 (d, 1H), 2.18 (d, 1H), 1.95-0.62 (m, 36H) |
| 8-14 | 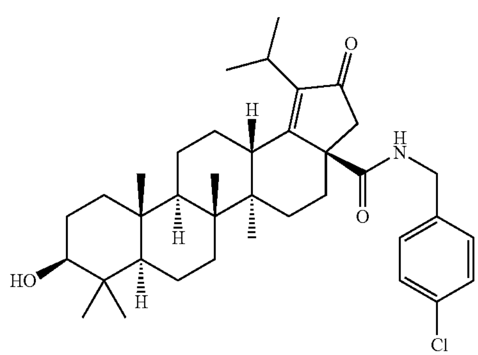 | 3β-O-Hydroxy-21-oxolup-18-en-28-oic acid N-4-chloro-benzylamide | LC/MS: 11.45 min. (Method b) M+ 594 |

TABLE 2-continued

| Cpd # | Structure | Compound name | Analytical data |
|---|---|---|---|
| 8-15 | 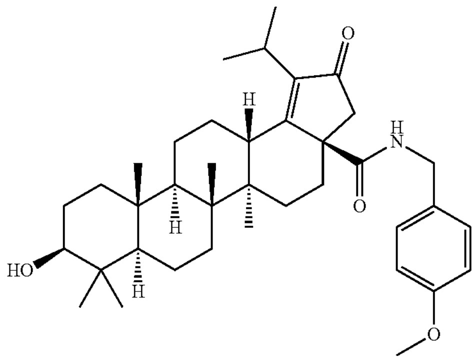 | 3β-O-Hydroxy-21-oxolup-18-en-28-oic acid N-4-methoxy-benzylamide | LC/MS: 9.26 min. (Method b) M + H⁺ 590.69 |
| 8-16 | 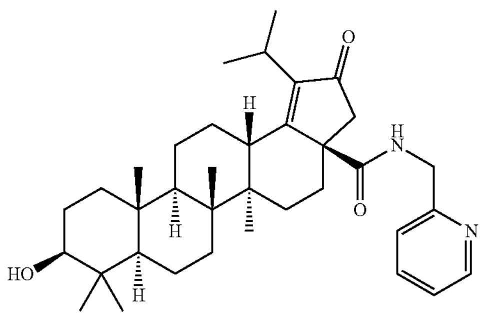 | 3β-O-Hydroxy-21-oxolup-18-en-28-oic acid N-pyridin-2-ylmethylamide | 1H NMR (400 MHz, CDCl$_3$): δ [ppm] 8.45 (m, 1H), 7.67 (t, 1H), 7.25 (m, 1H), 7.20 (m, 1H), 6.93 (br s, 1H), 4.61 (d x d, 1H), 4.39 (d x d, 1H), 3.78 (m, 1H), 3.22 (m, 2H), 2.70 (m, 2H), 2.45 (d, 1H), 2.19 (d, 1H), 2.04 (m, 1H), 1.94-0.62 (m, 36H) |
| 8-17 | 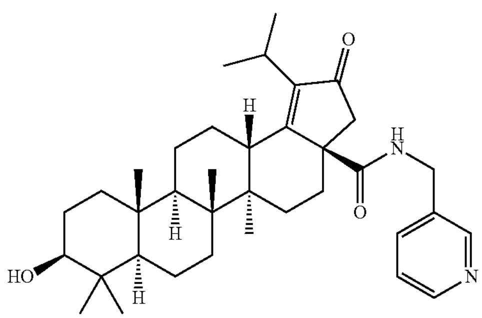 | 3β-O-Hydroxy-21-oxolup-18-en-28-oic acid N-pyridin-3-ylmethylamide | 1H NMR (400 MHz, CDCl$_3$): δ [ppm] 8.60 (s, 1H), 8.54 (d, 1H), 7.71 (d, 1H), 7.31 (m, 1H), 5.92 (br t, 1H), 4.57 (d x d, 1H), 4.30 (d x d, 1H), 3.20 (m, 2H), 2.55 (m, 2H), 2.40 (d, 1H), 2.16 (d, 1H), 1.95-0.60 (m, 38H) |
| 8-18 | 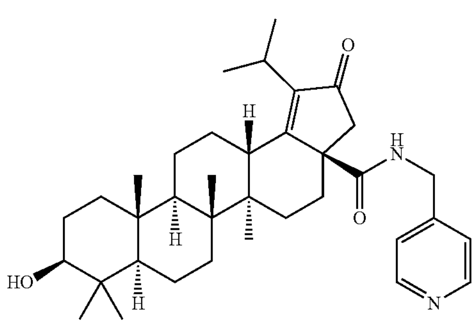 | 3β-O-Hydroxy-21-oxolup-18-en-28-oic acid N-pyridin-4-ylmethylamide | LC/MS: 9.9 min. (Method a) M + H⁺ 561.55 |

TABLE 2-continued

| Cpd # | Structure | Compound name | Analytical data |
|---|---|---|---|
| 8-19 | 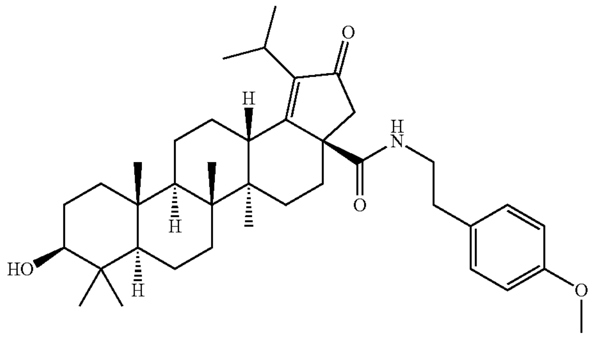 | 3β-O-Hydroxy-21-oxolup-18-en-28-oic acid N-[2-(4-methoxy-phenyl)-ethyl]-acetamide | LC/MS: 9.69 min. (Method b) M + H⁺ 604.71 |
| 8-20 | 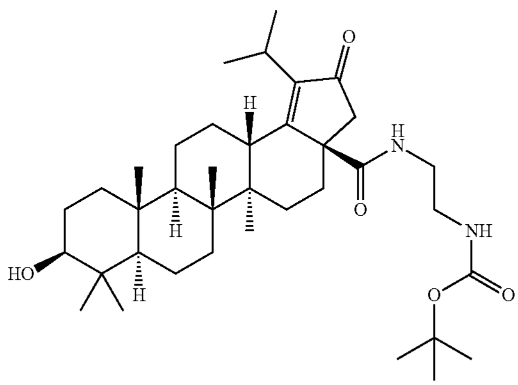 | 3β-O-Hydroxy-21-oxolup-18-en-28-oic acid N-(2-acetylamino-ethyl)-carbamic acid tert-butyl ester | LC/MS: 7.96 min. (Method b) M - Boc + H⁺ 513.59 |
| 8-21 | 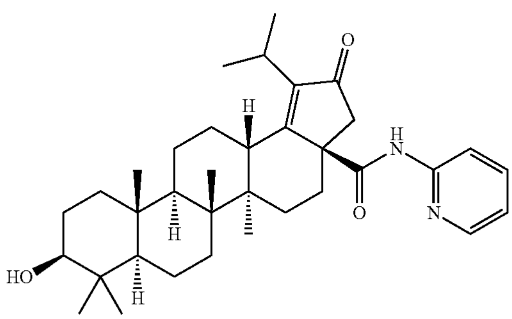 | 3β-O-Hydroxy-21-oxolup-18-en-28-oic acid N-pyridin-2-yl-acetamide | LC/MS: 8.02 min. (Method b) M + H⁺ 547.58 |
| 8-22 | 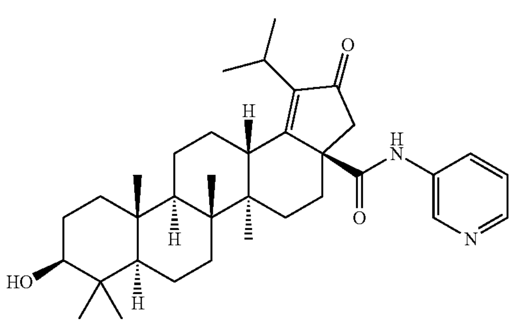 | 3β-O-Hydroxy-21-oxolup-18-en-28-oic acid N-pyridin-3-yl-acetamide | LC/MS: 2.47 min. (Method b) M + H⁺ 547 |

TABLE 2-continued

| Cpd # | Structure | Compound name | Analytical data |
|---|---|---|---|
| 8-23 | 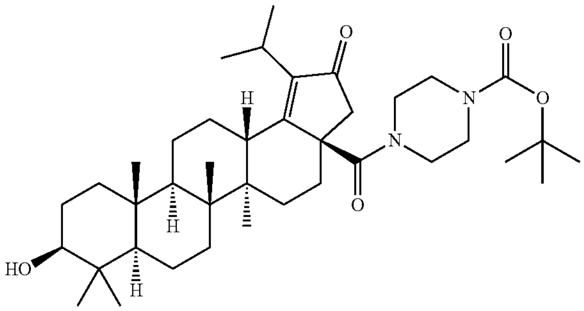 | 3β-O-Hydroxy-21-oxolup-18-en-28-oic acid N-1-acetyl-piperazine-4-carboxylic acid tert-butyl ester | LC/MS: 10.37 min. (Method b) M + H$^+$ 639.69 |
| 8-24 | 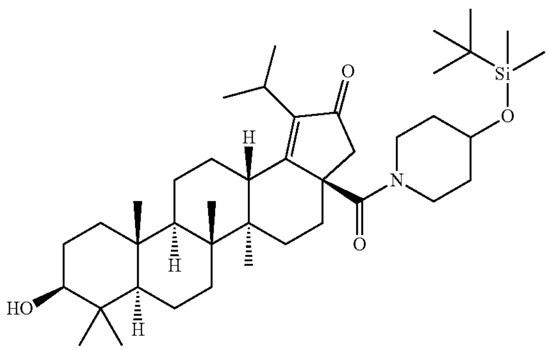 | 3β-O-Hydroxy-21-oxolup-18-en-28-oic acid N-1-(4-tert-butyl-dimethyl-silanyloxy-piperidin-1-yl)-acetamide | LC/MS: 17.65 min. (Method b) M + H$^+$ 669.81 |
| 8-25 | 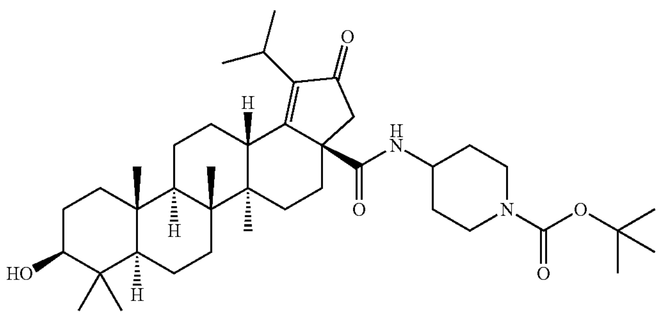 | 3β-O-Hydroxy-21-oxolup-18-en-28-oic acid N-1-acetylamino-piperidine-4-carboxylic acid rerr-butyl ester | LC/MS: 10.6 min. (Method b) M + H$^+$ 653.72 |
| 8-26 | 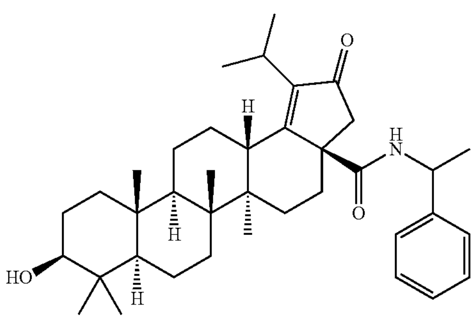 | 3β-O-Hydroxy-21-oxolup-18-en-28-oic acid N-(1-phenyl-ethyl)-acetamide | LC/MS: 10.44 min. (Method b) M + H$^+$ 574.56 |
| 8-27 | 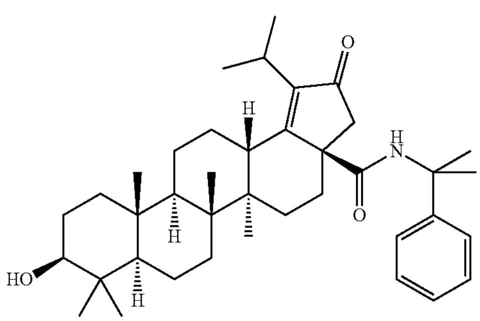 | 3β-O-Hydroxy-21-oxolup-18-en-28-oic acid N-(1-methyl-1-phenyl-ethyl)-acetamide | LC/MS: 11.95 min. (Method b) M + H$^+$ 588.58 |

TABLE 2-continued

| Cpd # | Structure | Compound name | Analytical data |
|---|---|---|---|
| 8-28 | 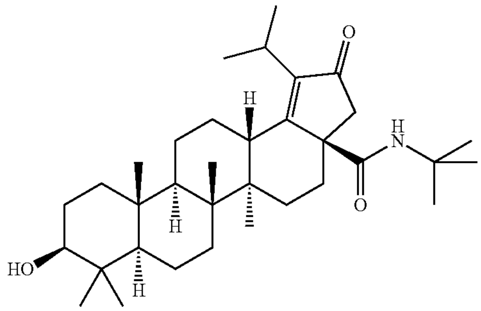 | 3β-O-Hydroxy-21-oxolup-18-en-28-oic acid N-(tert-butyl)-acetamide | LC/MS: 10.52 min. (Method b) M + H+ 526.54 |
| 8-29 | 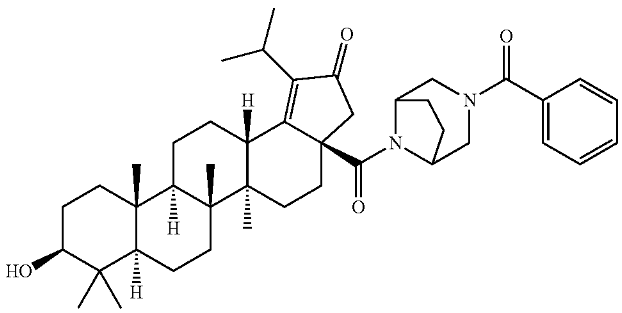 | 3β-O-Hydroxy-21-oxolup-18-en-28-oic acid N-(8-amino-3,8-diaza-bicyclo[3.2.1]octane-3-benzamide)-acetamide | LC/MS: 8.08 min. (Method b) M + H+ 669.62 |
| 8-30 | 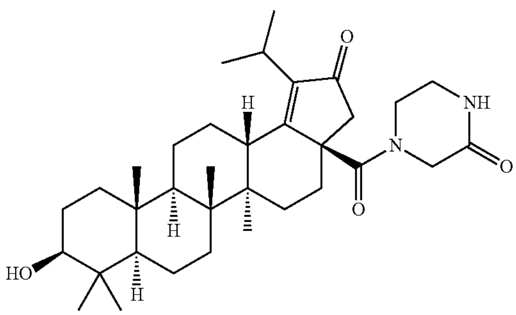 | 3β-O-Hydroxy-21-oxolup-18-en-28-oic acid N-4-piperazi-2-one-acetamide | LC/MS: 12.4 min. (Method a) M + H+ 553.31 |
| 8-31 | 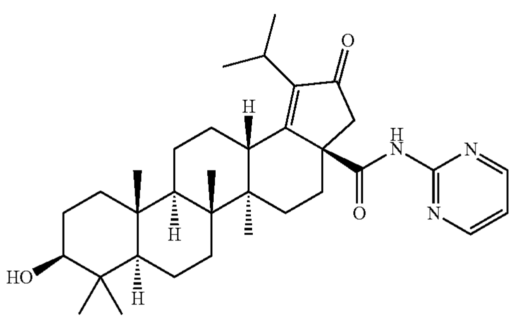 | 3β-O-Hydroxy-21-oxolup-18-en-28-oic acid N-pyrimidin-2-yl-acetamide | 1H NMR (400 MHz, CDCl$_3$): δ [ppm] 8.60 (d, 2H), 7.74 (s, 1H), 7.03 (t, 1H), 3.32 (m, 1H), 3.20 (m, 1H), 2.75 (m, 2H), 2.63 (d, 1H), 2.22 (d, 1H), 2.05 (m, 1H), 1.94 (m, 2H), 1.72 (m, 1H), 1.70-0.65 (m, 34H) |
| 8-32 | 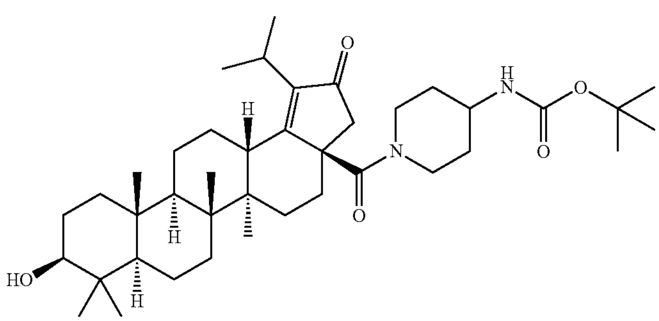 | 3β-O-Hydroxy-21-oxolup-18-en-28-oic acid N-(4-amino carboxylic acid tert-butyl-ester-1-piperidine)-acetamide | 1H NMR (400 MHz, CD$_3$OD): δ [ppm] 4.52 (m, 1H), 3.88 (m, 1H), 3.25 (m, 1H), 3.15 (d x d, 1H), 2.95 (m, 1H), 2.72 (m, 2H), 2.46 (d, 1H), 2.20 (m, 1H), 2.00-0.70 (m, 52H) |

TABLE 2-continued

| Cpd # | Structure | Compound name | Analytical data |
|---|---|---|---|
| 8-33 | 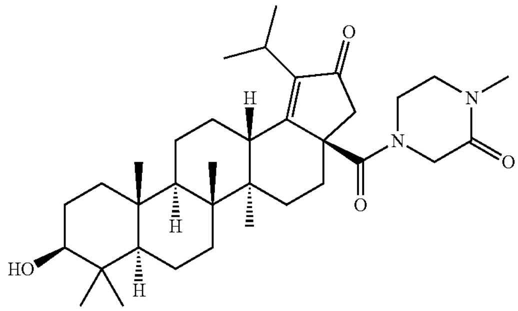 | 3β-O-Hydroxy-21-oxolup-18-en-28-oic acid N-4-(1-methyl-piperazi-2-one)-acetamide | 1H NMR (400 MHz, CDCl₃): δ [ppm] 4.49 (s, 1H), 4.33 (d x d, 1H), 3.60 (m, 1H), 3.27 (d x d, 1H), 3.14 (d x d, 1H), 3.08-2.94 (m, 5H), 2.60 (d, 1H), 2.30 (d, 1H), 2.15 (m, 3H), 1.75-0.60 (m, 38H) |
| 8-34 | 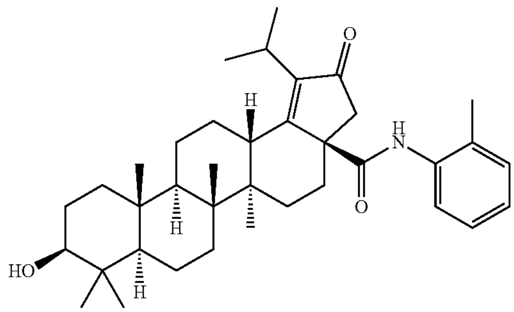 | 3β-O-Hydroxy-21-oxolup-18-en-28-oic acid N-2-methyl-phen-1-yl acetamide | LC/MS: 10.82 min. (Method b) M + H⁺ 560.35 |
| 8-35 | 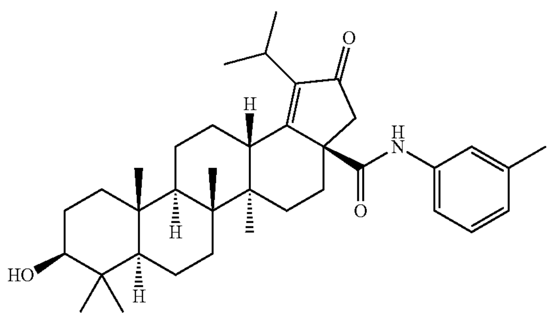 | 3β-O-Hydroxy-21-oxolup-18-en-28-oic acid N-3-methyl-phen-1-yl acetamide | LC/MS: 11.9 min. (Method b) M + H⁺ 560.33 |
| 8-36 | 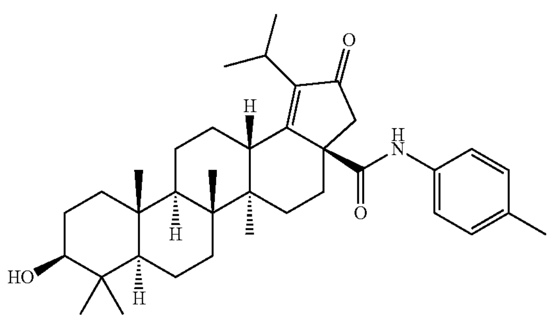 | 3β-O-Hydroxy-21-oxolup-18-en-28-oic acid N-4-methyl-phen-1-yl acetamide | LC/MS: 11.71 min. (Method b) M + H⁺ 560.34 |
| 8-37 | 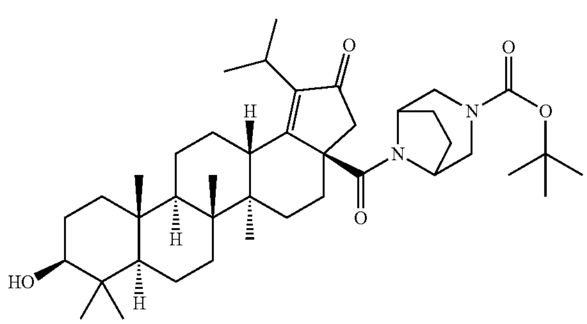 | 3β-O-Hydroxy-21-oxolup-18-en-28-oic acid N-8-acetylamino-3,8-diaza-bicyclo[3.2.1]octane-3-carboxylic acid tert-butyl ester | 1H NMR (400 MHz, CDCl₃): δ [ppm] 4.8 (br s, 1H), 3.84 (m, 2H), 3.17 (m, 2H), 3.02-2.68 (m, 3H), 2.25 (m, 2H), 2.03 (m, 1H), 1.86-1.51 (m, 10H), 1.43-1.13 (m, 27H) 0.99 (br s, 3H), 0.95 (s, 6H), 0.85 (s, 3H), 0.74 (s, 3H), 0.68 (br d, 1H) |

TABLE 2-continued

| Cpd # | Structure | Compound name | Analytical data |
|---|---|---|---|
| 8-38 | 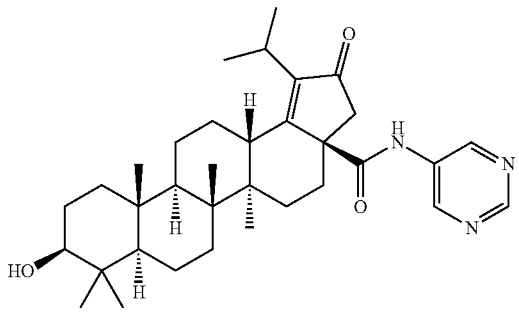 | 3β-O-Hydroxy-21-oxolup-18-en-28-oic acid N-pyrimidin-5-yl-acetamide | 1H NMR (400 MHz, CDCl₃): δ [ppm] 8.98 (s, 1H), 8.86 (s, 1H), 6.92 (s, 1H), 3.31 (m, 1H), 3.20 (m, 1H), 2.70 (m, 2H), 2.55 (d, 1H), 2.30 (d, 1H), 1.95 (m, 2H), 1.80-0.65 (m, 36H) |
| 8-39 | 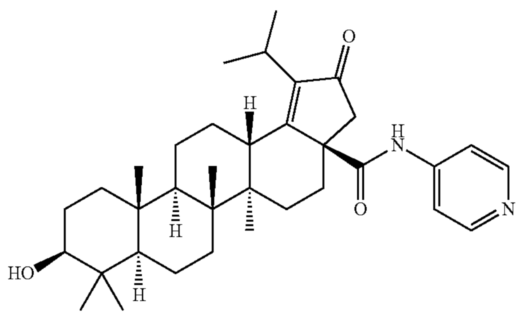 | 3β-O-Hydroxy-21-oxolup-18-en-28-oic acid N-pyridin-4-yl-acetamide | LC/MS: 10.27 min. (Method a) M + H⁺ 547.23 |
| 8-40 | 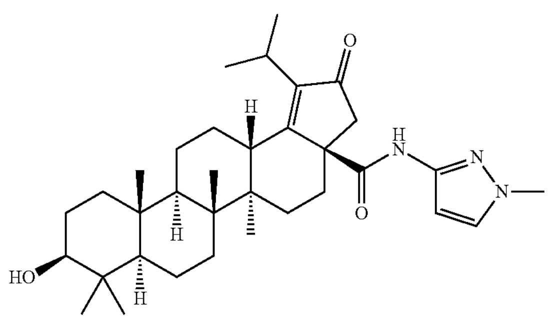 | 3β-O-Hydroxy-21-oxolup-18-en-28-oic acid N-3-amino-1-methyl-1H-pyrazole-acetamide | LC/MS: 14.91 min. (Method a) M + H⁺ 550.25 |
| 8-41 | 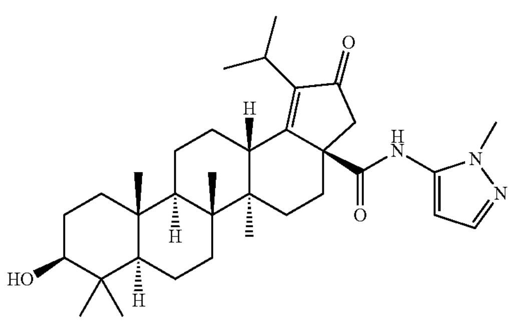 | 3β-O-Hydroxy-21-oxolup-18-en-28-oic acid N-5-amino-1-methyl-1H-pyrazole-acetamlde | LC/MS: 14.3 min. (Method a) M + H⁺ 550.25 |
| 8-42 | 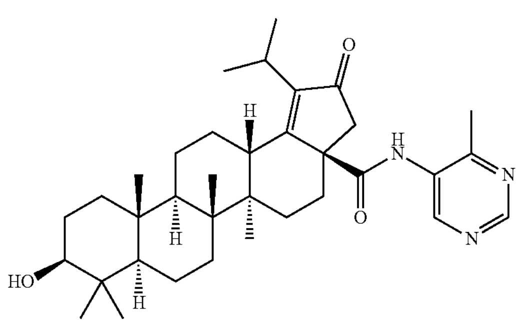 | 3β-O-Hydroxy-21-oxolup-18-en-28-oic acid N-4-methyl-pyrimidin-5-yl-acetamide | 1H NMR (400 MHz, CDCl₃): δ [ppm] 9.22 (s, 1H), 8.88 (s, 1H), 6.92 (s, 1H), 3.31-3.34 (m, 1H), 3.17-3.21 (d x d, 1H), 2.70-2.74 (m, 2H), 2.57 (d, 1H), 2.43 (s, 3H), 2.31 (d, 1H), 1.84-2.03 (m, 3H), 1.72-1.75 (m, 1H), 1.28 (d, 3H), 1.25 (d, 3H), 1.19-1.04 (m, 11H), 1.01 (s, 3H), 0.97 (s, 3H), 0.96 (s, 3H), 0.90-0.80 (m, 1H), 0.85 (s, 3H), 0.74 (s, 3H), 0.68-0.71 (m, 1H) |

TABLE 2-continued

| Cpd # | Structure | Compound name | Analytical data |
|---|---|---|---|
| 8-43 | 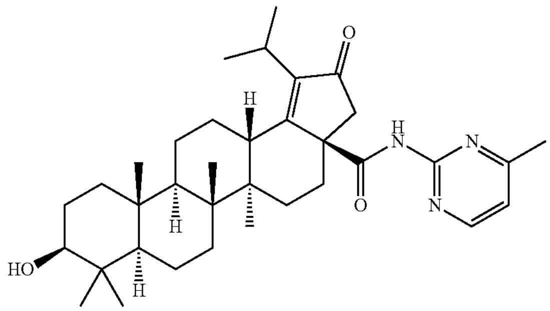 | 3β-O-Hydroxy-21-oxolup-18-en-28-oic acid N-4-methyl-pyrimidin-2-yl-acetamide | 1H NMR (400 MHz, CDCl$_3$): δ [ppm] 8.46 (d, 1H), 7.85 (br d, 1H), 7.89 (d, 1H), 6.89 (d, 1H), 3.34-3.30 (m, 1H), 3.21-3.17 (m, 1H), 2.76-2.73 (br d, 1H), 2.62 (d, 1H), 2.47 (s, 3H), 2.24 (d, 1H), 2.10 (br d, 1H), 1.94 (m, 2H), 1.73 (m, 1H), 1.64-1.43 (m, 6H), 1.42-1.20 (m, 7H), 1.32 (d, 3H), 1.24 (d, 3H), 1.0 (s, 1H), 0.96 (s, 6H), 0.90-0.80 (m, 1H), 0.83 (s, 3H), 0.73 (s, 3H), 0.68 (m, 1H) |
| 8-44 | 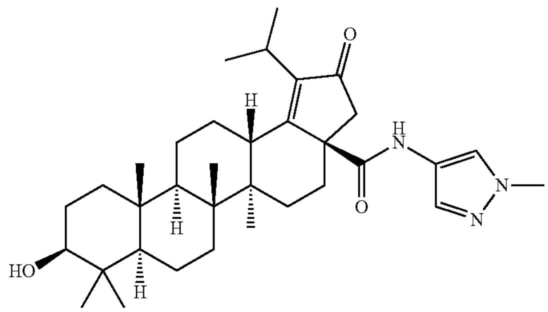 | 3β-O-Hydroxy-21-oxolup-18-en-28-oic acid N-4-amino-1-methyl-1H-pyrazole-acetamide | 1H NMR (400 MHz, CDCl$_3$): δ [ppm] 7.85 (s, 1H), 7.29 (s, 1H), 6.82 (s, 1H), 3.85 (s, 3H), 3.30-3.27 (m, 1H), 3.21-3.17 (d x d, 1H), 2.70-2.62 (m, 2H), 2.50 (d, 1H), 2.22 (d, 1H), 2.12 (br d, 1H), 2.03-1.82 (m, 2H), 1.73 (m, 1H), 1.66-1.45 (m, 7H), 1.42-1.20 (m, 6H), 1.27 (d, 3H), 1.23 (d, 3H), 0.98 (s, 3H), 0.95 (s, 3H), 0.94 (s, 3H), 0.95 (m, 1H), 0.84 (s, 3H), 0.74 (s, 3H), 0.69 (m, 1H) |
| 8-45 | 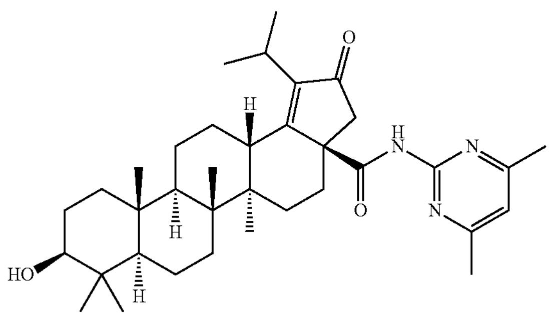 | 3β-O-Hydroxy-21-oxolup-18-en-28-oic acid N-4,6-dimethyl-pyrimidin-2-yl-acetamide | 1H NMR (400 MHz, CDCl$_3$): δ [ppm] 7.67 (br s, 1H), 6.74 (s, 1H), 3.32 (m, 1H), 3.19 (d x d, 1H), 2.75 (m, 2H), 2.63 (d, 1H), 2.42 (s, 6H), 2.21 (d, 1H), 2.10 (br d, 1H), 2.03-1.90 (m, 2H), 1.74 (m, 1H), 1.66-1.45 (m, 6H), 1.41-1.17 (m, 7H), 1.31 (d, 3H), 1.24 (d, 3H), 1.0 (s, 3H), 0.95 (s, 6H), 0.85 (m, 1H), 0.84 (s, 3H), 0.73 (s, 3H), 0.69 (m, 1H) |
| 8-46 | 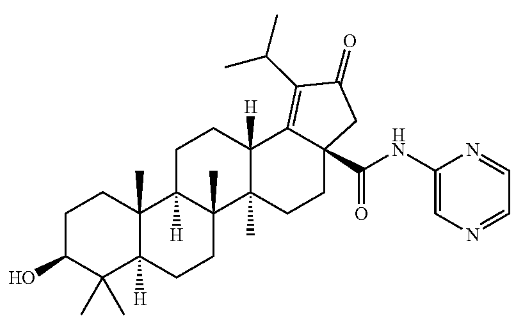 | 3β-O-Hydroxy-21-oxolup-18-en-28-oic acid N-pyrazin-2-yl-acetamide | LC/MS: 15.85 min. (Method a) M + H$^+$ 548.17 |
| 8-47 | 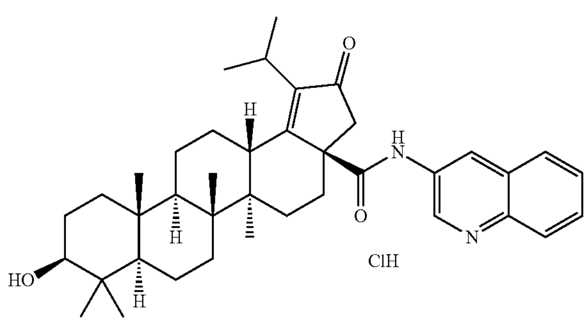 | 3β-O-Hydroxy-21-oxolup-18-en-28-oic acid N-quinolin-3-yl-acetamide hydrochloride | 1H NMR (400 MHz, CDCl$_3$): δ [ppm] 8.70 (br s, 2H), 8.02 (br d, 1H), 7.76 (d, 1H), 7.61 (m, 1H), 7.52 (m, 1H), 3.30 (m, 1H), 3.14 (d x d, 1H), 2.72 (m, 2H), 2.58 (d, 1H), 2.28 (d, 1H), 2.03 (br d, 1H), 1.90 (m, 2H), 1.68 (m, 1H), 1.61-1.33 (m, 6H), 1.39-1.08 (m, 7H), 1.28 (d, 3H), 1.22 (d, 3H), 0.95 (s, 3H), 0.93 (s, 3H), 0.90 (s, 3H), 0.85 (m, 1H), 0.78 (s, 3H), 0.68 (s, 3H), 0.65 (m, 1H) |

TABLE 2-continued

| Cpd # | Structure | Compound name | Analytical data |
|---|---|---|---|
| 8-48 | 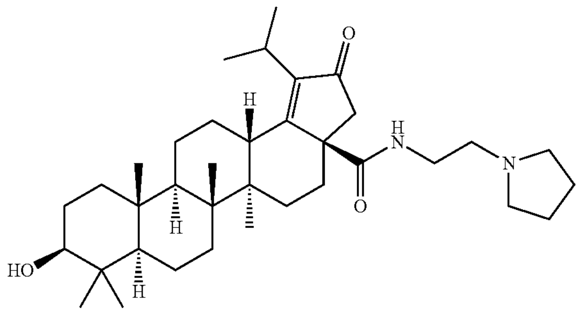 | 3β-O-Hydroxy-21-oxolup-18-en-28-oic acid N-(2-pyrrolidin-1-yl-ethyl)-acetamide | 1H NMR (400 MHz, CDCl$_3$): δ [ppm] 3.46 (br s, 1H), 3.22 (m, 3H), 2.66 (m, 6H), 2.39 (d, 1H), 2.15 (d, 1H), 2.0 (m, 1H), 1.91-1.72 (m, 7H), 1.69-1.24 (m, 5H), 1.22 (d, 3H), 1.20 (d, 3H), 1.19-1.08 (m, 9H), 1.0 (s, 3H), 0.95 (s, 3H), 0.91 (s, 3H), 0.88-0.81 (m, 1H), 0.86 (s, 3H), 0.74 (s, 3H), 0.68 (m, 1H) |
| 8-49 | 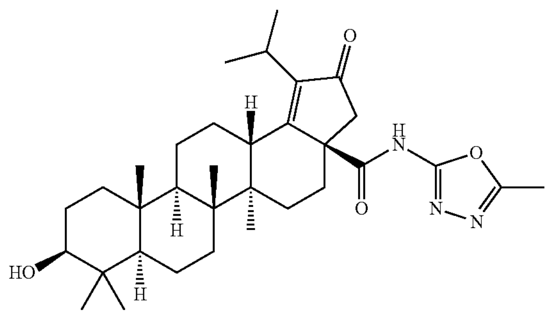 | 3β-O-Hydroxy-21-oxolup-18-en-28-oic acid N-(5-methyl-[1,3,4]oxadiazol-2-yl)-acetamide | LC/MS: 13.7 min. (Method a) M + H$^+$ 552.11 |
| 8-50 | 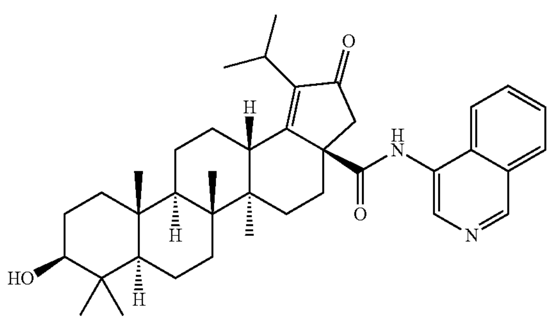 | 3β-O-Hydroxy-21-oxolup-18-en-28-oic acid N-isoquinolin-4-yl-acetamide | 1H NMR (400 MHz, CDCl$_3$): δ [ppm] 9.30 (s, 1H), 9.24 (s, 1H), 8.29 (d, 1H), 8.07 (t, 1H), 7.92 (t, 1H), 7.66 (d, 1H), 3.34 (m, 1H), 3.14 (d x d, 1H), 2.78 (m, 1H), 2.70 (m, 1H), 2.63 (d, 1H), 2.37 (d, 1H), 1.99-1.81 (m, 3H), 1.68-1.10 (m, 14H), 1.34 (d, 3H), 1.24 (d, 3H), 0.97 (s, 3H), 0.96 (s, 3H), 0.91 (s, 3H), 0.91-0.79 (m, 1H), 0.78 (s, 3H), 0.69 (s, 3H), 0.64 (m, 1H) |
| 8-51 | 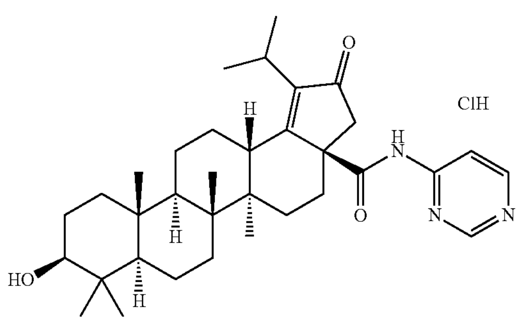 | 3β-O-Hydroxy-21-oxolup-18-en-28-oic acid N-pyrimidin-4-yl-acetamide | 1H NMR (400 MHz, CDCl$_3$): δ [ppm] 8.86 (s, 1H), 8.61 (br s, 1H), 8.28 (br s, 1H), 7.92 (br s, 1H), 3.31 (m, 1H), 3.14 (m, 1H), 2.49 (d, 1H), 2.68-2.37 (m, 3H), 2.24 (d, 1H), 2.04-1.77 (m, 5H), 1.68 (m, 1H), 1.61-1.11 (m, 9H). 1.26 (d, 3H), 1.19 (d, 3H), 0.93 (s, 3H), 0.91 (s, 3H), 0.91 (s, 3H), 0.91-0.79 (m, 1H), 0.78 (s, 3H), 0.69 (s, 3H), 0.64 (m, 1H) |
| 8-52 | 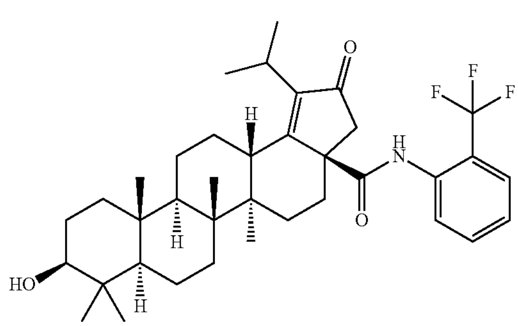 | 3β-O-Hydroxy-21-oxolup-18-en-28-oic acid N-2-trifluoromethyl-phen-1-yl acetamide | 1H NMR (400 MHz, CDCl$_3$): δ [ppm] 8.06 (d, 1H), 7.52 (m, 2H), 7.43 (s, 1H), 7.15 (m, 1H), 3.26 (m, 1H), 3.14 (m, 1H), 2.72 (m, 1H), 2.53 (d, 1H), 2.21 (d, 1H), 2.01 (m, 1H), 1.93-1.75 (m, 2H), 1.69 (m, 1H), 1.63-1.40 (m, 6H), 1.36-1.10 (m, 7H), 1.20 (d, 3H), 1.18 (d, 3H), 0.92 (s, 3H), 0.91 (s, 3H), 0.90 (s, 3H), 0.96-0.76 (m, 1H), 0.79 (s, 3H), 0.69 (s, 3H), 0.64 (m, 1H) |

TABLE 2-continued

| Cpd # | Structure | Compound name | Analytical data |
|---|---|---|---|
| 8-53 | 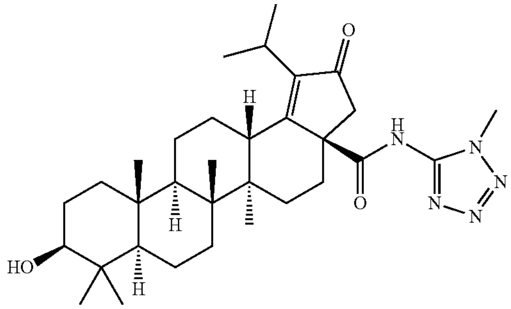 | 3β-O-Hydroxy-21-oxolup-18-en-28-oic acid N-(1-methyl-1H-tetrazol-5-yl)-acetamide | 1H NMR (400 MHz, CDCl₃): δ [ppm] 3.30-3.00 (m, 6H), 2.70-0.62 (m, 12H), 1.20 (d, 3H), 1.16 (d, 3H), 0.91 (br s, 9H), 0.83 (s, 3H), 0.70 (s, 3H) |
| 8-54 | 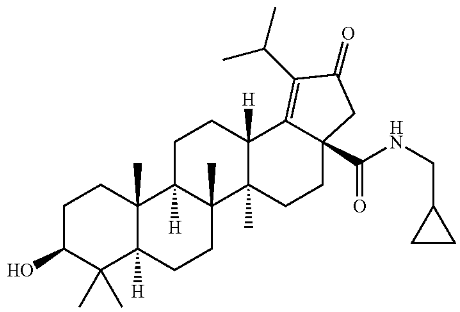 | 3β-O-Hydroxy-21-oxolup-18-en-28-oic acid N-cyclopropylmethyl acetamide | 1H NMR (400 MHz, CDCl₃): δ [ppm] 5.23 (t, 1H), 3.2-3.02 (m, 3H), 2.81 (m, 1H), 2.57 (d x d, 1H), 2.48 (m, 1H), 2.28 (d, 1H), 2.0 (d, 1H), 1.92-1.31 (m, 12H), 1.24-1.06 (m, 10H), 0.78-0.67 (m, 14H), 0.60 (s, 3H), 0.54 (br d, 1H), 0.33 (m, 2H), 0.02 (m, 2H) |
| 8-55 | 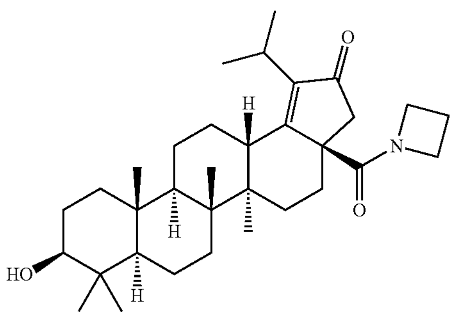 | 3β-O-Hydroxy-21-oxolup-18-en-28-oic acid N-azetidine-1 acetamide | 1H NMR (400 MHz, CDCl₃): δ [ppm] 3.19 (m, 2H), 2.64 (m, 2H), 2.47 (d, 1H), 2.21-2.13 (m, 3H), 2.03-1.86 (m, 5H), 1.74 (m, 1H), 1.68-1.44 (m, 8H), 1.36-1.24 (m, 4H), 1.2-1.14 (m, 8H), 1.04 (s, 3H), 1.0-0.86 (m, 10H), 0.75 (s, 3H), 0.68 (br d, 1H) |
| 8-56 | 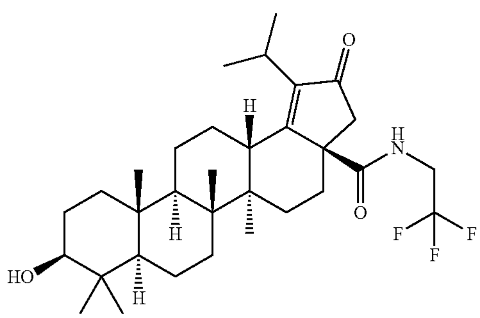 | 3β-O-Hydroxy-21-oxolup-18-en-28-oic acid N-(2,2,2-trifluoro-ethyl)-acetamide | HPLC: 24.46 min. (Method A) LC/MS: M + H⁺ 552.3 |
| 8-57 | 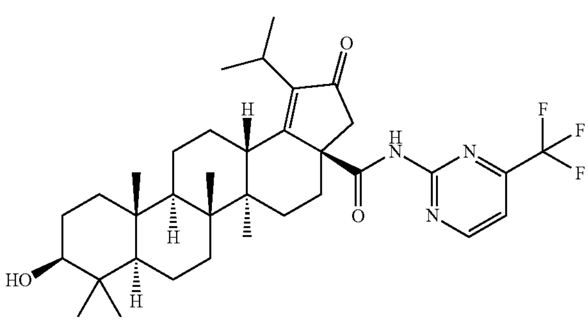 | 3β-O-Hydroxy-21-oxolup-18-en-28-oic acid N-4-trifluoro-pyrimidin-2-yl-acetamide | 1H NMR (400 MHz, CDCl₃): δ [ppm] 8.82 (d, 1H), 7.85 (s, 1H), 7.29 (d, 1H), 6.93 (br s, 1H), 3.31-3.26 (m, 1H), 3.14 (m, 1H), 2.68 (br d, 1H), 2.54 (d, 1H), 2.24-1.24 (m, 23H), 1.00-0.83 (m, 13H), 0.73 (s, 3H), 0.68 (d, 1H) |

TABLE 2-continued

| Cpd # | Structure | Compound name | Analytical data |
|---|---|---|---|
| 8-58 | 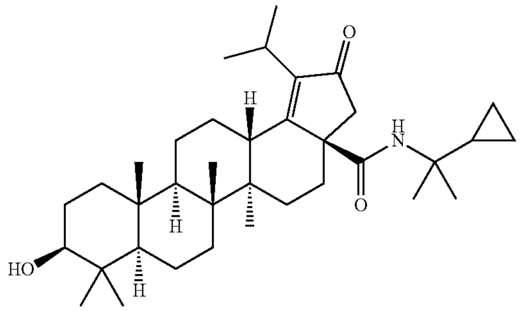 | 3β-O-Hydroxy-21-oxolup-18-en-28-oic acid N-(1-cyclopropyl-1-methyl-ethyl)-acetamide | LC/MS: 11.39 min. (Method b) M + H+ 552.41 |
| 8-59 | 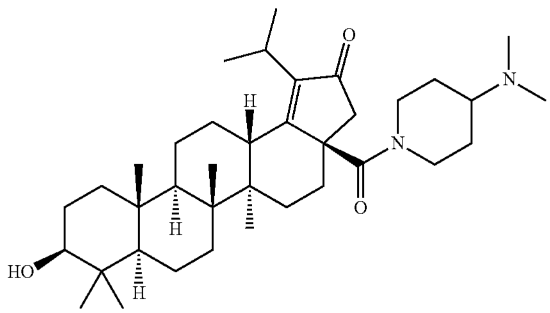 | 3β-O-Hydroxy-21-oxolup-18-en-28-oic acid N-(4-dimethylamino-piperidin-1-yl)-acetamide | LC/MS: 9.17 min. (Method a) M + H+ 581.49 |
| 8-60 | 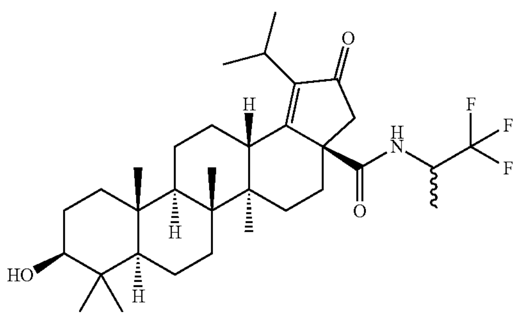 | 3β-O-Hydroxy-21-oxolup-18-en-28-oic acid N-(2,2,2-trifluoro-1-methyl-ethyl)-acetamide | LC/MS: 10.26 min. (Method b) M + H+ 566.32 |
| 8-61 | 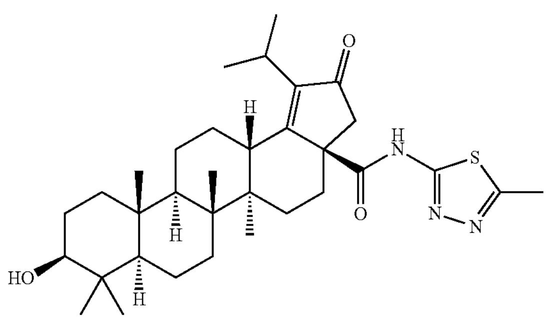 | 3β-O-Hydroxy-21-oxolup-18-en-28-oic acid N-(5-methyl-[1,3,4]thiadiazol-2-yl)-acetamide | LC/MS: 7.06 min. (Method b) M + H+ 568.31 |
| 8-62 | 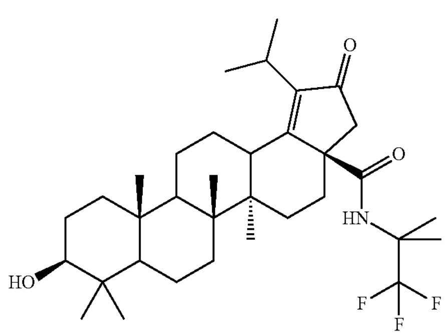 | 3β-O-Hydroxy-21-oxolup-18-en-28-oic acid N-(2,2,2-trifluoro-1,1-dimethyl-ethyl)-acetamide | LC/MS: 11.51 min. (Method b) M + H+ 580.42 |

TABLE 2-continued

| Cpd # | Structure | Compound name | Analytical data |
|---|---|---|---|
| 8-63 | 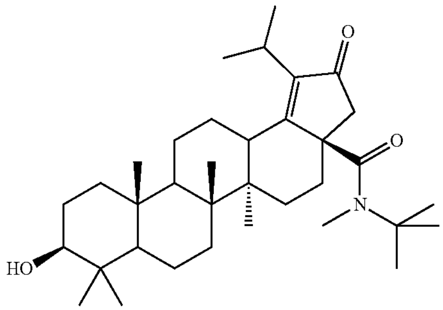 | 3β-O-Hydroxy-21-oxolup-18-en-28-oic acid N-tert-butyl-N-methyl-acetamide | LC/MS: 11 min. (Method b) M + H⁺ 540.39 |
| 8-64 | 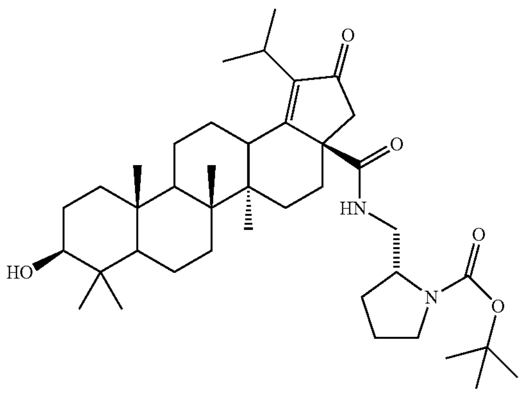 | 3β-O-Hydroxy-21-oxolup-18-en-28-oic acid N-(R)-2-acetylaminomethyl-pyrrolidine-1-carboxylic acid tert-butyl ester | 1H NMR (400 MHz, CDCl₃): δ [ppm] 7.4 (br s, 1H), 3.8 (br m, 1H), 3.58 (m, 1H), 3.37 (m, 1H), 3.29-3.16 (m, 3H), 3.0 (m, 1H), 2.8 (br d, 1H), 2.57 (m, 1H), 2.37 (d, 1H), 2.13-2.02 (m, 2H), 1.87-1.16 (m, 33H), 1.0-0.79 (m, 14H), 0.74 (s, 3H), 0.68 (br d, 1H) |
| 8-65 | 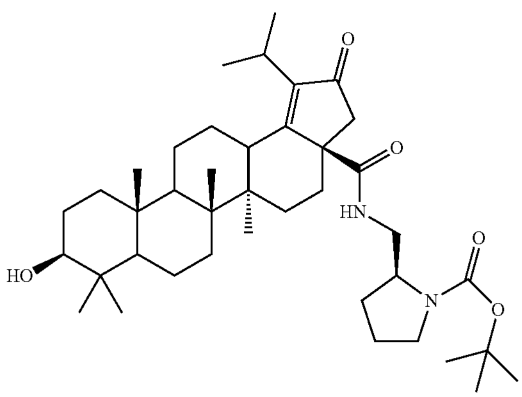 | 3β-O-Hydroxy-21-oxolup-18-en-28-oic acid N-(S)-2-acetylaminomethyl-pyrrolidine-1-carboxylic acid tert-butyl ester | 1H NMR (400 MHz, CDCl₃): δ [ppm] 7.4 (br s, 1H), 3.8 (br m, 1H), 3.58 (m, 1H), 3.37 (m, 1H), 3.29-3.16 (m, 3H), 3.06 (m, 1H), 2.71 (br d, 1H), 2.56 (m, 1H), 2.39 (d, 1H), 2.13-2.02 (m, 2H), 1.87-1.16 (m, 33H), 1.0-0.79 (m, 14H), 0.74 (s, 3H), 0.68 (br d, 1H) |
| 8-66 | 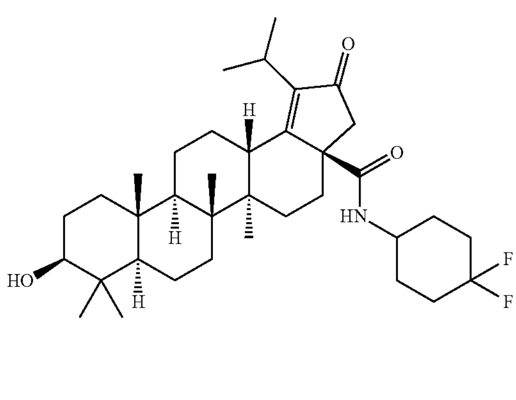 | 3β-O-Hydroxy-21-oxolup-18-en-28-oic acid N-(4,4-difluoro-cyclohexyl)acetamide | HPLC: 27.12 min. (Method A) LC/MS: M + H⁺ 588.52 |

TABLE 2-continued

| Cpd # | Structure | Compound name | Analytical data |
|---|---|---|---|
| 8-67 | 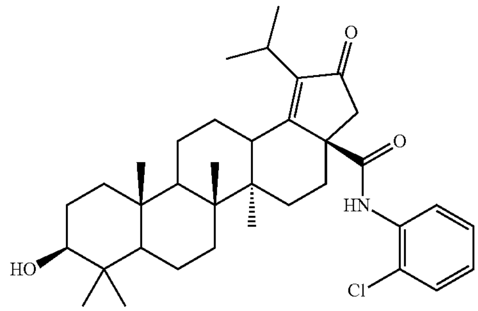 | 3β-O-Hydroxy-21-oxolup-18-en-28-oic acid N-2-chloro-phen-1-yl acetamide | LC/MS: 19.18 min. (Method a) M + H⁺ 580.34 |
| 8-68 | 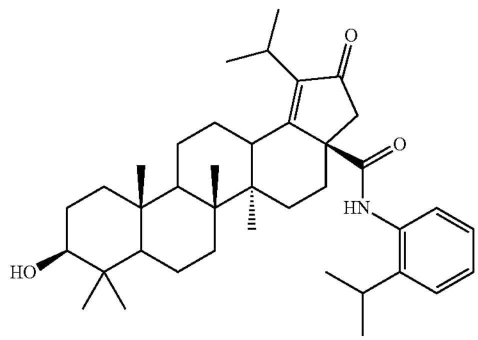 | 3β-O-Hydroxy-21-oxolup-18-en-28-oic acid N-2-isopropyl-phen-1-yl acetamide | LC/MS: 18.67 min. (Method a) M + H⁺ 588.44 |
| 8-69 | 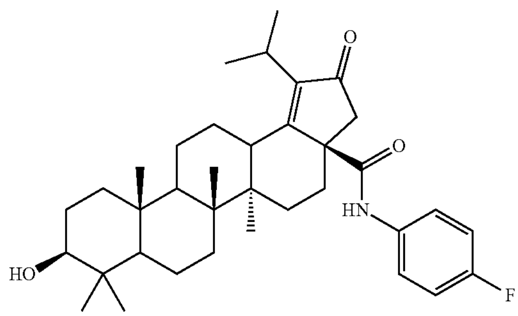 | 3β-O-Hydroxy-21-oxolup-18-en-28-oic acid N-4-fluoro-phen-1-yl acetamide | 1H NMR (400 MHz, CDCl$_3$): δ [ppm] 7.33 (d x d, 2H), 7.0 (d x d, 2H), 6.92 (s, 1H), 3.30 (sept. 1H), 3.18 (d x d, 1H), 2.71 (m, 2H), 2.55 (d, 1H), 2.23 (d, 1H), 2.03-1.85 (m, 3H), 1.74-1.22 (m, 15H), 1.0-0.93 (m, 10H), 0.86-0.81 (m, 7H), 0.74 (s, 3H), 0.69 (m, 1H) |
| 8-70 | 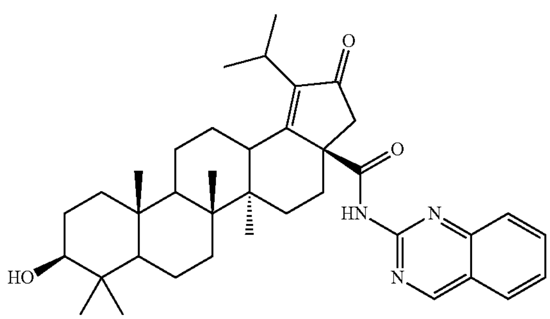 | 3β-O-Hydroxy-21-oxolup-18-en-28-oic acid N-quinazolin-2-yl acetamide | HPLC: 22.01 min. (Method A) LC/MS: M + H⁺ 598.41 |
| 8-71 | 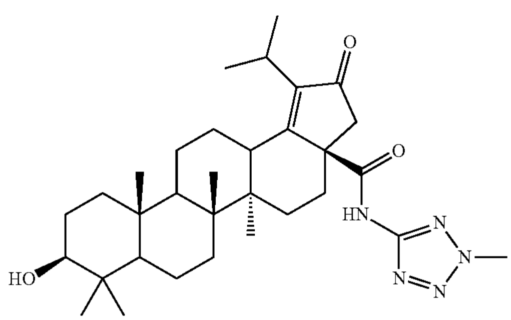 | 3β-O-Hydroxy-21-oxolup-18-en-28-oic acid N-(1-methyl-1H-tetrazol-3-yl)-acetamide | HPLC: 16.12 min. (Method A) LC/MS: M + H⁺ 552.3 |

TABLE 2-continued

| Cpd # | Structure | Compound name | Analytical data |
|---|---|---|---|
| 8-72 | 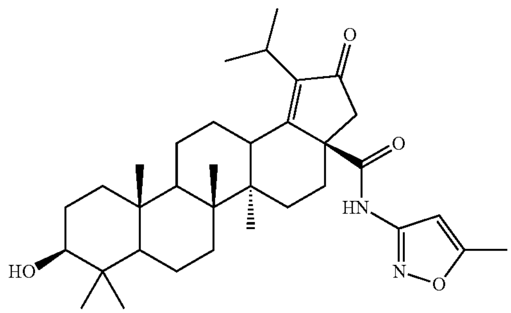 | 3β-O-Hydroxy-21-oxolup-18-en-28-oic acid N-(5-methyl-isoxazol-3-yl)-acetamide | LC/MS: 14.9 min. (Method a) M + H⁺ 551.3 |
| 8-73 | 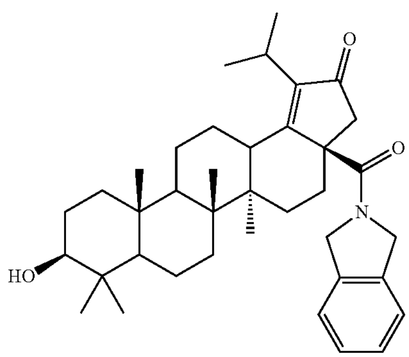 | 3β-O-Hydroxy-21-oxolup-18-en-28-oic acid N-(1,3-dihydro-isoindol-2-yl)-acetamide | 1H NMR (400 MHz, CDCl₃): δ [ppm] 7.25-7.18 (m, 4H), 7.05 (d, 1H), 4.83 (d x d, 2H), 4.40 (d x d, 2H), 3.21 (sept., 1H), 3.13 (m, 1H), 2.75 (m, 1H), 2.52 (br d, 1H), 2.48 (d, 1H), 2.19 (d, 1H), 1.97 (m, 2H), 1.80 (m, 1H), 1.66 (m, 1H), 1.61-1.18 (m, 13H), 0.94-0.88 (m, 10H), 0.85-0.76 (m, 7H), 0.68 (s, 3H), 0.63 (m, 1H) |
| 8-74 | 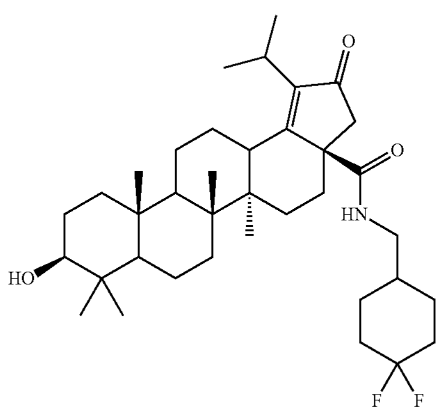 | 3β-O-Hydroxy-21-oxolup-18-en-28-oic acid N-(4,4-difluoro-cyclohexylmethyl)-acetamide | HPLC: 27.54 min. (Method A) LC/MS: M + H⁺ 602.58 |
| 8-75 | 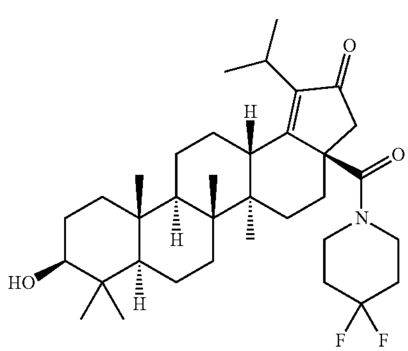 | 3β-O-Hydroxy-21-oxolup-18-en-28-oic acid N-4,4-difluoro-piperidine acetamide | HPLC: 28.62 min. (Method A) LC/MS: M + H⁺ 574.47 |

TABLE 3

| Cpd # | Structure | Compound name | $t_R$ (min.) (Method) | M+/M + H+ |
|---|---|---|---|---|
| 9-2 | 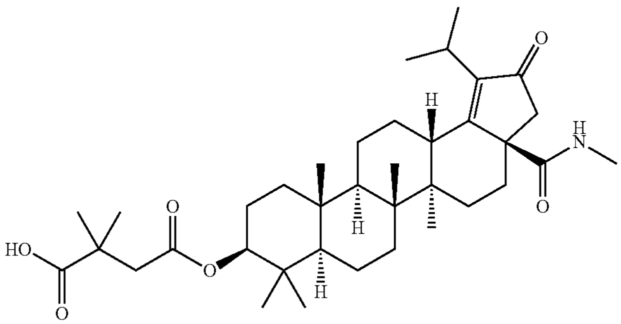 | 3β-O-(3',3'-Dimethylsuccinyl)-21-oxolup-18-en-28-oic acid N-methylamide | 24.7 (A) | 612.70 |
| 9-3 | 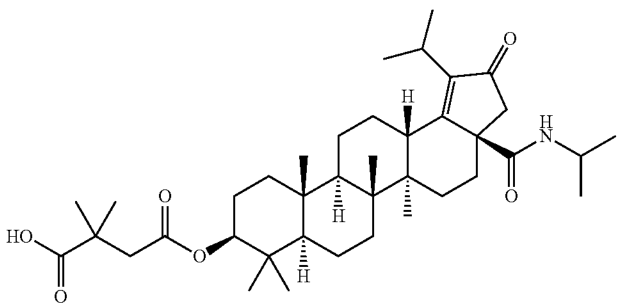 | 3β-O-(3',3'-Dimethylsuccinyl)-21-oxolup-18-en-28-oic acid N-isopropylamide | 31.86 (A) | 640.59 |
| 9-4 | 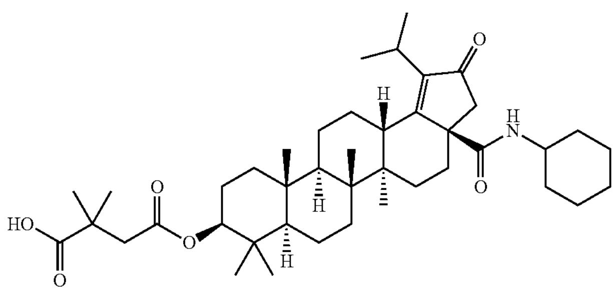 | 3β-O-(3',3'-Dimethylsuccinyl)-21-oxolup-18-en-28-oic acid N-cyclohexylamide | 30.78 (B) | 680.78 |
| 9-5 | 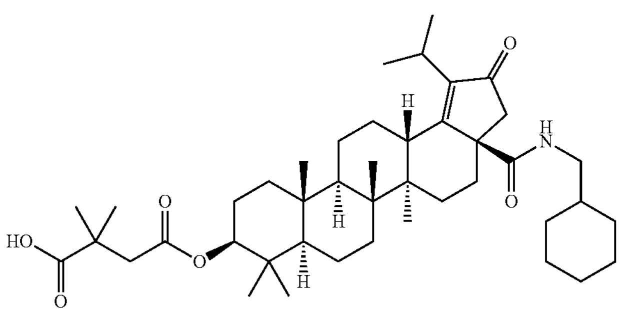 | 3β-O-(3',3'-Dimethylsuccinyl)-21-oxolup-18-en-28-oic acid N-cyclohexyl methylamide | 32.35 (B) | 694.83 |
| 9-6 | 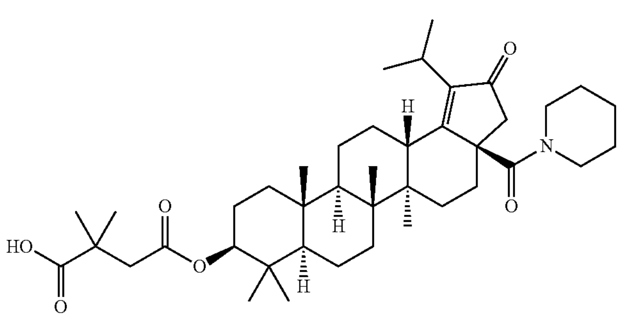 | 3β-O-(3',3'-Dimethylsuccinyl)-21-oxolup-18-en-28-oic acid N-piperidinyl acetamide | 28.63 (B) | ND |

TABLE 3-continued

| Cpd # | Structure | Compound name | t_R (min.) (Method) | M+/M + H+ |
|---|---|---|---|---|
| 9-7 | 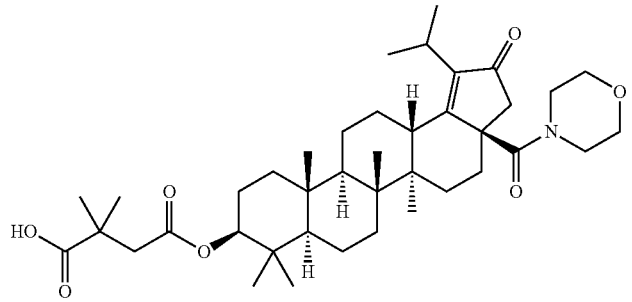 | 3β-O-(3',3'-Dimethylsuccinyl)-21-oxolup-18-en-28-oic acid N-morpholyl acetamide | 20.17 (B) | 668.75 |
| 9-8 | 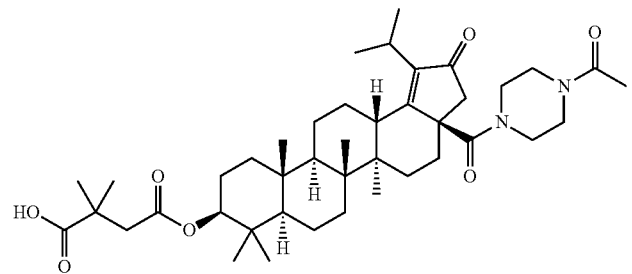 | 3β-O-(3',3'-Dimethylsuccinyl)-21-oxolup-18-en-28-oic acid N-(4-acetyl piperazinyl) acetamide | 20.53 (A) | 709.56 |
| 9-9 | 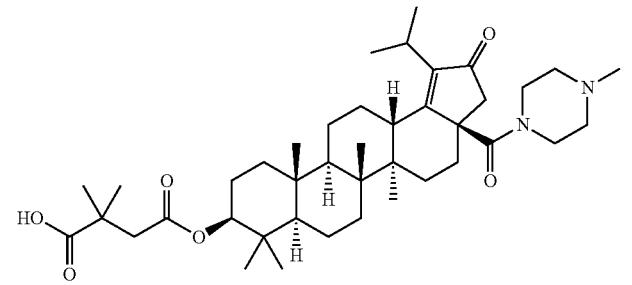 | 3β-O-(3',3'-Dimethylsuccinyl)-21-oxolup-18-en-28-oic acid N-(4-methyl piperazinyl) acetamide | 18.13 (C) | 681.80 |
| 9-10 | 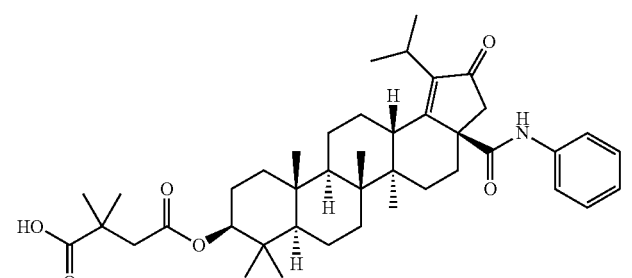 | 3β-O-(3',3'-Dimethylsuccinyl)-21-oxolup-18-en-28-oic acid N-benzamide | 36.48 (A) | 674.56 |
| 9-11 | 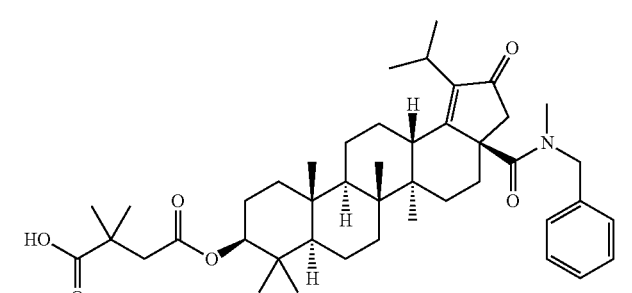 | 3β-O-(3',3'-Dimethylsuccinyl)-21-oxolup-18-en-28-oic acid N-methyl-N-benzylamide | 29.85 (B) | 702.74 |

TABLE 3-continued

| Cpd # | Structure | Compound name | $t_R$ (min.) (Method) | M+/M + H+ |
|---|---|---|---|---|
| 9-12 | 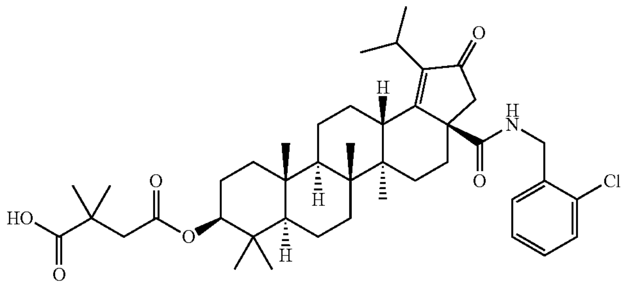 | 3β-O-(3',3'-Dimethylsuccinyl)-21-oxolup-18-en-28-oic acid N-2-chloro-benzylamide | 28.65 (B) | 722.41 |
| 9-13 | 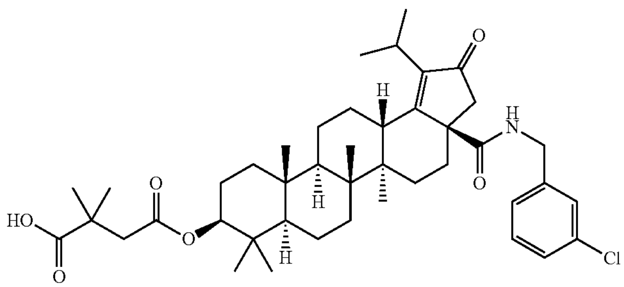 | 3β-O-(3',3'-Dimethylsuccinyl)-21-oxolup-18-en-28-oic acid N-3-chloro-benzylamide | 27.88 (B) | 722.75 |
| 9-14 | 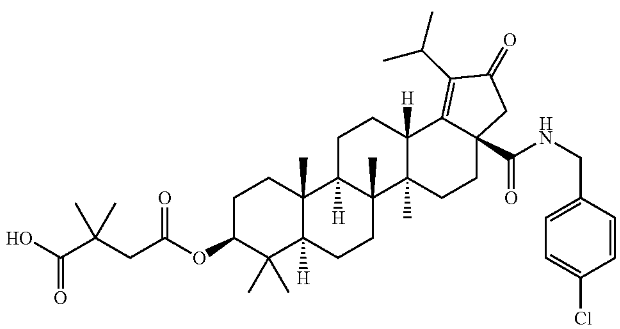 | 3β-O-(3',3'-Dimethylsuccinyl)-21-oxolup-18-en-28-oic acid N-4-chloro-benzylamide | 37.46 (A) | 722.68 |
| 9-15 | 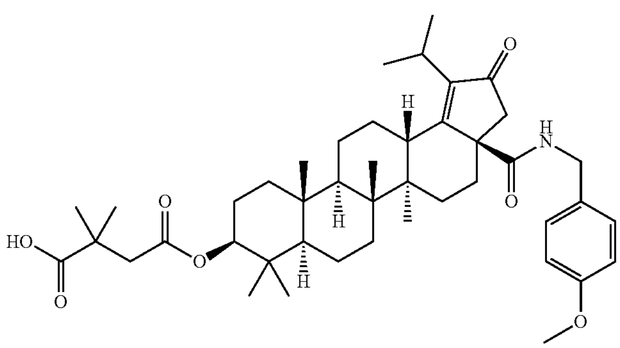 | 3β-O-(3',3'-Dimethylsuccinyl)-21-oxolup-18-en-28-oic acid N-4-methoxy-benzylamide | 32.24 (A) | 718.71 |
| 9-16 | 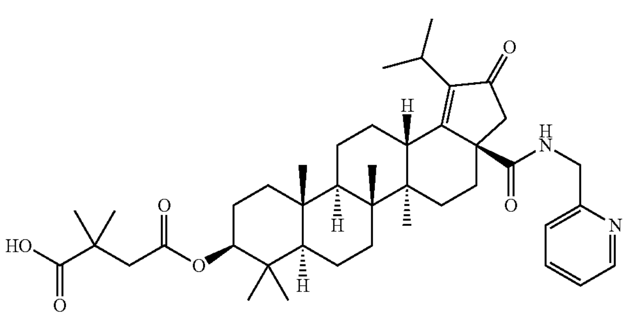 | 3β-O-(3',3'-Dimethylsuccinyl)-21-oxolup-18-en-28-oic acid N-pyridin-2-ylmethylamide | 23.68 (C) | 689.67 |

TABLE 3-continued

| Cpd # | Structure | Compound name | $t_R$ (min.) (Method) | M+/M + H+ |
|---|---|---|---|---|
| 9-17 | 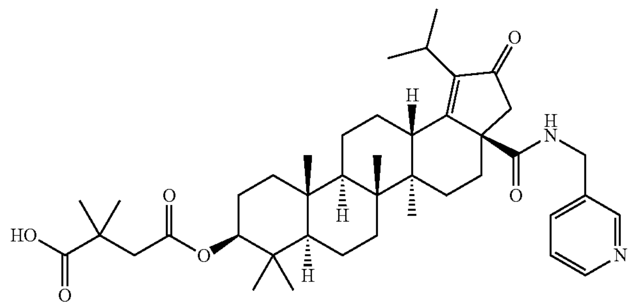 | 3β-O-(3',3'-Dimethylsuccinyl)-21-oxolup-18-en-28-oic acid N-pyridin-3-ylmethylamide | 24.03 (C) | 689.76 |
| 9-18 | 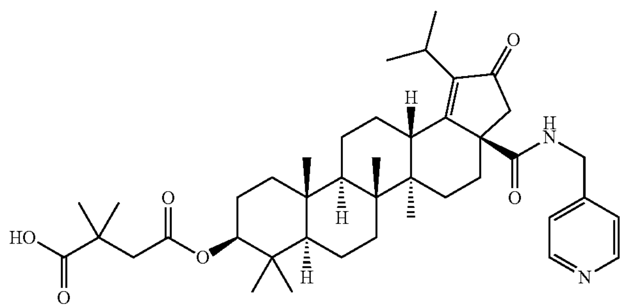 | 3β-O-(3',3'-Dimethylsuccinyl)-21-oxolup-18-en-28-oic acid N-pyridin-4-ylmethylamide | 21.4 (C) | 689.74 |
| 9-19 | 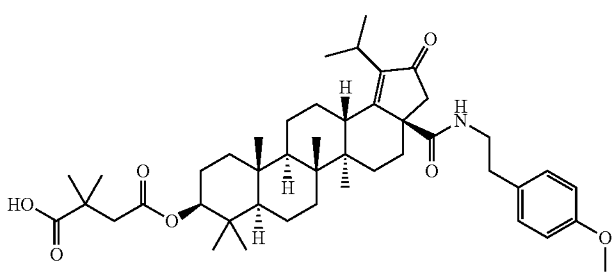 | 3β-O-(3',3'-Dimethylsuccinyl)-21-oxolup-18-en-28-oic acid N-[2-(4-methoxy-phenyl)-ethyl]-acetamide | 34.24 (A) | 732.69 |
| 9-20 | 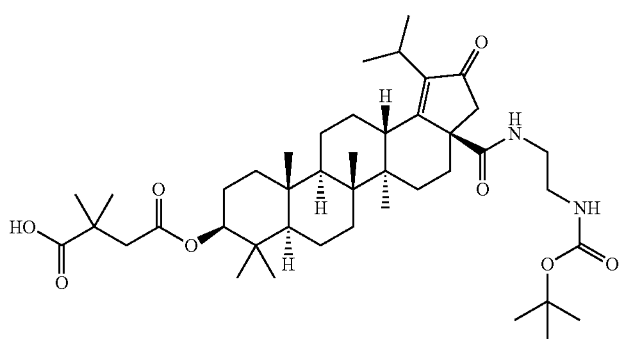 | 3β-O-(3',3'-Dimethylsuccinyl)-21-oxolup-18-en-28-oic acid N-(2-acetylamino-ethyl)-carbamic acid tert-butyl ester | 29.39 (A) | 641.91 (M − Boc) |
| 9-21 | 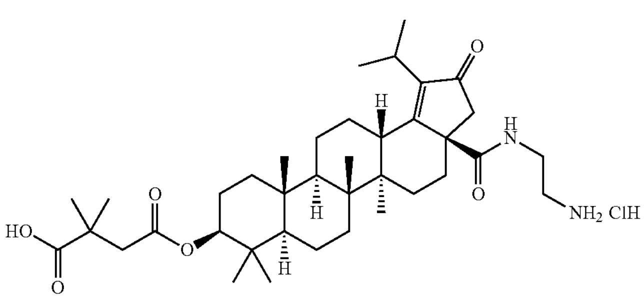 | 3β-O-(3',3'-Dimethylsuccinyl)-21-oxolup-18-en-28-oic acid N-(2-amino-ethyl)-acetamide hydrochloride | 26.23 (D) | 641.68 |

TABLE 3-continued

| Cpd # | Structure | Compound name | t_R (min.) (Method) | M+/M + H+ |
|---|---|---|---|---|
| 9-22 | 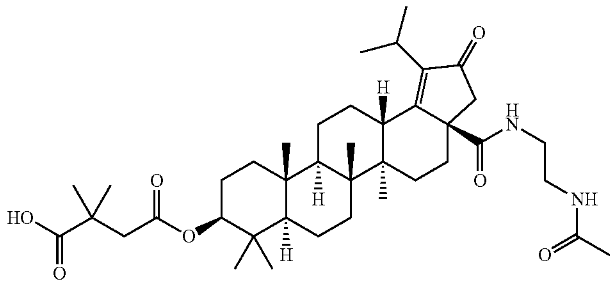 | 3β-O-(3',3'-Dimethylsuccinyl)-21-oxolup-18-en-28-oic acid N-(2-acetylamino-ethyl)-acetamide | 9.60 (B) | 683.50 |
| 9-23 | 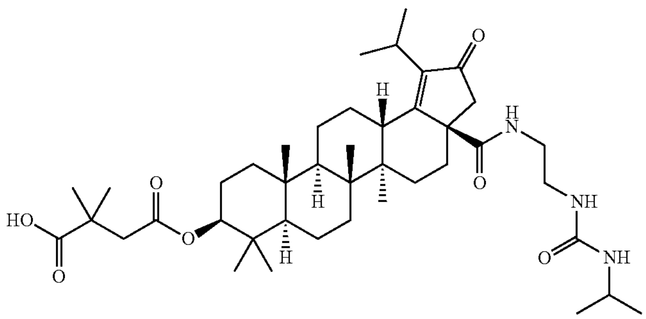 | 3β-O-(3',3'-Dimethylsuccinyl)-21-oxolup-18-en-28-oic acid N-[2-(3-isopropyl-ureido)-ethyl]-acetamide | 12.44 (B) | 726.67 |
| 9-24 | 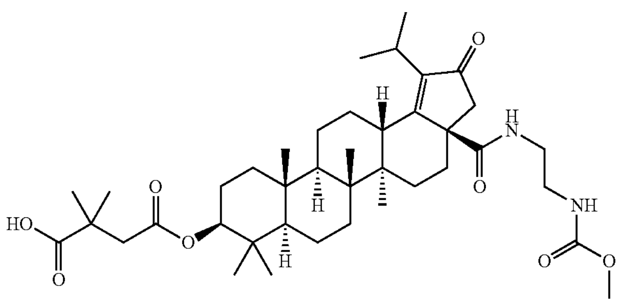 | 3β-O-(3',3'-Dimethylsuccinyl)-21-oxolup-18-en-28-oic acid N-(2-acetylamino-ethyl)-carbamic acid methyl ester | 20.90 (A) | 699.65 |
| 9-25 | 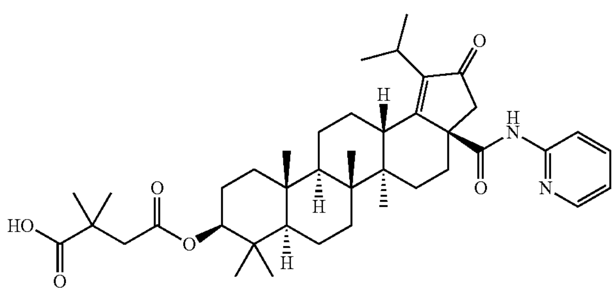 | 3β-O-(3',3'-Dimethylsuccinyl)-21-oxolup-18-en-28-oic acid N-pyridin-2-yl-acetamide | 29.51 (A) | 675.63 |
| 9-26 | 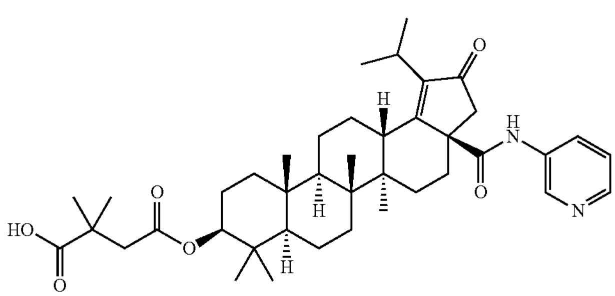 | 3β-O-(3',3'-Dimethylsuccinyl)-21-oxolup-18-en-28-oic acid N-pyridin-3-yl-acetamide | 30.29 (C) | 675.66 |

TABLE 3-continued

| Cpd # | Structure | Compound name | $t_R$ (min.) (Method) | M+/M + H+ |
|---|---|---|---|---|
| 9-27 | 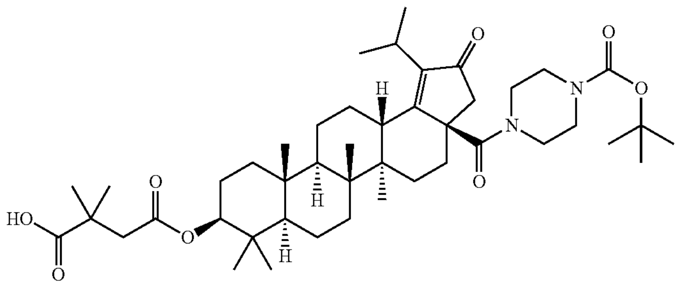 | 3β-O-(3',3'-Dimethylsuccinyl)-21-oxolup-18-en-28-oic acid N-1-acetyl-piperazine-4-carboxylic acid tert-butyl ester | 37.78 (A) | 767.75 |
| 9-28 | 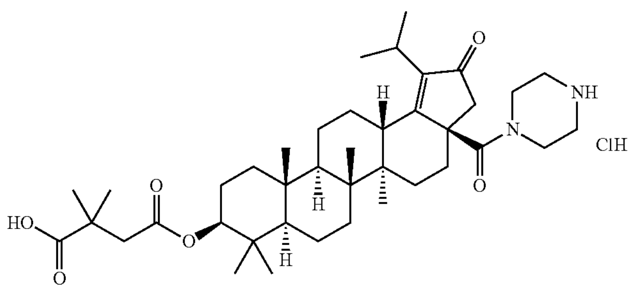 | 3β-O-(3',3'-Dimethylsuccinyl)-21-oxolup-18-en-28-oic acid N-piperazinyl-acetamide hydrochloride | 28.08 (D) | 667.92 |
| 9-29 | 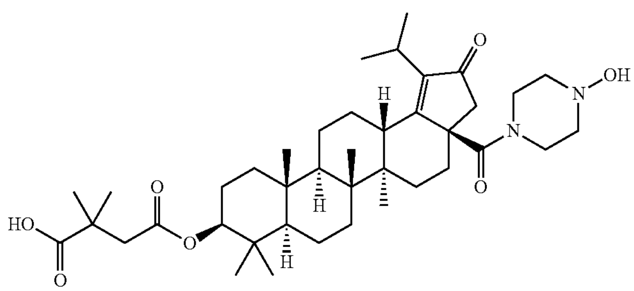 | 3β-O-(3',3'-Dimethylsuccinyl)-21-oxolup-18-en-28-oic acid N-1-(4-hydroxy-piperidin-1-yl)-acetamide | 29.72 (E) | 682.69 |
| 9-30 | 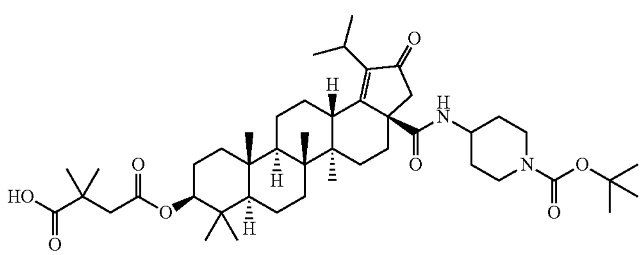 | 3β-O-(3',3'-Dimethylsuccinyl)-21-oxolup-18-en-28-oic acid N-1-acetylamino-piperidine-4-carboxylic acid tert-butyl ester | 36.37 (A) | 681.72 (M − Boc) |
| 9-31 | 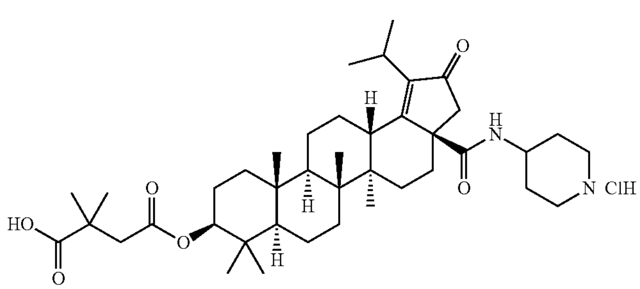 | 3β-O-(3',3'-Dimethylsuccinyl)-21-oxolup-18-en-28-oic acid N-(4-aminopiperidine)-acetamide hydrochloride | 27.23 (D) | 681.61 |

TABLE 3-continued

| Cpd # | Structure | Compound name | $t_R$ (min.) (Method) | M+/M + H+ |
|---|---|---|---|---|
| 9-32 | 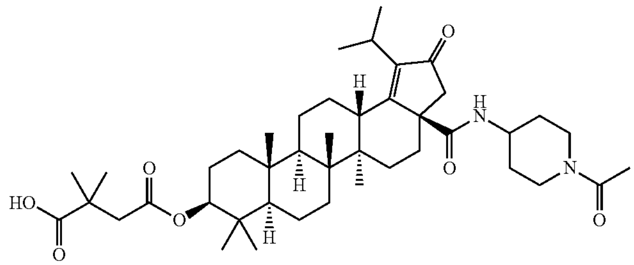 | 3β-O-(3',3'-Dimethylsuccinyl)-21-oxolup-18-en-28-oic acid N-(1-acetyl-4-aminopiperidine)-acetamide | 28.07 (E) | 723.65 |
| 9-33 | 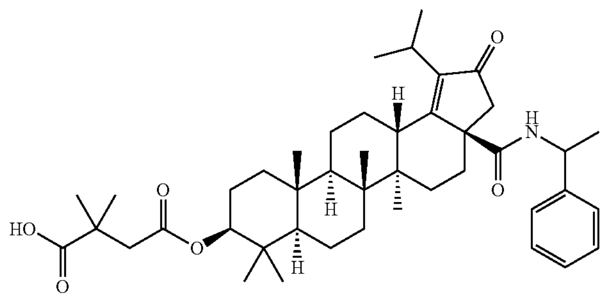 | 3β-O-(3',3'-Dimethylsuccinyl)-21-oxolup-18-en-28-oic acid N-(1-phenyl-ethyl)-acetamide | 37.72 (A) | 702.55 |
| 9-34 | 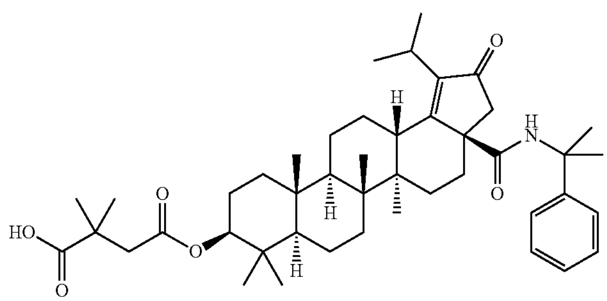 | 3β-O-(3',3'-Dimethylsuccinyl)-21-oxolup-18-en-28-oic acid N-(1-methyl-1-phenyl-ethyl)-acetamide | 41.07 (A) | 716.53 |
| 9-35 | 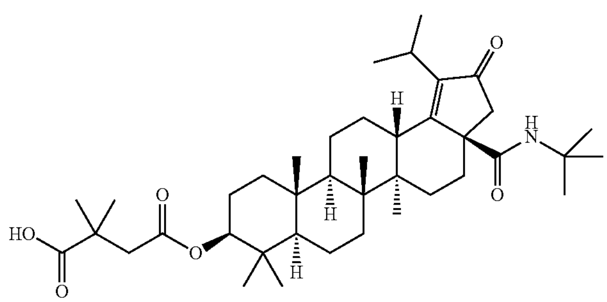 | 3β-O-(3',3'-Dimethylsuccinyl)-21-oxolup-18-en-28-oic acid N-(tert-butyl)-acetamide | 39.85 (A) | 654.59 |
| 9-36 | 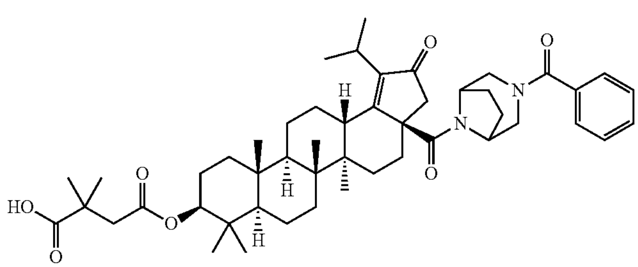 | 3β-O-(3',3'-Dimethylsuccinyl)-21-oxolup-18-en-28-oic acid N-(8-amino-3,8-diaza-bicyclo[3.2.1]octane-3-benzamide)-acetamide | 31.16 (A) | 797.67 |

TABLE 3-continued

| Cpd # | Structure | Compound name | $t_R$ (min.) (Method) | M+/M + H+ |
|---|---|---|---|---|
| 9-37 | 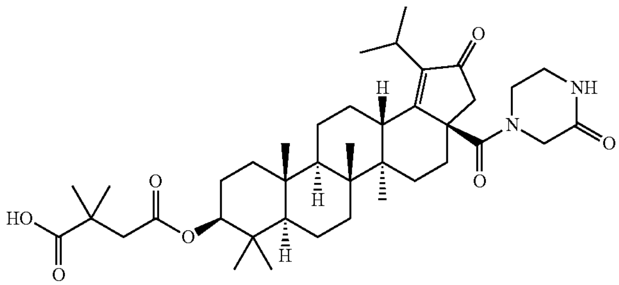 | 3β-O-(3',3'-Dimethylsuccinyl)-21-oxolup-18-en-28-oic acid N-4-piperazi-2-one-acetamide | 4.43 (F) | 681.81 |
| 9-38 | 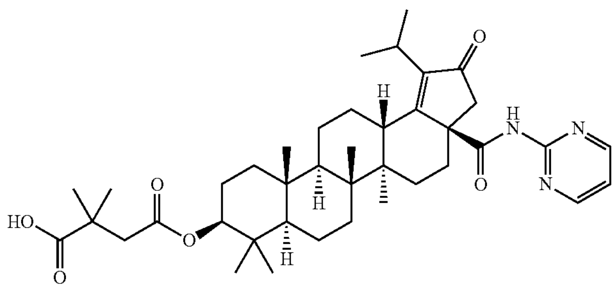 | 3β-O-(3',3'-Dimethylsuccinyl)-21-oxolup-18-en-28-oic acid N-pyrimidin-2-yl-acetamide | 22.09 (A) | 676.54 |
| 9-39 | 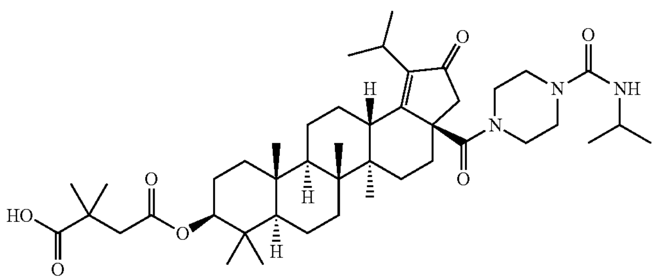 | 3β-O-(3',3'-Dimethylsuccinyl)-21-oxolup-18-en-28-oic acid N-(4-N'-isopropylureido-1-piperazine)-acetamide | 24.34 (A) | 752.70 |
| 9-40 | 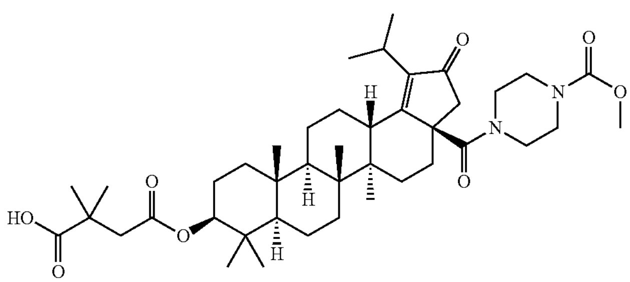 | 3β-O-(3',3'-Dimethylsuccinyl)-21-oxolup-18-en-28-oic acid N-1-acetyl-piperazine-4-carboxylic acid methyl ester | 27.92 (A) | 726.03 |
| 9-41 | 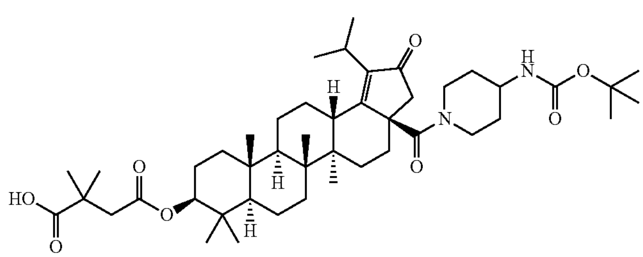 | 3β-O-(3',3'-Dimethylsuccinyl)-21-oxolup-18-en-28-oic acid N-(4-amino carboxylic acid tert-butyl-ester-1-piperidine)-acetamide | | $^1$H NMR (400 MHz, CDCl$_3$): δ [ppm] 4.49 (m, 3H), 3.65 (m, 1H), 3.16 (m, 1H), 3.07-2.60 (m, 6H), 2.68 (d, 1H), 2.56 (d, 1H), 2.43 (d, 1H), 2.22 (d, 1H), 2.15-1.83 (m, 8H), 1.76-1.55 (m, 9H), 1.52-1.47 (m, 1H), 1.42 (s, 9H), 1.29 (s, 3H), 1.28 (s, 3H), 1.22 (d, 3H), 1.37-1.16 (m, 3H), 1.13 (d, 3H), 0.99 (s, 3H), 0.95 (m, 3H), 0.88 (s, 3H), 0.83 (s, 3H), 0.80 (s, 3H) |

TABLE 3-continued

| Cpd # | Structure | Compound name | t_R (min.) (Method) | M+/M + H+ |
|---|---|---|---|---|
| 9-42 | 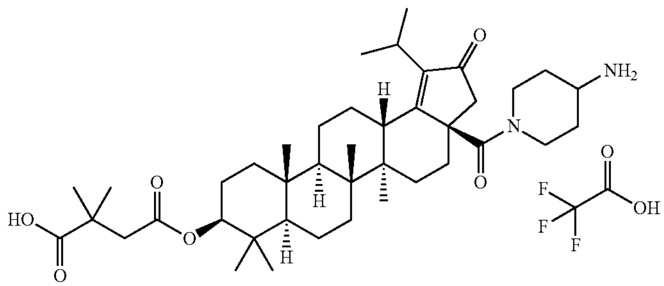 | 3β-O-(3',3'-Dimethylsuccinyl)-21-oxolup-18-en-28-oic acid N-(4-amino-1-piperidine)-acetamide trifluoroacetic acid | 17.47 (C) | 681.83 |
| 9-43 | 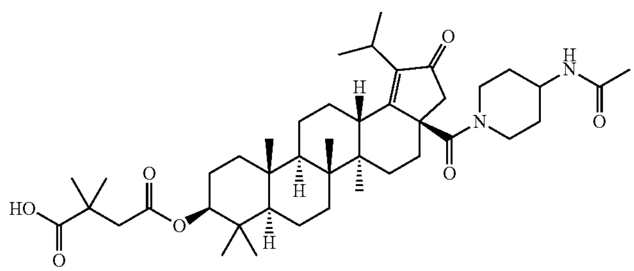 | 3β-O-(3',3'-Dimethylsuccinyl)-21-oxolup-18-en-28-oic acid N-(4-acetylamino-1-piperidine)-acetamide | 5.23 (F) | N |
| D£ 9-44 | 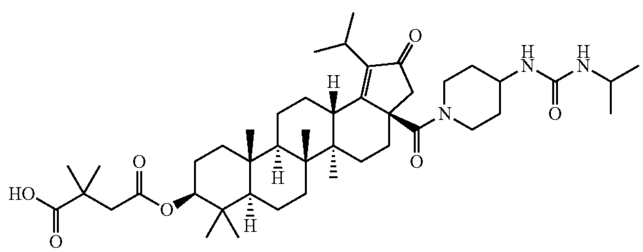 | 3β-O-(3',3'-Dimethylsuccinyl)-21-oxolup-18-en-28-oic acid N-[(4-amino-N'-isopropylureido)-1-piperidine]-acetamide | 32.19 (E) | 767.33 |
| 9-45 | 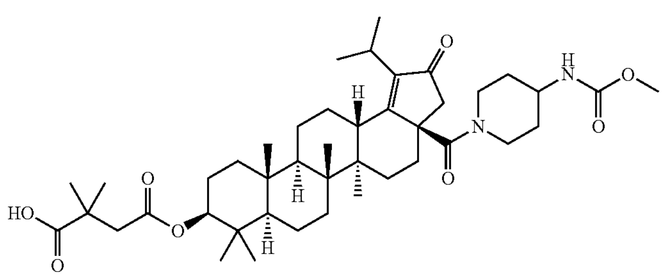 | 3β-O-(3',3'-Dimethylsuccinyl)-21-oxolup-18-en-28-oic acid N-(4-amino carboxylic acid methyl ester-1-piperidine)-acetamide | 34.86 (E) | 740.09 |
| 9-46 | 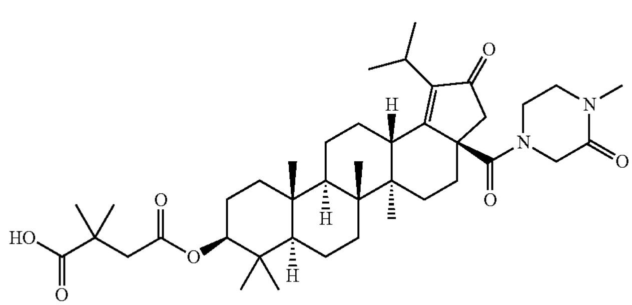 | 3β-O-(3',3'-Dimethylsuccinyl)-21-oxolup-18-en-28-oic acid N-(4-(1-methyl-piperazi-2-one)-acetamide | 29.21 (E) | 695.85 |

TABLE 3-continued

| Cpd # | Structure | Compound name | $t_R$ (min.) (Method) | M+/M + H+ |
|---|---|---|---|---|
| 9-47 | 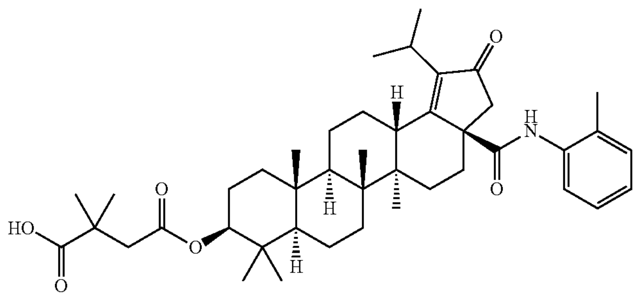 | 3β-O-(3',3'-Dimethylsuccinyl)-21-oxolup-18-en-28-oic acid N-2-methyl-phen-1-yl acetamide | 36.94 (A) | 688.89 |
| 9-48 | 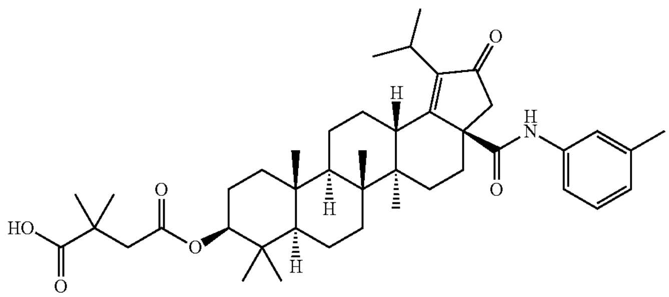 | 3β-O-(3',3'-Dimethylsuccinyl)-21-oxolup-18-en-28-oic acid N-3-methyl-phen-1-yl acetamide | 39.06 (A) | 688.81 |
| 9-49 | 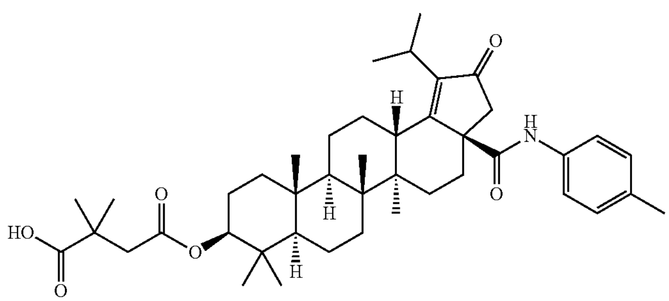 | 3β-O-(3',3'-Dimethylsuccinyl)-21-oxolup-18-en-28-oic acid N-4-methyl-phen-1-yl acetamide | 38.63 (A) | 688.81 |
| 9-50 | 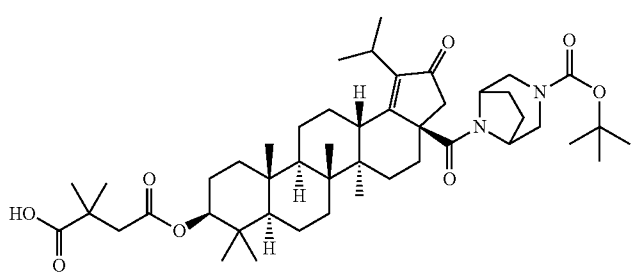 | 3β-O-(3',3'-Dimethylsuccinyl)-21-oxolup-18-en-28-oic acid N-8-acetylamino-3,8-diaza-bicyclo[3.2.1]octane-3-carboxylic acid tert-butyl ester | 30.02 (B) | ND |
| 9-51 | 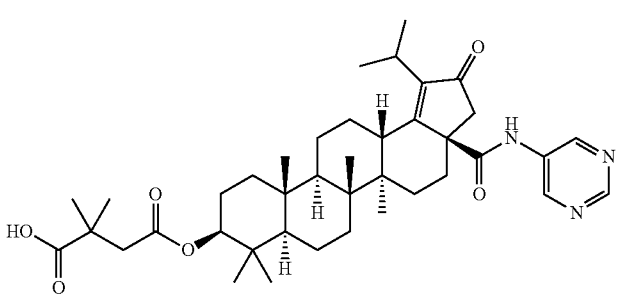 | 3β-O-(3',3'-Dimethylsuccinyl)-21-oxolup-18-en-28-oic acid N-pyrimidin-5-yl-acetamide | 24.8 (A) | 676.79 |

TABLE 3-continued

| Cpd # | Structure | Compound name | t_R (min.) (Method) | M+/M + H+ |
|---|---|---|---|---|
| 9-52 | 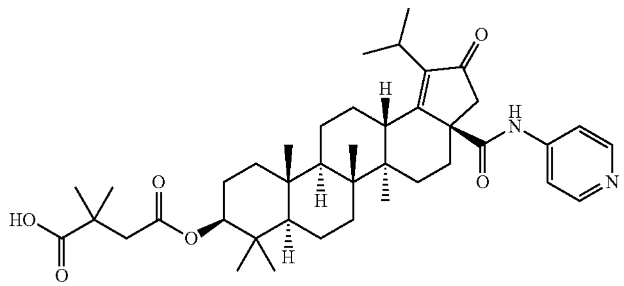 | 3β-O-(3',3'-Dimethylsuccinyl)-21-oxolup-18-en-28-oic acid N-pyridin-4-yl-acetamide | 22.21 (C) | 675.72 |
| 9-53 | 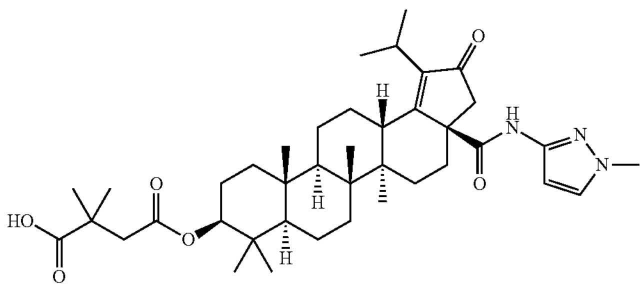 | 3β-O-(3',3'-Dimethylsuccinyl)-21-oxolup-18-en-28-oic acid N-3-amino-1-methyl-1H-pyrazole-acetamide | 26.79 (A) | 678.74 |
| 9-54 | 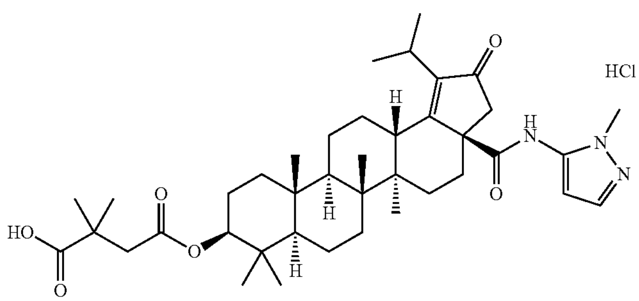 | 3β-O-(3',3'-Dimethylsuccinyl)-21-oxolup-18-en-28-oic acid N-5-amino-1-methyl-1H-pyrazole acetamide hydrochloride | 6.77 (F) | 678.59 |
| 9-55 | 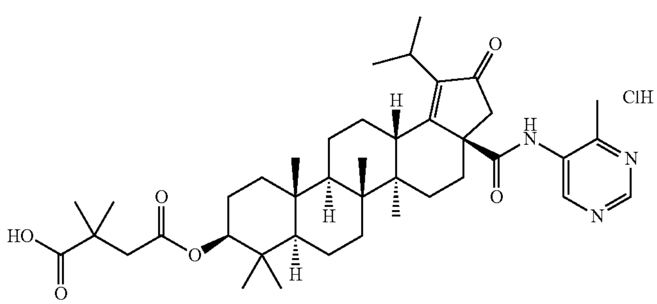 | 3β-O-(3',3'-Dimethylsuccinyl)-21-oxolup-18-en-28-oic acid N-4-methyl-pyrimidin-5-yl-acetamide hydrochloride | 23.92 (A) | 690.78 |
| 9-56 | 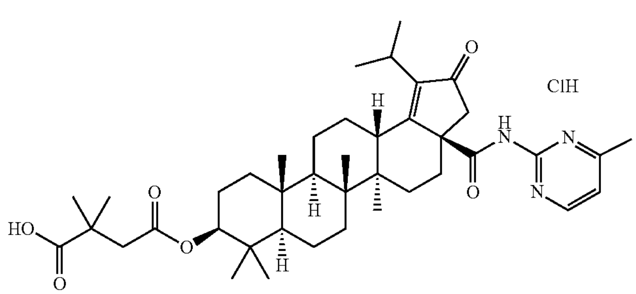 | 3β-O-(3',3'-Dimethylsuccinyl)-21-oxolup-18-en-28-oic acid N-4-methyl-pyrimidin-2-yl-acetamide hydrochloride | 24.1 (A) | 690.77 |

TABLE 3-continued

| Cpd # | Structure | Compound name | $t_R$ (min.) (Method) | M+/M + H+ |
|---|---|---|---|---|
| 9-57 | 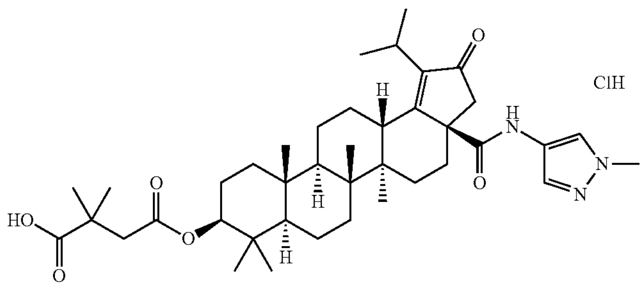 | 3β-O-(3',3'-Dimethylsuccinyl)-21-oxolup-18-en-28-oic acid N-4-amino-1-methyl-1H-pyrazole acetamide hydrochloride | 23.1 (A) | 678.67 |
| 9-58 | 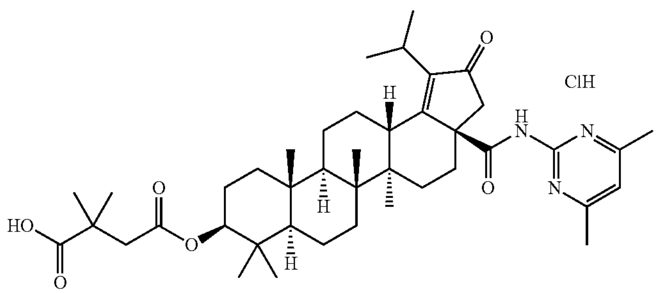 | 3β-O-(3',3'-Dimethylsuccinyl)-21-oxolup-18-en-28-oic acid N-4,6-dimethyl-pyrimidin-2-yl-acetamide hydrochloride | 26.18 (A) | 704.83 |
| 9-59 | 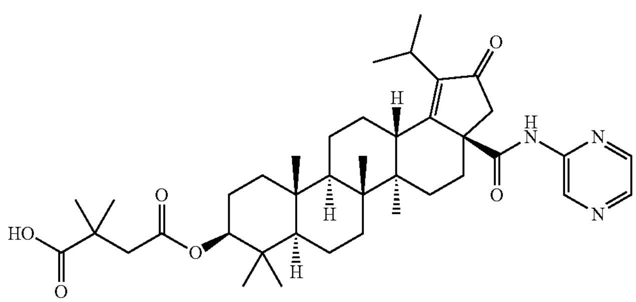 | 3β-O-(3',3'-Dimethylsuccinyl)-21-oxolup-18-en-28-oic acid N-pyrazin-2-yl-acetamide | 30.74 (A) | 676.67 |
| 9-60 | 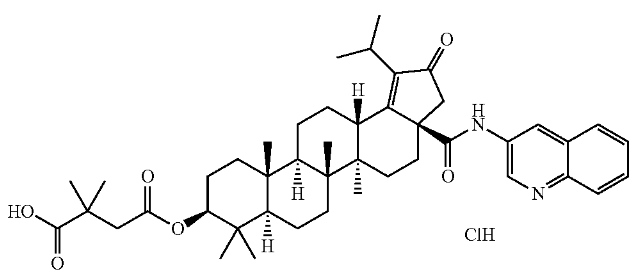 | 3β-O-(3',3'-Dimethylsuccinyl)-21-oxolup-18-en-28-oic acid N-quinolin-3-yl-acetamide hydrochloride | 11.63 (G) | 724.99 |
| 9-61 | 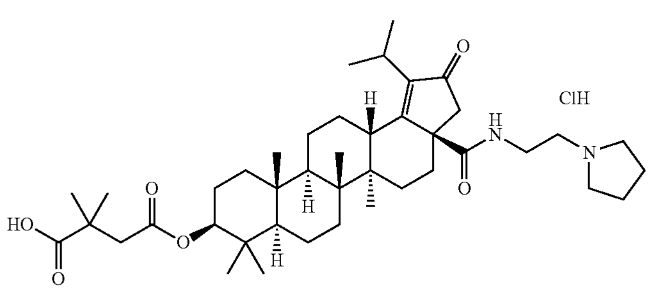 | 3β-O-(3',3'-Dimethylsuccinyl)-21-oxolup-18-en-28-oic acid N-(2-pyrrolidin-1-yl-ethyl)-acetamide hydrochloride | 19.22 (C) | 695.83 |

TABLE 3-continued

| Cpd # | Structure | Compound name | $t_R$ (min.) (Method) | M+/M + H+ |
|---|---|---|---|---|
| 9-62 | 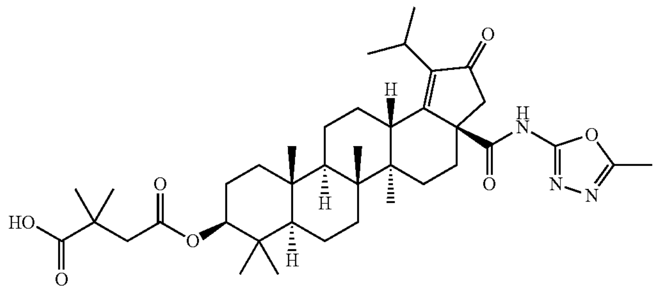 | 3β-O-(3',3'-Dimethylsuccinyl)-21-oxolup-18-en-28-oic acid N-(5-methyl-[1,3,4]oxadiazol-2-yl)-acetamide | 9.28 (G) | 680.69 |
| 9-63 | 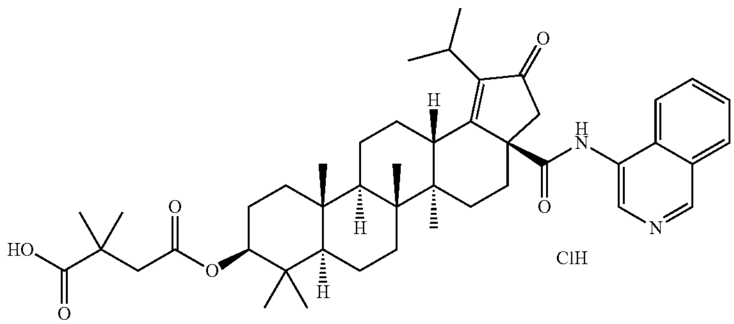 | 3β-O-(3',3'-Dimethylsuccinyl)-21-oxolup-18-en-28-oic acid N-isoquinolin-4-yl-acetamide hydrochloride | 8.37 (G) | 725.99 |
| 9-64 | 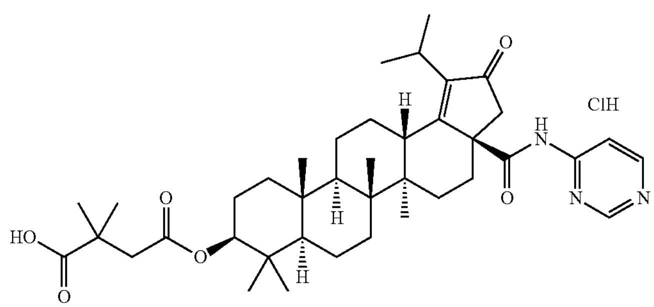 | 3β-O-(3',3'-Dimethylsuccinyl)-21-oxolup-18-en-28-oic acid N-pyrimidin-4-yl-acetamide hydrochloride | 11.25 (G) | 676.68 |
| 9-65 | 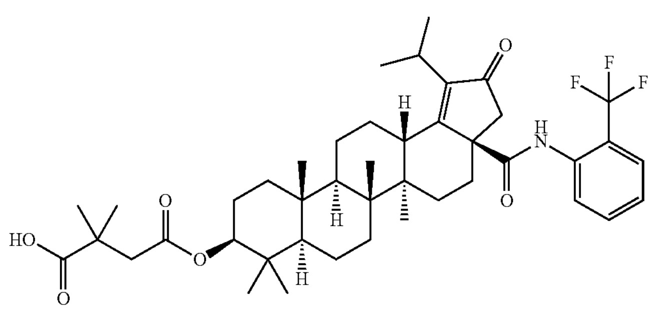 | 3β-O-(3',3'-Dimethylsuccinyl)-21-oxolup-18-en-28-oic acid N-2-trifluoromethyl-phen-1-yl acetamide | 31.23 (B) | 742.4 |
| 9-66 | 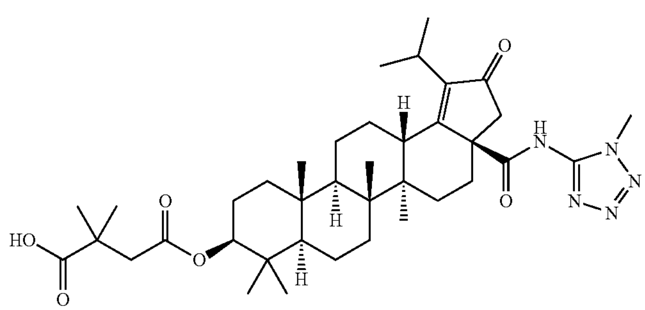 | 3β-O-(3',3'-Dimethylsuccinyl)-21-oxolup-18-en-28-oic acid N-(1-methyl-1H-tetrazol-5-yl)-acetamide | 24.28 (A) | 680.76 |

TABLE 3-continued

| Cpd # | Structure | Compound name | t_R (min.) (Method) | M+/M + H+ |
|---|---|---|---|---|
| 9-67 | 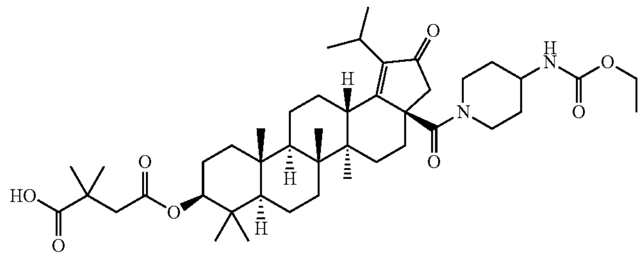 | 3β-O-(3',3'-Dimethylsuccinyl)-21-oxolup-18-en-28-oic acid N-(4-amino carboxylic acid ethyl ester-1-piperidine)-acetamide | 19.22 (B) | 754.17 |
| 9-68 | 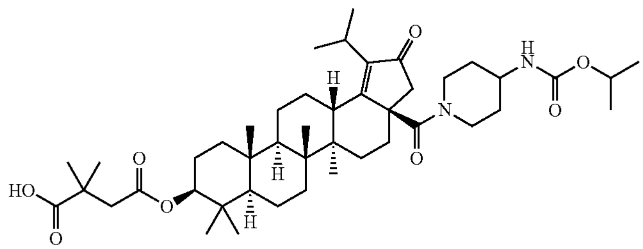 | 3β-O-(3',3'-Dimethylsuccinyl)-21-oxolup-18-en-28-oic acid N-(4-amino carboxylic acid isopropyl ester-1-piperidine)-acetamide | 21.61 (B) | 768.33 |
| 9-69 | 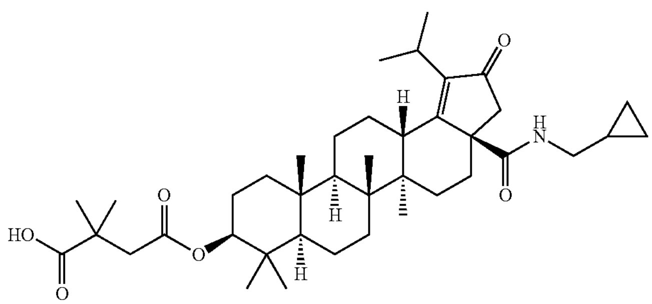 | 3β-O-(3',3'-Dimethylsuccinyl)-21-oxolup-18-en-28-oic acid N-cyclopropylmethyl acetamide | 22.90 (B) | 652.69 |
| 9-70 | 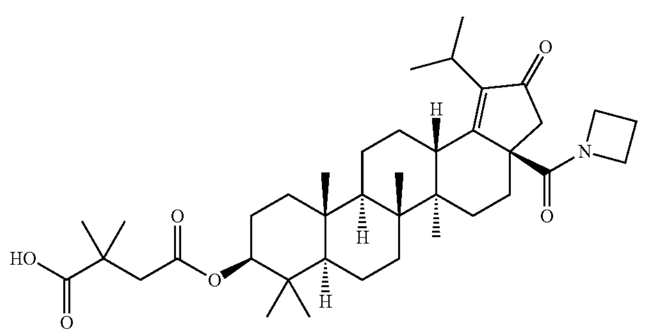 | 3β-O-(3',3'-Dimethylsuccinyl)-21-oxolup-18-en-28-oic acid N-azetidine-1 acetamide | 18.56 (B) | 638.61 |
| 9-71 | 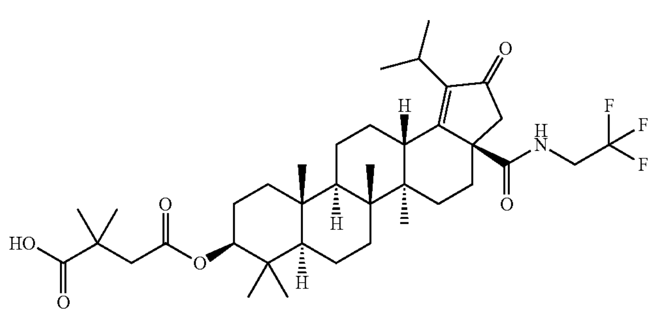 | 3β-O-(3',3'-Dimethylsuccinyl)-21-oxolup-18-en-28-oic acid N-(2,2,2-trifluoro-ethyl)-acetamide | 31.30 (A) | 680.80 |

TABLE 3-continued

| Cpd # | Structure | Compound name | $t_R$ (min.) (Method) | M+/M + H+ |
|---|---|---|---|---|
| 9-72 | 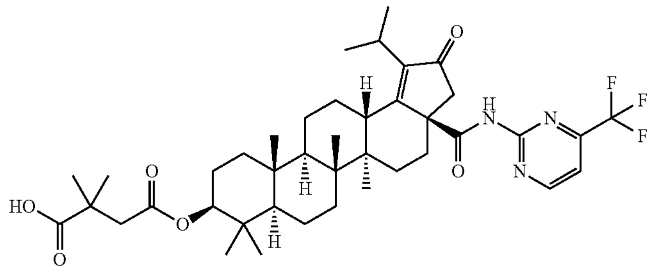 | 3β-O-(3',3'-Dimethylsuccinyl)-21-oxolup-18-en-28-oic acid N-4-trifluoro-pyrimidin-2-yl-acetamide | 31.62 (A) | 745.18 |
| 9-73 | 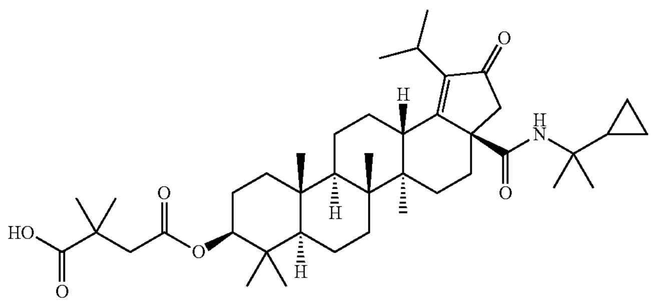 | 3β-O-(3',3'-Dimethylsuccinyl)-21-oxolup-18-en-28-oic acid N-(1-cyclopropyl-1-methyl-ethyl)-acetamide | 32.56 (B) | 680.83 |
| 9-74 | 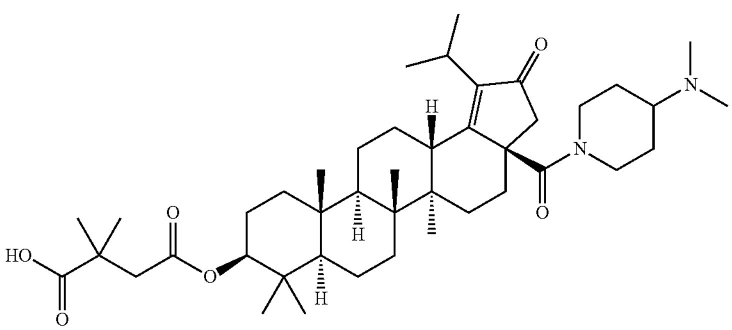 | 3β-O-(3',3'-Dimethylsuccinyl)-21-oxolup-18-en-28-oic acid N-(4-dimethylamino-piperidin-1-yl)-acetamide | 19.42 (C) | 710.01 |
| 9-75 | 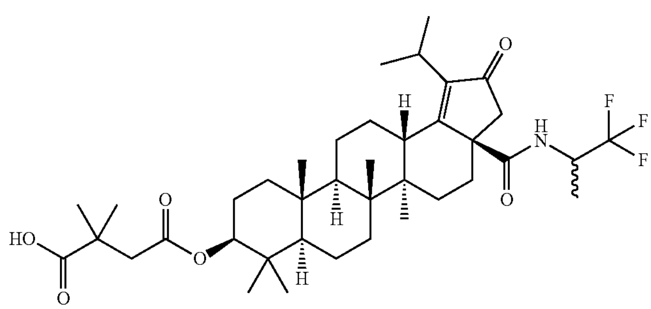 | 3β-O-(3',3'-Dimethylsuccinyl)-21-oxolup-18-en-28-oic acid N-(2,2,2-trifluoro-1-methyl-ethyl)-acetamide | 11.6 (H) | 694.88 |
| 9-76 | 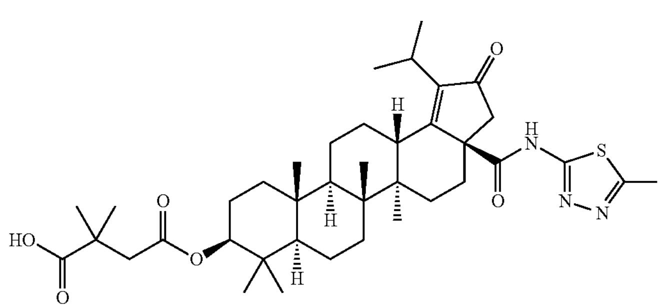 | 3β-O-(3',3'-Dimethylsuccinyl)-21-oxolup-18-en-28-oic acid N-(5-methyl-[1,3,4]thiadiazol-2-yl)-acetamide | 9.01 (H) | 696.92 |

TABLE 3-continued

| Cpd # | Structure | Compound name | t_R (min.) (Method) | M+/M + H+ |
|---|---|---|---|---|
| 9-77 | 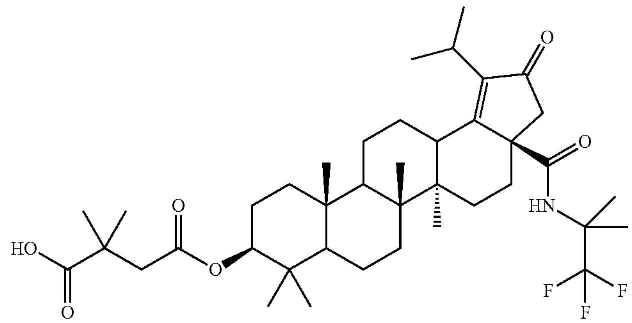 | 3β-O-(3',3'-Dimethylsuccinyl)-21-oxolup-18-en-28-oic acid N-(2,2,2-trifluoro-1,1-dimethyl-ethyl)-acetamide | 30.11 (B) | 709.02 |
| 9-78 | 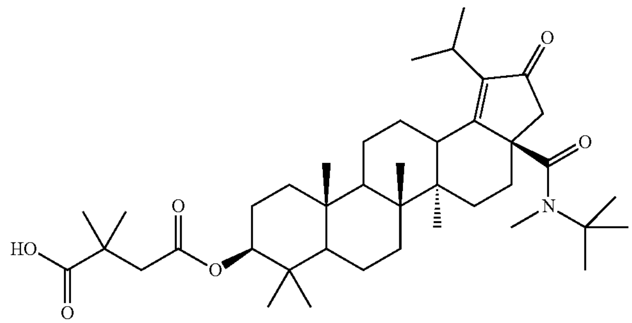 | 3β-O-(3',3'-Dimethylsuccinyl)-21-oxolup-18-en-28-oic acid N-tert-butyl-N-methyl-acetamide | 14.91 (H) | 668.76 |
| 9-79 | 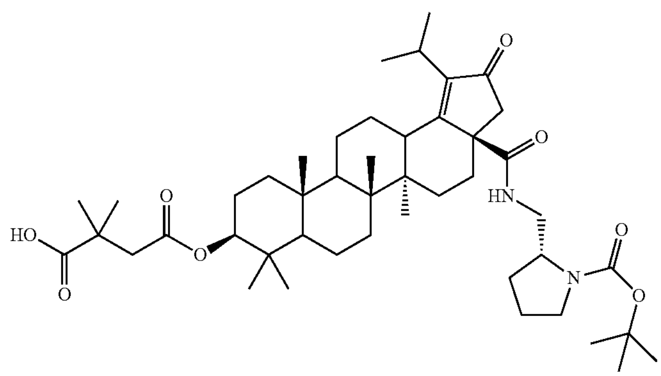 | 3β-O-(3',3'-Dimethylsuccinyl)-21-oxolup-18-en-28-oic acid N-(R)-2-acetylaminomethyl-pyrrolidine-1-carboxylic acid tert-butyl ethyl | 1H NMR (400 MHz, CDCl$_3$): δ [ppm] 7.50 (m, 1H), 4.49 (m, 1H), 3.81 (m, 1H), 3.58 (m, 1H), 3.38 (m, 1H), 3.25 (m, 2H), 3.01 (m, 1H), 2.80 (br d, 1H), 2.61 (m, 3H), 2.37 (d, 1H), 2.07 (m, 3H), 1.45 (m, 35H), 0.99 (m, 4H), 0.81 (m, 1H) | |
| 9-80 | 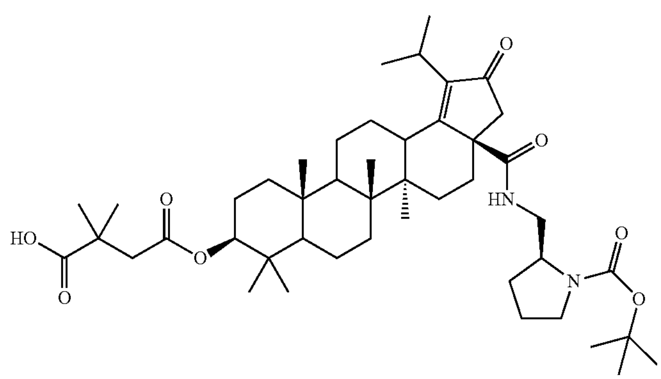 | 3β-O-(3',3'-Dimethylsuccinyl)-21-oxolup-18-en-28-oic acid N-(S)-2-acetylaminomethyl-pyrrolidine-1-carboxylic acid tert-butyl ethyl | 1H NMR (400 MHz, CDCl$_3$): δ [ppm] 7.41 (m, 1H), 4.48 (d × d, 1H), 3.74 (m, 1H), 3.57 (m, 1H), 3.92 (m, 1H), 3.24 (m, 2H), 3.06 (m, 1H), 2.71 (br d, 1H), 2.60 (m, 3H), 2.40 (d, 1H), 2.04 (m, 3H), 1.73 (m, 9H), 1.46 (m, 14H), 1.26 (m, 15H), 0.86 (m, 2H) | |

TABLE 3-continued

| Cpd # | Structure | Compound name | $t_R$ (min.) (Method) | M+/M + H+ |
|---|---|---|---|---|
| 9-81 | 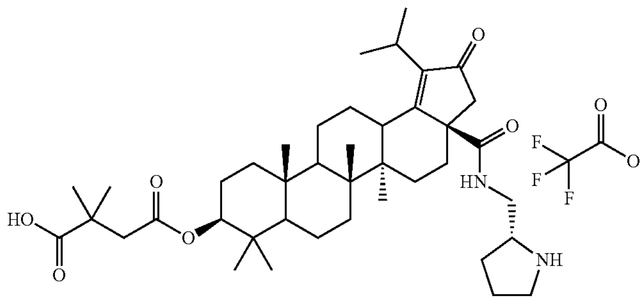 | 3β-O-(3',3'-Dimethylsuccinyl)-21-oxolup-18-en-28-oic acid N-((R)-1-pyrrolidin-2-ylmethyl)-acetamide trifluoroacetic acid | 18.71 (C) | 681.92 |
| 9-82 | 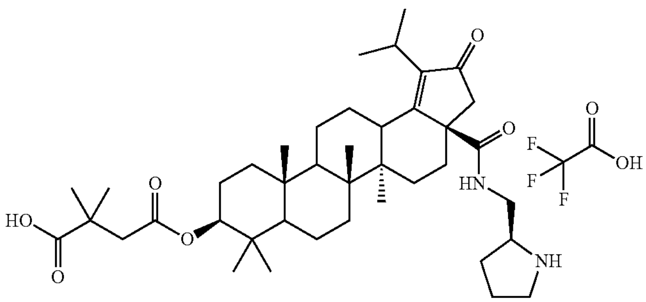 | 3β-O-(3',3'-Dimethylsuccinyl)-21-oxolup-18-en-28-oic acid N-((S)-1-pyrrolidin-2-ylmethyl)-acetamide trifluoroacetic acid | 18.60 (C) | 681.93 |
| 9-83 | 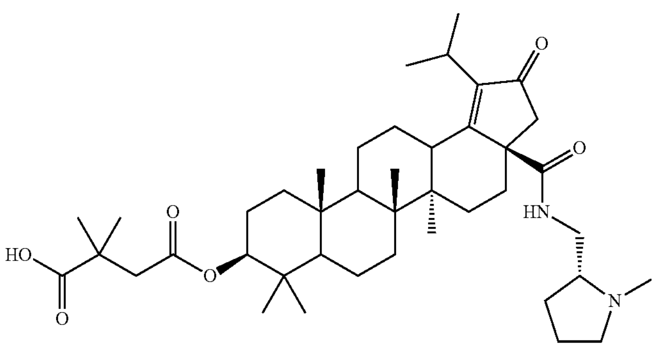 | 3β-O-(3',3'-Dimethylsuccinyl)-21-oxolup-18-en-28-oic acid N-((R)-1-methyl-pyrrolidin-2-ylmethyl)-acetamide | 19.04 (C) | 695.99 |
| 9-84 | 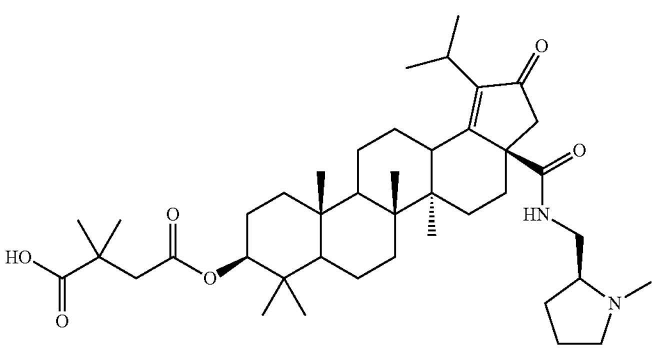 | 3β-O-(3',3'-Dimethylsuccinyl)-21-oxolup-18-en-28-oic acid N-((S)-1-methyl-pyrrolidin-2-ylmethyl)-acetamide | 19.01 (C) | 696 |

TABLE 3-continued

| Cpd # | Structure | Compound name | $t_R$ (min.) (Method) | M+/M + H+ |
|---|---|---|---|---|
| 9-85 | 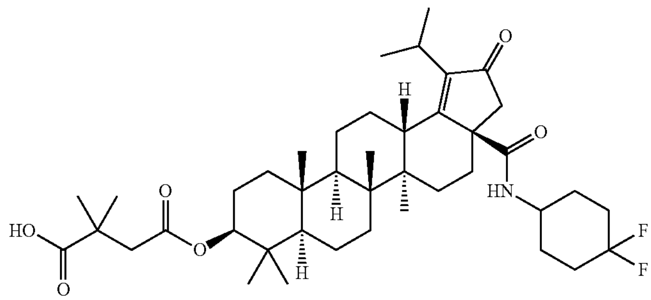 | 3β-O-(3',3'-Dimethylsuccinyl)-21-oxolup-18-en-28-oic acid N-(4,4-difluoro-cyclohexyl) acetamide | 11.57 (H) | 717.11 |
| 9-86 | 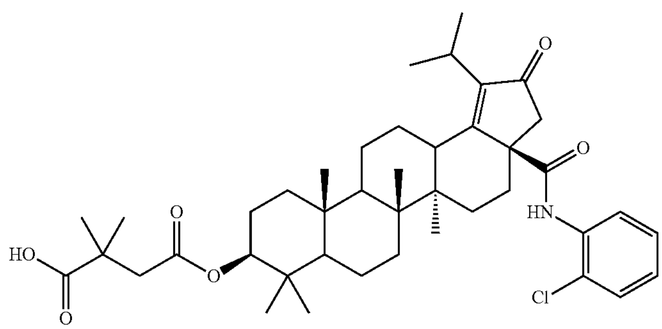 | 3β-O-(3',3'-Dimethylsuccinyl)-21-oxolup-18-en-28-oic acid N-2-chloro-phen-1-yl acetamide | 15.20 (H) | 708.92 |
| 9-87 | 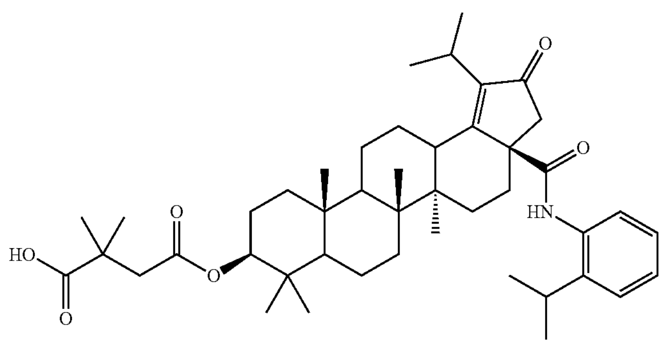 | 3β-O-(3',3'-Dimethylsuccinyl)-21-oxolup-18-en-28-oic acid N-2-isopropyl-phen-1-yl acetamide | 14.11 (H) | 717.05 |
| 9-88 | 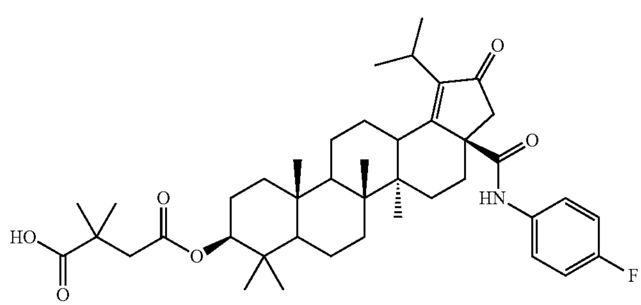 | 3β-O-(3',3'-Dimethylsuccinyl)-21-oxolup-18-en-28-oic acid N-4-fluoro-phen-1-yl acetamide | 35.60 (A) | 693 |
| 9-89 | 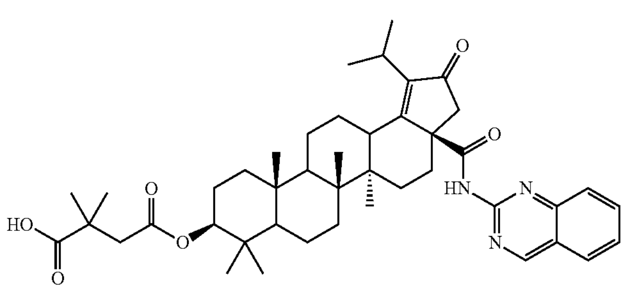 | 3β-O-(3',3'-Dimethylsuccinyl)-21-oxolup-18-en-28-oic acid N-quinazolin-2-yl acetamide | 29.02 (A) | 727.08 |

TABLE 3-continued

| Cpd # | Structure | Compound name | t_R (min.) (Method) | M+/M + H+ |
|---|---|---|---|---|
| 9-90 | 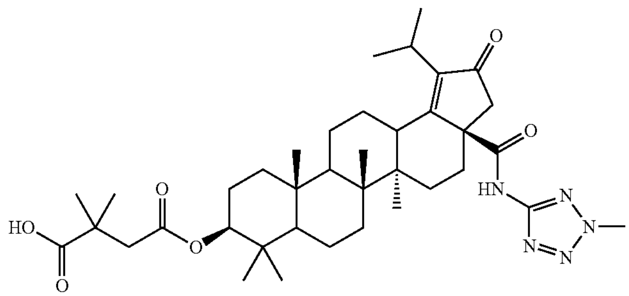 | 3β-O-(3',3'-Dimethylsuccinyl)-21-oxolup-18-en-28-oic acid N-(1-methyl-1H-tetrazol-3-yl)-acetamide | 31.85 (E) | 680.80 |
| 9-91 | 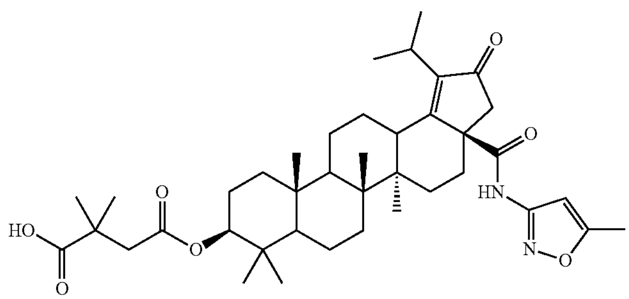 | 3β-O-(3',3'-Dimethylsuccinyl)-21-oxolup-18-en-28-oic acid N-(5-methyl-isoxazol-3-yl)-acetamide | 11.36 (H) | 679.81 |
| 9-92 | 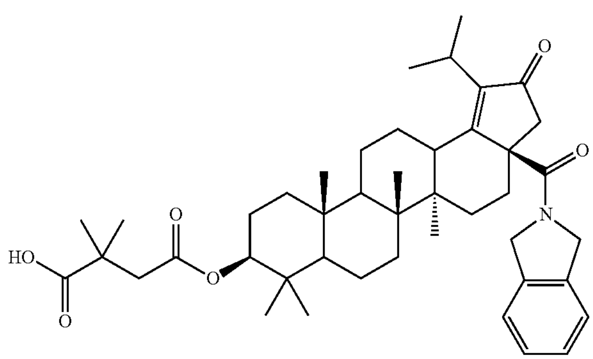 | 3β-O-(3',3'-Dimethylsuccinyl)-21-oxolup-18-en-28-oic acid N-(1,3-dihydro-isoindol-2-yl)-acetamide | 13.17 (H) | 701.07 |
| 9-93 | 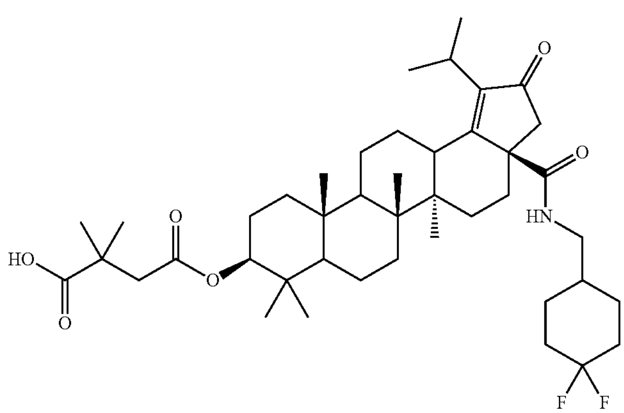 | 3β-O-(3',3'-Dimethylsuccinyl)-21-oxolup-18-en-28-oic acid N-(4,4-difluoro-cyclohexylmethyl)-acetamide | 11.6 (H) | 731.22 |

TABLE 3-continued

| Cpd # | Structure | Compound name | $t_R$ (min.) (Method) | M+/M + H+ |
|---|---|---|---|---|
| 9-94 | 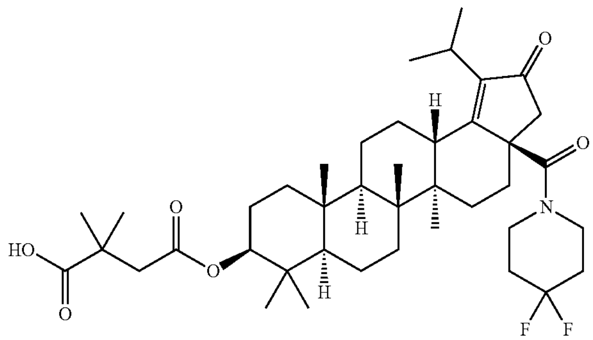 | 3β-O-(3',3'-Dimethylsuccinyl)-21-oxolup-18-en-28-oic acid N-4,4-difluoro-piperidine acetamide | 12.24 (H) | 703.02 |
| 9-95 | 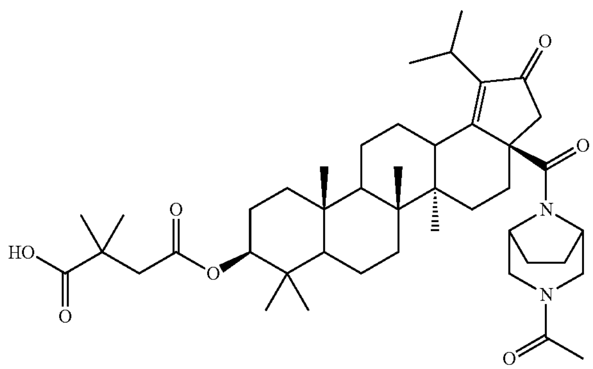 | 3β-O-(3',3'-Dimethylsuccinyl)-21-oxolup-18-en-28-oic acid N-8-acetylamino-3,8-diaza-bicyclo[3.2.1]octane-3-acetamide | 31.4 (E) | 736.20 |

HIV Replication Activity

HIV-1 Replication in MT2 cell line with and without 30% human serum: The cells are infected at a Multiciplicity of Infection (MOI) of 0.5 for 3 h and then washed twice with complete media to remove residual virus. Cells are then resuspended at $0.5 \times 10^6$/ml in complete medium (RPMI, 10% FBS, 1% sodium pyruvate), and seeded into 96-well plates ($6.25 \times 10^4$/well). The cells are cultured in the presence or absence of various concentrations of test compounds in serial dilutions for 3 days at 37° C. The test compounds are serially diluted in complete medium supplemented or not with 30% human serum. After 3 days, 100 μL of cultured medium with cells are replaced with 120 μL of freshly diluted test compounds in complete medium containing or not 30% Human serum. The level of HIV-1 replication is determined at days 5 after infection by the presence of viral RT activity in harvested supernatant fluid. The $IC_{50}$ and $IC_{90}$ values for the virus replication are determined by using GRAPHPAD PRISM software.

The $IC_{50}$ of the compounds tested in accordance with the HIV replication activity assay MT-2 ($HIV_{IIIB}$) are represented in Table 4 (without HS) and Table 5 (with 30% HS)

TABLE 4

| Cpd # | MT-2 ($HIV_{IIIB}$) $IC_{50}$ range |
|---|---|
| 9-1 | +++ |
| 9-2 | +++ |
| 9-3 | +++ |
| 9-4 | +++ |
| 9-5 | +++ |
| 9-13 | +++ |
| 9-19 | +++ |

TABLE 5

| Cpd # | MT-2 ($HIV_{IIIB}$) with 30% HS $IC_{50}$ range | Cpd # | MT-2 ($HIV_{IIIB}$) with 30% HS $IC_{50}$ range |
|---|---|---|---|
| 9-6 | +++ | 9-52 | +++ |
| 9-7 | +++ | 9-53 | +++ |
| 9-8 | +++ | 9-54 | +++ |
| 9-9 | +++ | 9-55 | +++ |
| 9-10 | +++ | 9-56 | +++ |
| 9-11 | +++ | 9-57 | +++ |
| 9-12 | +++ | 9-58 | +++ |
| 9-14 | +++ | 9-59 | +++ |
| 9-15 | +++ | 9-60 | +++ |
| 9-16 | +++ | 9-61 | +++ |
| 9-17 | +++ | 9-62 | ++ |
| 9-18 | +++ | 9-63 | +++ |
| 9-20 | +++ | 9-64 | +++ |
| 9-21 | +++ | 9-65 | +++ |
| 9-22 | +++ | 9-66 | ++ |
| 9-23 | +++ | 9-67 | +++ |
| 9-24 | +++ | 9-68 | +++ |
| 9-25 | +++ | 9-69 | +++ |
| 9-26 | +++ | 9-70 | +++ |
| 9-27 | +++ | 9-71 | +++ |
| 9-28 | +++ | 9-72 | +++ |
| 9-29 | +++ | 9-73 | +++ |
| 9-30 | +++ | 9-74 | +++ |
| 9-31 | ++ | 9-75 | +++ |

TABLE 5-continued

| Cpd # | MT-2 (HIV$_{IIIB}$) with 30% HS IC$_{50}$ range | Cpd # | MT-2 (HIV$_{IIIB}$) with 30% HS IC$_{50}$ range |
|---|---|---|---|
| 9-32 | +++ | 9-76 | +++ |
| 9-33 | +++ | 9-77 | +++ |
| 9-34 | +++ | 9-78 | +++ |
| 9-35 | +++ | 9-79 | +++ |
| 9-36 | +++ | 9-80 | +++ |
| 9-37 | +++ | 9-81 | +++ |
| 9-38 | +++ | 9-82 | +++ |
| 9-39 | +++ | 9-83 | +++ |
| 9-40 | +++ | 9-84 | +++ |
| 9-41 | +++ | 9-85 | +++ |
| 9-42 | +++ | 9-86 | +++ |
| 9-43 | +++ | 9-87 | ++ |
| 9-44 | +++ | 9-88 | +++ |
| 9-45 | +++ | 9-89 | +++ |
| 9-46 | +++ | 9-90 | +++ |
| 9-47 | +++ | 9-91 | +++ |
| 9-48 | +++ | 9-92 | +++ |
| 9-49 | +++ | 9-93 | +++ |
| 9-50 | +++ | 9-94 | +++ |
| 9-51 | +++ | 9-95 | +++ |

When the compounds are tested more than once, the average IC$_{50}$ is provided.

MT2 (HIV$_{IIIB}$) IC50

+ >1000 nM

++ 200-999 nM

+++ <199 nM

PBMCs are separated from healthy donors' blood by standard density gradient centrifugation, resuspended at a cell density of 1.5×10$^6$ cells/ml in culture medium containing 2 µg/mL of phytohaemagglutinin (PHA), and thereafter incubated for 3 days at 37° C. in a humidified 5% CO$_2$ atmosphere. The PHA-stimulated PBMCs are adjusted at a concentration of 5×10$^6$/mL and then infected with HIV-1$_{111B}$ at a MOI of 5.0 for 3 hours at 37° C. in a humidified 5% CO$_2$ atmosphere and then washed to remove any residual virus. Thereafter, cells are resuspended in culture medium supplemented with interleukin-2 (IL-2) at a concentration of 50 units/mL (2×) and seeded at a density of 0.2×10$^6$ cells/well into 96-well plates in the absence or presence of various concentrations of the test compound. Then, infected-cells are cultured for 4 days at 37° C. in a humidified 5% CO$_2$ atmosphere in the absence or presence of 30% human serum after which an aliquot of cultured medium supernatant is replaced with fresh medium supplemented with human serum (when necessary) containing the serially diluted test compound. The IC$_{50}$ and IC$_{90}$ values for the virus replication are determined at day 6 post-infection by measuring the reverse transcriptase activity in the harvested supernatant by using GRAPHPAD PRISM software.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

We claim:

1. A compound of formula (I) or a pharmaceutically acceptable salt thereof:

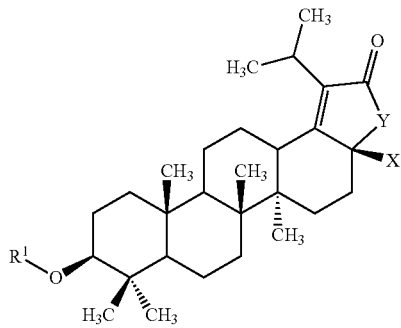

(I)

wherein
R$^1$ is

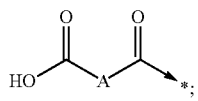

A is C$_{1-8}$ alkyl, C$_{2-8}$ alkenyl, or —(CH$_2$)$_{1-2}$O(CH$_2$)$_{1-2}$—;
Y is C═O or C—R$_{y1}$R$_{y2}$;
R$_{y1}$ and R$_{y2}$ are each independently H or —CH$_3$;
X is

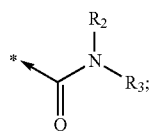

R$_2$ is H, C$_{1-12}$ alkyl which is unsubstituted or substituted one or more times by R$^{10}$, C$_{2-12}$ alkenyl which is unsubstituted or substituted one or more times by R$^{10}$, or C$_{2-12}$ alkynyl which is unsubstituted or substituted one or more times by R$^{10}$;
R$_3$ is H, C$_{1-12}$ alkyl which is unsubstituted or substituted one or more times by R$^{10}$, C$_{2-12}$ alkenyl which is unsubstituted or substituted one or more times by R$^{10}$, C$_{2-12}$ alkynyl which is unsubstituted or substituted one or more times by R$^{10}$, C$_{6-14}$ aryl which is unsubstituted or substituted one or more times by R$^{11}$, C$_{7-16}$ aralkyl which is unsubstituted or substituted one or more times by R$^{11}$, 5-12 member heteroaryl which is unsubstituted or substituted one or more times by R$^{11}$, 6-18 member heteroaralkyl which is unsubstituted or substituted one or more times by R$^{11}$, 3-12 member heterocycle which is unsubstituted or substituted one or more times by R$^{12}$, or 4-18 member heterocycle-alkyl which is unsubstituted or substituted one or more times by R$^{12}$;
R$_2$ and R$_3$ can also be taken together to form 5-12 member heteroaryl which is unsubstituted or substituted one or more times by R$^{11}$, or a 3-12 member heterocycle which is unsubstituted or substituted one or more times by R$^{12}$;
R$^{10}$ is halogen, oxo, C$_{1-6}$ alkoxy, —NH$_2$, —NH(C$_{1-4}$ alkyl), —N(C$_{1-4}$ alkyl)$_2$, —C(O)NH$_2$, —C(O)NH(C$_{1-4}$ alkyl), —C(O)N(C$_{1-4}$ alkyl)$_2$, —NHC(O)H, —N(C$_{1-4}$ alkyl)C(O)H, —N(C$_{1-4}$ alkyl)C(O)C$_{1-4}$ alkyl, —NHC(O)C$_{1-4}$ alkyl, —NHC(O)OC$_{1-4}$ alkyl, —N(C$_{1-4}$ alkyl)C(O)OC$_{1-4}$ alkyl, —NHC(O)NH$_2$, —N(C$_{1-4}$ alkyl)C(O)NH$_2$, —NHC(O)NHC$_{1-4}$ alkyl, —N(C$_{1-4}$ alkyl)C(O)

NHC$_{1-4}$ alkyl, —N(C$_{1-4}$ alkyl)C(O)N(C$_{1-4}$ alkyl)$_2$, —NHC(O)N(C$_{1-4}$ alkyl)$_2$, —C(O)H, —C(O)C$_{1-4}$ alkyl, C(O)OH, —C(O)OC$_{1-4}$ alkyl, —OC(O)C$_{1-4}$ alkyl, —OC(O)NH(C$_{1-4}$ alkyl), —OC(O)N(C$_{1-4}$ alkyl)$_2$, —C(NOH)C$_{1-4}$ alkyl, —C(NOH)H, —C(NOC$_{1-4}$ alkyl) C$_{1-4}$ alkyl, —C(NOC$_{1-4}$ alkyl)H, hydroxyl, nitro, azido, cyano, —S(O)$_{0-3}$H, —S(O)$_{0-3}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, —P(O)(OH)$_2$, —P(O)(OC$_{1-4}$alkyl)OH, —P(O)(OC$_{1-4}$alkyl)$_2$, amidino, or guanidino;

R$^{11}$ is halogen, C$_{1-6}$ alkyl, halogenated C$_{1-6}$ alkyl, C$_{2-6}$ alkenyl, C$_{2-6}$ alkynyl, C$_{1-6}$ alkoxy, —NH$_2$, —NH(C$_{1-4}$ alkyl), —N(C$_{1-4}$ alkyl)$_2$, —C(O)NH$_2$, —C(O)NH(C$_{1-4}$ alkyl), —C(O)N(C$_{1-4}$ alkyl)$_2$, —NHC(O)H, —N(C$_{1-4}$ alkyl)C(O)H, —N(C$_{1-4}$ alkyl)C(O)C$_{1-4}$ alkyl, —NHC(O)C$_{1-4}$ alkyl, —NHC(O)OC$_{1-4}$ alkyl, —N(C$_{1-4}$ alkyl)C(O)OC$_{1-4}$ alkyl, —NHC(O)NH$_2$, —N(C$_{1-4}$ alkyl)C(O)NH$_2$, —NHC(O)NHC$_{1-4}$ alkyl, —N(C$_{1-4}$ alkyl)C(O) NHC$_{1-4}$ alkyl, —N(C$_{1-4}$ alkyl)C(O)N(C$_{1-4}$ alkyl)$_2$, —NHC(O)N(C$_{1-4}$ alkyl)$_2$, —C(O)H, —C(O)C$_{1-4}$ alkyl, C(O)OH, —C(O)OC$_{1-4}$ alkyl, —OC(O)C$_{1-4}$ alkyl, —OC(O)NH(C$_{1-4}$ alkyl), —OC(O)N(C$_{1-4}$ alkyl)$_2$, —C(NOH)C$_{1-4}$ alkyl, —C(NOH)H, —C(NOC$_{1-4}$ alkyl) C$_{1-4}$ alkyl, —C(NOC$_{1-4}$ alkyl)H, hydroxyl, nitro, azido, cyano, —S(O)$_{0-3}$H, —S(O)$_{0-3}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, —P(O)(OH)$_2$, —P(O)(OC$_{1-4}$alkyl)OH, —P(O)(OC$_{1-4}$alkyl)$_2$, amidino, or guanidino; and R$^{12}$ is halogen, oxo, C$_{1-6}$ alkyl, halogenated C$_{1-6}$ alkyl, C$_{2-6}$ alkenyl, C$_{2-6}$ alkynyl, C$_{1-6}$ alkoxy, —NH$_2$, —NH(C$_{1-4}$ alkyl), —N(C$_{1-4}$ alkyl)$_2$, —C(O)NH$_2$, —C(O)NH(C$_{1-4}$ alkyl), —C(O)N(C$_{1-4}$ alkyl)$_2$, —NHC(O)H, —N(C$_{1-4}$ alkyl)C(O)H, —N(C$_{1-4}$ alkyl)C(O)C$_{1-4}$ alkyl, —NHC(O)C$_{1-4}$ alkyl, —NHC(O)OC$_{1-4}$ alkyl, —N(C$_{1-4}$ alkyl)C(O)OC$_{1-4}$ alkyl, —NHC(O)NH$_2$, —N(C$_{1-4}$ alkyl)C(O)NH$_2$, —NHC(O)NHC$_{1-4}$ alkyl, —N(C$_{1-4}$ alkyl)C(O)NHC$_{1-4}$ alkyl, —N(C$_{1-4}$ alkyl)C(O)N(C$_{1-4}$ alkyl)$_2$, —NHC(O)N(C$_{1-4}$ alkyl)$_2$, —C(O)H, —C(O)C$_{1-4}$ alkyl, C(O)OH, —C(O)OC$_{1-4}$ alkyl, —OC(O)C$_{1-4}$ alkyl, —OC(O)NH(C$_{1-4}$ alkyl), —OC(O)N(C$_{1-4}$ alkyl)$_2$, —C(NOH)C$_{1-4}$ alkyl, —C(NOH)H, —C(NOC$_{1-4}$ alkyl) C$_{1-4}$ alkyl, —C(NOC$_{1-4}$ alkyl)H, hydroxyl, nitro, azido, cyano, —S(O)$_{0-3}$H, —S(O)$_{0-3}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, —P(O)(OH)$_2$, —P(O)(OC$_{1-4}$alkyl)OH, —P(O)(OC$_{1-4}$alkyl)$_2$, amidino, or guanidino.

2. A compound according to claim 1, wherein Y is C—R$_{y1}$R$_{y2}$ and R$_{y1}$ and R$_{y2}$ are H.

3. A compound according to claim 2, wherein R$_1$ is 3',3'-dimethylsuccinyl.

4. A compound as defined in claim 3, wherein R$_2$ is H.

5. A compound according to claim 3, wherein R$_2$ and R$_3$ taken together form a 5-6 member heteroaryl which is unsubstituted or substituted one or more times by R$^{11}$ or a 5-6 member heterocycle which is unsubstituted or substituted one or more times by R$^{12}$.

6. A compound according to claim 5, wherein R$_2$ and R$_3$ taken together form a piperidyl, a piperazinyl, or a morpholinyl which is unsubstituted or substituted one or more times by R$^{11}$.

7. A compound according to claim 3, wherein R$_2$ and R$_3$ taken together form a diazabicyclo[3.2.1]octane which is unsubstituted or substituted one or more times by R$^{11}$.

8. A compound according to claim 4, wherein R$_3$ is pyrimidinyl which is unsubstituted or substituted one or more times by R$^{11}$.

9. A compound according to claim 4, wherein R$_3$ is pyrimidinyl.

10. A compound according to claim 4, wherein R$_3$ is pyridine which is unsubstituted or substituted one or more times by R$^{11}$.

11. A compound according to claim 4, wherein R$_3$ is pyridine.

12. A compound according to claim 4, wherein R$_3$ is pyrazole which is unsubstituted or substituted one or more times by R$^{11}$.

13. A compound according to claim 4, wherein R$_3$ is methylpyrazole.

14. A compound according to claim 1, wherein
R$^{10}$ is halogen, oxo, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —N(C$_{1-4}$ alkyl)COC$_{1-4}$ alkyl, —NHCOC$_{1-4}$ alkyl, carboxy, —C(O)OC$_{1-4}$ alkyl, hydroxyl, C$_{1-4}$ alkoxy, or cyano;
R$^{11}$ is halogen, C$_{1-6}$ alkyl, halogenated C$_{1-6}$ alkyl, C$_{2-6}$ alkenyl, C$_{2-6}$ alkynyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —N(C$_{1-4}$ alkyl)COC$_{1-4}$ alkyl, —NHCOC$_{1-4}$ alkyl, carboxy, —C(O)OC$_{1-4}$ alkyl, hydroxyl, or C$_{1-6}$ alkoxy; and
R$^{12}$ is halogen, oxo, C$_{1-6}$ alkyl, halogenated C$_{1-6}$ alkyl, —NH$_2$, —NH(C$_{1-4}$ alkyl), —N(C$_{1-4}$ alkyl)$_2$, —CONH$_2$, —CONH(C$_{1-4}$ alkyl), —CON(C$_{1-4}$ alkyl)$_2$, —N(C$_{1-4}$ alkyl)COC$_{1-4}$ alkyl, —NHCOC$_{1-4}$ alkyl, carboxy, —C(O)OC$_{1-4}$ alkyl, hydroxyl, or C$_{1-6}$ alkoxy.

15. A compound according to claim 1, wherein said compound is selected from:
3β-O-(3',3'-Dimethylsuccinyl)-21-oxolup-18-en-28-oic acid N-benzylamide;
3β-O-(3',3'-Dimethylsuccinyl)-21-oxolup-18-en-28-oic acid N-methylamide;
3β-O-(3',3'-Dimethylsuccinyl)-21-oxolup-18-en-28-oic acid N-isopropylamide;
3β-O-(3',3'-Dimethylsuccinyl)-21-oxolup-18-en-28-oic acid N-cyclohexylamide;
3β-O-(3',3'-Dimethylsuccinyl)-21-oxolup-18-en-28-oic acid N-cyclohexyl methylamide;
3β-O-(3',3'-Dimethylsuccinyl)-21-oxolup-18-en-28-oic acid N-piperidinyl acetamide;
3β-O-(3',3'-Dimethylsuccinyl)-21-oxolup-18-en-28-oic acid N-morpholyl acetamide;
3β-O-(3',3'-Dimethylsuccinyl)-21-oxolup-18-en-28-oic acid N-(4-acetyl piperazinyl)acetamide;
3β-O-(3',3'-Dimethylsuccinyl)-21-oxolup-18-en-28-oic acid N-(4-methyl piperazinyl)acetamide;
3β-O-(3',3'-Dimethylsuccinyl)-21-oxolup-18-en-28-oic acid N-benzamide;
3β-O-(3',3'-Dimethylsuccinyl)-21-oxolup-18-en-28-oic acid N-methyl-N-benzylamide;
3β-O-(3',3'-Dimethylsuccinyl)-21-oxolup-18-en-28-oic acid N-2-chloro-benzylamide;
3β-O-(3',3'-Dimethylsuccinyl)-21-oxolup-18-en-28-oic acid N-3-chloro-benzylamide;
3β-O-(3',3'-Dimethylsuccinyl)-21-oxolup-18-en-28-oic acid N-4-chloro-benzylamide;
3β-O-(3',3'-Dimethylsuccinyl)-21-oxolup-18-en-28-oic acid N-4-methoxy-benzylamide;
3β-O-(3',3'-Dimethylsuccinyl)-21-oxolup-18-en-28-oic acid N-pyridin-2-ylmethylamide;

3β-O-(3',3'-Dimethylsuccinyl)-21-oxolup-18-en-28-oic acid N-pyridin-3-ylmethylamide;
3β-O-(3',3'-Dimethylsuccinyl)-21-oxolup-18-en-28-oic acid N-pyridin-4-ylmethylamide;
3β-O-(3',3'-Dimethylsuccinyl)-21-oxolup-18-en-28-oic acid N-[2-(4-methoxy-phenyl)-ethy]-acetamide;
3β-O-(3',3'-Dimethylsuccinyl)-21-oxolup-18-en-28-oic acid N-(2-acetylamino-ethyl)-carbamic acid tert-butyl ester;
3β-O-(3',3'-Dimethylsuccinyl)-21-oxolup-18-en-28-oic acid N-(2-amino-ethyl)-acetamide;
3β-O-(3',3'-Dimethylsuccinyl)-21-oxolup-18-en-28-oic acid N-(2-acetylamino-ethyl)-acetamide;
3β-O-(3',3'-Dimethylsuccinyl)-21-oxolup-18-en-28-oic acid N-[2-(3-isopropyl-ureido)-ethy]-acetamide;
3β-O-(3',3'-Dimethylsuccinyl)-21-oxolup-18-en-28-oic acid N-(2-acetylamino-ethyl)-carbamic acid methyl ester;
3β-O-(3',3'-Dimethylsuccinyl)-21-oxolup-18-en-28-oic acid N-pyridin-2-yl-acetamide;
3β-O-(3',3'-Dimethylsuccinyl)-21-oxolup-18-en-28-oic acid N-pyridin-3-yl-acetamide;
3β-O-(3',3'-Dimethylsuccinyl)-21-oxolup-18-en-28-oic acid N-1-acetyl-piperazine-4-carboxylic acid tert-butyl ester;
3β-O-(3',3'-Dimethylsuccinyl)-21-oxolup-18-en-28-oic acid N-piperazinyl-acetamide;
3β-O-(3',3'-Dimethylsuccinyl)-21-oxolup-18-en-28-oic acid N-1-(4-hydroxy-piperidin-1-yl)-acetamide;
3β-O-(3',3'-Dimethylsuccinyl)-21-oxolup-18-en-28-oic acid N-1-acetylamino-piperidine-4-carboxylic acid tert-butyl ester;
3β-O-(3',3'-Dimethylsuccinyl)-21-oxolup-18-en-28-oic acid N-(4-aminopiperidine)-acetamide;
3β-O-(3',3'-Dimethylsuccinyl)-21-oxolup-18-en-28-oic acid N-(4-amino-N-1-acetyl-piperidine)-acetamide;
3β-O-(3',3'-Dimethylsuccinyl)-21-oxolup-18-en-28-oic acid N-(1-phenyl-ethyl)-acetamide;
3β-O-(3',3'-Dimethylsuccinyl)-21-oxolup-18-en-28-oic acid N-(1-methyl-1-phenyl-ethyl)-acetamide;
3β-O-(3',3'-Dimethylsuccinyl)-21-oxolup-18-en-28-oic acid N-(tert-butyl)-acetamide;
3β-O-(3',3'-Dimethylsuccinyl)-21-oxolup-18-en-28-oic acid N-(8-amino-3,8-diaza-bicyclo[3.2.1]octane-3-benzamide)-acetamide;
3β-O-(3',3'-Dimethylsuccinyl)-21-oxolup-18-en-28-oic acid N-4-piperazi-2-one acetamide;
3β-O-(3',3'-Dimethylsuccinyl)-21-oxolup-18-en-28-oic acid N-pyrimidin-2-yl-acetamide;
3β-O-(3',3'-Dimethylsuccinyl)-21-oxolup-18-en-28-oic acid N-(4-N'-isopropylureido-1-piperazine)-acetamide;
3β-O-(3',3'-Dimethylsuccinyl)-21-oxolup-18-en-28-oic acid N-1-acetyl-piperazine-4-carboxylic acid methyl ester;
3β-O-(3',3'-Dimethylsuccinyl)-21-oxolup-18-en-28-oic acid N-(4-amino carboxylic acid tert-butyl-ester-1-piperidine)-acetamide;
3β-O-(3',3'-Dimethylsuccinyl)-21-oxolup-18-en-28-oic acid N-(4-amino-1-piperidine)-acetamide;
3β-O-(3',3'-Dimethylsuccinyl)-21-oxolup-18-en-28-oic acid N-(4-acetylamino-1-piperidine)-acetamide;
3β-O-(3',3'-Dimethylsuccinyl)-21-oxolup-18-en-28-oic acid N-[(4-amino-N'-isopropylureido)-1-piperidine]-acetamide;
3β-O-(3',3'-Dimethylsuccinyl)-21-oxolup-18-en-28-oic acid N-(4-amino carboxylic acid methyl ester-1-piperidine)-acetamide;
3β-O-(3',3'-Dimethylsuccinyl)-21-oxolup-18-en-28-oic acid N-4-(1-methyl-piperazi-2-one)-acetamide;
3β-O-(3',3'-Dimethylsuccinyl)-21-oxolup-18-en-28-oic acid N-2-methyl-phen-1-yl acetamide;
3β-O-(3',3'-Dimethylsuccinyl)-21-oxolup-18-en-28-oic acid N-3-methyl-phen-1-yl acetamide;
3β-O-(3',3'-Dimethylsuccinyl)-21-oxolup-18-en-28-oic acid N-4-methyl-phen-1-yl acetamide;
3β-O-(3',3'-Dimethylsuccinyl)-21-oxolup-18-en-28-oic acid N-8-acetylamino-3,8-diaza-bicyclo[3.2.1]octane-3-carboxylic acid tert-butyl ester;
3β-O-(3',3'-Dimethylsuccinyl)-21-oxolup-18-en-28-oic acid N-pyrimidin-5-yl-acetamide;
3β-O-(3',3'-Dimethylsuccinyl)-21-oxolup-18-en-28-oic acid N-pyridin-4-yl-acetamide;
3β-O-(3',3'-Dimethylsuccinyl)-21-oxolup-18-en-28-oic acid N-3-amino-1-methyl-1H-pyrazole-acetamide;
3β-O-(3',3'-Dimethylsuccinyl)-21-oxolup-18-en-28-oic acid N-5-amino-1-methyl-1H-pyrazole acetamide;
3β-O-(3',3'-Dimethylsuccinyl)-21-oxolup-18-en-28-oic acid N-4-methyl-pyrimidin-5-yl-acetamide;
3β-O-(3',3'-Dimethylsuccinyl)-21-oxolup-18-en-28-oic acid N-4-methyl-pyrimidin-2-yl-acetamide;
3β-O-(3',3'-Dimethylsuccinyl)-21-oxolup-18-en-28-oic acid N-4-amino-1-methyl-1H-pyrazole acetamide;
3β-O-(3',3'-Dimethylsuccinyl)-21-oxolup-18-en-28-oic acid N-4,6-dimethyl-pyrimidin-2-yl-acetamide;
3β-O-(3',3'-Dimethylsuccinyl)-21-oxolup-18-en-28-oic acid N-pyrazin-2-yl-acetamide;
3β-O-(3',3'-Dimethylsuccinyl)-21-oxolup-18-en-28-oic acid N-quinolin-3-yl-acetamide;
3β-O-(3',3'-Dimethylsuccinyl)-21-oxolup-18-en-28-oic acid N-(2-pyrrolidin-1-yl-ethyl)-acetamide;
3β-O-(3',3'-Dimethylsuccinyl)-21-oxolup-18-en-28-oic acid N-(5-methyl-[1,3,4]oxadiazol-2-yl)-acetamide;
3β-O-(3',3'-Dimethylsuccinyl)-21-oxolup-18-en-28-oic acid N-isoquinolin-4-yl-acetamide;
3β-O-(3',3'-Dimethylsuccinyl)-21-oxolup-18-en-28-oic acid N-pyrimidin-4-yl-acetamide;
3β-O-(3',3'-Dimethylsuccinyl)-21-oxolup-18-en-28-oic acid N-2-trifluoromethyl-phen-1-yl acetamide;
3β-O-(3',3'-Dimethylsuccinyl)-21-oxolup-18-en-28-oic acid N-(1-methyl-1H-tetrazol-5-yl)-acetamide;
3β-O-(3',3'-Dimethylsuccinyl)-21-oxolup-18-en-28-oic acid N-(4-amino carboxylic acid ethyl ester-1-piperidine)-acetamide;
3β-O-(3',3'-Dimethylsuccinyl)-21-oxolup-18-en-28-oic acid N-(4-amino carboxylic acid isopropyl ester-1-piperidine)-acetamide;
3β-O-(3',3'-Dimethylsuccinyl)-21-oxolup-18-en-28-oic acid N-cyclopropylmethyl acetamide;
3β-O-(3',3'-Dimethylsuccinyl)-21-oxolup-18-en-28-oic acid N-azetidine-1 acetamide;
3β-O-(3',3'-Dimethylsuccinyl)-21-oxolup-18-en-28-oic acid N-(2,2,2-trifluoro-ethyl)-acetamide;
3β-O-(3',3'-Dimethylsuccinyl)-21-oxolup-18-en-28-oic acid N-4-trifluoro-pyrimidin-2-yl-acetamide;
3β-O-(3',3'-Dimethylsuccinyl)-21-oxolup-18-en-28-oic acid N-(1-cyclopropyl-1-methyl-ethyl)-acetamide;
3β-O-(3',3'-Dimethylsuccinyl)-21-oxolup-18-en-28-oic acid N-(4-dimethylamino-piperidin-1-yl)-acetamide;
3β-O-(3',3'-Dimethylsuccinyl)-21-oxolup-18-en-28-oic acid N-(2,2,2-trifluoro-1-methyl-ethyl)-acetamide;
3β-O-(3',3'-Dimethylsuccinyl)-21-oxolup-18-en-28-oic acid N-(5-methyl-[1,3,4]thiadiazol-2-yl)-acetamide;
3β-O-(3',3'-Dimethylsuccinyl)-21-oxolup-18-en-28-oic acid N-(2,2,2-trifluoro-1,1-dimethyl-ethyl)-acetamide;

3β-O-(3',3'-Dimethylsuccinyl)-21-oxolup-18-en-28-oic acid N-tert-butyl-N-methyl-acetamide;
3β-O-(3',3'-Dimethylsuccinyl)-21-oxolup-18-en-28-oic acid N—(R)-2-acetylaminomethyl-pyrrolidine-1-carboxylic acid tert-butyl ester;
3β-O-(3',3'-Dimethylsuccinyl)-21-oxolup-18-en-28-oic acid N—(S)-2-acetylaminomethyl-pyrrolidine-1-carboxylic acid tert-butyl ester;
3β-O-(3',3'-Dimethylsuccinyl)-21-oxolup-18-en-28-oic acid N—((R)-1-pyrrolidin-2-ylmethyl)-acetamide;
3β-O-(3',3'-Dimethylsuccinyl)-21-oxolup-18-en-28-oic acid N—((S)-1-pyrrolidin-2-ylmethyl)-acetamide;
3β-O-(3',3'-Dimethylsuccinyl)-21-oxolup-18-en-28-oic acid N—((R)-1-methyl-pyrrolidin-2-ylmethyl)-acetamide;
3β-O-(3',3'-Dimethylsuccinyl)-21-oxolup-18-en-28-oic acid N—((S)-1-methyl-pyrrolidin-2-ylmethyl)-acetamide;
3β-O-(3',3'-Dimethylsuccinyl)-21-oxolup-18-en-28-oic acid N-(4,4-difluoro-cyclohexyl)acetamide;
3β-O-(3',3'-Dimethylsuccinyl)-21-oxolup-18-en-28-oic acid N-2-chloro-phen-1-yl acetamide;
3β-O-(3',3'-Dimethylsuccinyl)-21-oxolup-18-en-28-oic acid N-2-isopropyl-phen-1-yl acetamide;
3β-O-(3',3'-Dimethylsuccinyl)-21-oxolup-18-en-28-oic acid N-4-fluoro-phen-1-yl acetamide;
3β-O-(3',3'-Dimethylsuccinyl)-21-oxolup-18-en-28-oic acid N-quinazolin-2-yl acetamide;
3β-O-(3',3'-Dimethylsuccinyl)-21-oxolup-18-en-28-oic acid N-(1-methyl-1H-tetrazol-3-yl)-acetamide;
3β-O-(3',3'-Dimethylsuccinyl)-21-oxolup-18-en-28-oic acid N-(5-methyl-isoxazol-3-yl)-acetamide;
3β-O-(3',3'-Dimethylsuccinyl)-21-oxolup-18-en-28-oic acid N-(1,3-dihydro-isoindol-2-yl)-acetamide;
3β-O-(3',3'-Dimethylsuccinyl)-21-oxolup-18-en-28-oic acid N-(4,4-difluoro-cyclohexylmethyl)-acetamide;
3β-O-(3',3'-Dimethylsuccinyl)-21-oxolup-18-en-28-oic acid N-4,4-difluoro-piperidine acetamide;
3β-O-(3',3'-Dimethylsuccinyl)-21-oxolup-18-en-28-oic acid N-8-acetylamino-3,8-diaza-bicyclo[3.2.1]octane-3-acetamide; and
pharmaceutically acceptable salts thereof.

16. A compound according to claim 1, wherein said compound is selected from:
3β-O-(3',3'-Dimethylsuccinyl)-21-oxolup-18-en-28-oic acid N-piperazinyl-acetamide hydrochloride salt;
3β-O-(3',3'-Dimethylsuccinyl)-21-oxolup-18-en-28-oic acid N-(4-aminopiperidine)-acetamide hydrochloride salt;
3β-O-(3',3'-Dimethylsuccinyl)-21-oxolup-18-en-28-oic acid N-(2-amino-ethyl)-acetamide hydrochloride salt;
3β-O-(3',3'-Dimethylsuccinyl)-21-oxolup-18-en-28-oic acid N-5-amino-1-methyl-1H-pyrazole-acetamide hydrochloride salt;
3β-O-(3',3'-Dimethylsuccinyl)-21-oxolup-18-en-28-oic acid N-4-methyl-pyrimidin-5-yl-acetamide hydrochloride salt;
3β-O-(3',3'-Dimethylsuccinyl)-21-oxolup-18-en-28-oic acid N-4-methyl-pyrimidin-2-yl-acetamide hydrochloride salt;
3β-O-(3',3'-Dimethylsuccinyl)-21-oxolup-18-en-28-oic acid N-4-amino-1-methyl-1H-pyrazole-acetamide hydrochloride salt; and
3β-O-(3',3'-Dimethylsuccinyl)-21-oxolup-18-en-28-oic acid N-4,6-dimethyl-pyrimidin-2-yl-acetamide hydrochloride salt.

17. A compound according to claim 1, wherein said compound is selected from:
3β-O-(3',3'-Dimethylsuccinyl)-21-oxolup-18-en-28-oic acid N-benzylamide;
3β-O-(3',3'-Dimethylsuccinyl)-21-oxolup-18-en-28-oic acid N-piperidinyl acetamide;
3β-O-(3',3'-Dimethylsuccinyl)-21-oxolup-18-en-28-oic acid N-benzamide;
3β-O-(3',3'-Dimethylsuccinyl)-21-oxolup-18-en-28-oic acid N-1-acetylamino-piperidine-4-carboxylic acid tert-butyl ester;
3β-O-(3',3'-Dimethylsuccinyl)-21-oxolup-18-en-28-oic acid N-(8-amino-3,8-diaza-bicyclo[3.2.1]octane-3-benzamide)-acetamide;
3β-O-(3',3'-Dimethylsuccinyl)-21-oxolup-18-en-28-oic acid N-pyrimidin-2-yl-acetamide;
3β-O-(3',3'-Dimethylsuccinyl)-21-oxolup-18-en-28-oic acid N-1-acetyl-piperazine-4-carboxylic acid methyl ester;
3β-O-(3',3'-Dimethylsuccinyl)-21-oxolup-18-en-28-oic acid N-2-methyl-phen-1-yl acetamide;
3β-O-(3',3'-Dimethylsuccinyl)-21-oxolup-18-en-28-oic acid N-(2,2,2-trifluoro-1-methyl-ethyl)-acetamide;
3β-O-(3',3'-Dimethylsuccinyl)-21-oxolup-18-en-28-oic acid N-(4,4-difluoro-cyclohexylmethyl)-acetamide;
3β-O-(3',3'-Dimethylsuccinyl)-21-oxolup-18-en-28-oic acid N-4,4-difluoro-piperidine acetamide; and
pharmaceutically acceptable salts thereof.

18. A compound selected from:
3β-O-Acetoxy-21-oxolup-18-en-28-oic acid N-methylamide;
3β-O-Acetoxy-21-oxolup-18-en-28-oic acid N-isopropylamide;
3β-O-Acetoxy-21-oxolup-18-en-28-oic acid N-cyclohexylamide;
3β-O-Acetoxy-21-oxolup-18-en-28-oic acid N-cyclohexyl methylamide;
3β-O-Acetoxy-21-oxolup-18-en-28-oic acid N-piperidinyl acetamide;
3β-O-Acetoxy-21-oxolup-18-en-28-oic acid N-morpholyl acetamide;
3β-O-Acetoxy-21-oxolup-18-en-28-oic acid N-(4-acetyl piperazinyl) acetamide;
3β-O-Acetoxy-21-oxolup-18-en-28-oic acid N-(4-methyl piperazinyl) acetamide;
3β-O-Acetoxy-21-oxolup-18-en-28-oic acid N-benzamide;
3β-O-Acetoxy-21-oxolup-18-en-28-oic acid N-methyl-N-benzylamide;
3β-O-Acetoxy-21-oxolup-18-en-28-oic acid N-2-chloro-benzylamide;
3β-O-Acetoxy-21-oxolup-18-en-28-oic acid N-3-chloro-benzylamide;
3β-O-Acetoxy-21-oxolup-18-en-28-oic acid N-4-chloro-benzylamide;
3β-O-Acetoxy-21-oxolup-18-en-28-oic acid N-4-methoxy-benzylamide;
3β-O-Acetoxy-21-oxolup-18-en-28-oic acid N-pyridin-2-ylmethylamide;
3β-O-Acetoxy-21-oxolup-18-en-28-oic acid N-pyridin-3-ylmethylamide;
3β-O-Acetoxy-21-oxolup-18-en-28-oic acid N-pyridin-4-ylmethylamide;
3β-O-Acetoxy-21-oxolup-18-en-28-oic acid N-[2-(4-methoxy-phenyl)-ethyl]-acetamide;
3β-O-Acetoxy-21-oxolup-18-en-28-oic acid N-(2-acetylamino-ethyl)-carbamic acid tert-butyl ester;

3β-O-Acetoxy-21-oxolup-18-en-28-oic acid N-pyridin-2-yl-acetamide;
3β-O-Acetoxy-21-oxolup-18-en-28-oic acid N-pyridin-3-yl-acetamide;
3β-O-Acetoxy-21-oxolup-18-en-28-oic acid N-1-acetyl-piperazine-4-carboxylic acid tert-butyl ester;
3β-O-Acetoxy-21-oxolup-18-en-28-oic acid N-1-(4-tert-butyl-dimethyl-silanyloxy-piperidin-1-yl)-acetamide;
3β-O-Acetoxy-21-oxolup-18-en-28-oic acid N-1-acetylamino-piperidine-4-carboxylic acid tert-butyl ester;
3β-O-Acetoxy-21-oxolup-18-en-28-oic acid N-(1-phenyl-ethyl)-acetamide;
3β-O-Acetoxy-21-oxolup-18-en-28-oic acid N-(1-methyl-1-phenyl-ethyl)-acetamide;
3β-O-Acetoxy-21-oxolup-18-en-28-oic acid N-(tert-butyl)-acetamide;
3β-O-Acetoxy-21-oxolup-18-en-28-oic acid N-(8-amino-3,8-diaza-bicyclo[3.2.1]octane-3-benzamide)-acetamide;
3β-O-Acetoxy-21-oxolup-18-en-28-oic acid N-4-piperazi-2-one-acetamide;
3β-O-Acetoxy-21-oxolup-18-en-28-oic acid N-pyrimidin-2-yl-acetamide;
3β-O-Acetoxy-21-oxolup-18-en-28-oic acid N-(4-amino carboxylic acid tert-butyl-ester-1-piperidine)-acetamide;
3β-O-Acetoxy-21-oxolup-18-en-28-oic acid N-4-(1-methyl-piperazi-2-one)-acetamide;
3β-O-Acetoxy-21-oxolup-18-en-28-oic acid N-2-methyl-phen-1-yl acetamide;
3β-O-Acetoxy-21-oxolup-18-en-28-oic acid N-3-methyl-phen-1-yl acetamide;
3β-O-Acetoxy-21-oxolup-18-en-28-oic acid N-4-methyl-phen-1-yl acetamide;
3β-O-Acetoxy-21-oxolup-18-en-28-oic acid N-8-acetylamino-3,8-diaza-bicyclo[3.2.1]octane-3-carboxylic acid tert-butyl ester;
3β-O-Acetoxy-21-oxolup-18-en-28-oic acid N-pyrimidin-5-yl-acetamide;
3β-O-Acetoxy-21-oxolup-18-en-28-oic acid N-pyridin-4-yl-acetamide;
3β-O-Acetoxy-21-oxolup-18-en-28-oic acid N-3-amino-1-methyl-1H-pyrazole-acetamide;
3β-O-Acetoxy-21-oxolup-18-en-28-oic acid N-5-amino-1-methyl-1H-pyrazole-acetamide;
3β-O-Acetoxy-21-oxolup-18-en-28-oic acid N-4-methyl-pyrimidin-5-yl-acetamide;
3β-O-Acetoxy-21-oxolup-18-en-28-oic acid N-4-methyl-pyrimidin-2-yl-acetamide;
3β-O-Acetoxy-21-oxolup-18-en-28-oic acid N-4-amino-1-methyl-1H-pyrazole-acetamide;
3β-O-Acetoxy-21-oxolup-18-en-28-oic acid N-4,6-dimethyl-pyrimidin-2-yl-acetamide;
3β-O-Acetoxy-21-oxolup-18-en-28-oic acid N-pyrazin-2-yl-acetamide;
3β-O-Acetoxy-21-oxolup-18-en-28-oic acid N-quinolin-3-yl-acetamide;
3β-O-Acetoxy-21-oxolup-18-en-28-oic acid N-(2-pyrrolidin-1-yl-ethyl)-acetamide;
3β-O-Acetoxy-21-oxolup-18-en-28-oic acid N-(5-methyl-[1,3,4]oxadiazol-2-yl)-acetamide;
3β-O-Acetoxy-21-oxolup-18-en-28-oic acid N-isoquinolin-4-yl-acetamide;
3β-O-Acetoxy-21-oxolup-18-en-28-oic acid N-pyrimidin-4-yl-acetamide;
3β-O-Acetoxy-21-oxolup-18-en-28-oic acid N-2-trifluoromethyl-phen-1-yl acetamide;
3β-O-Acetoxy-21-oxolup-18-en-28-oic acid N-(1-methyl-1H-tetrazol-5-yl)-acetamide;
3β-O-Acetoxy-21-oxolup-18-en-28-oic acid N-cyclopropylmethyl acetamide;
3β-O-Acetoxy-21-oxolup-18-en-28-oic acid N-azetidine-1 acetamide;
3β-O-Acetoxy-21-oxolup-18-en-28-oic acid N-(2,2,2-trifluoro-ethyl)-acetamide;
3β-O-Acetoxy-21-oxolup-18-en-28-oic acid N-4-trifluoro-pyrimidin-2-yl-acetamide;
3β-O-Acetoxy-21-oxolup-18-en-28-oic acid N-(1-cyclopropyl-1-methyl-ethyl)-acetamide;
3β-O-Acetoxy-21-oxolup-18-en-28-oic acid N-(4-dimethylamino-piperidin-1-yl)-acetamide;
3β-O-Acetoxy-21-oxolup-18-en-28-oic acid N-(2,2,2-trifluor-1-methyl-ethyl)-acetamide;
3β-O-Acetoxy-21-oxolup-18-en-28-oic acid N-(5-methyl-[1,3,4]thiadiazol-2-yl)-acetamide;
3β-O-Acetoxy-21-oxolup-18-en-28-oic acid N(2,2,2-trifluoro-1,1-dimethyl-ethyl)-acetamide;
3β-O-Acetoxy-21-oxolup-18-en-28-oic acid N-tert-butyl-N-methyl-acetamide;
3β-O-Acetoxy-21-oxolup-18-en-28-oic acid N-(R)-2-acetylaminomethyl-pyrrolidine-1-carboxylic acid tert-butyl ester;
3β-O-Acetoxy-21-oxolup-18-en-28-oic acid N-(S)-2-acetylaminomethyl-pyrrolidine-1-carboxylic acid tert-butyl ester;
3β-O-Acetoxy-21-oxolup-18-en-28-oic acid N-(4,4-difluoro-cyclohexyl) acetamide;
3β-O-Acetoxy-21-oxolup-18-en-28-oic acid N-2-chloro-phen-1-yl acetamide;
3β-O-Acetoxy-21-oxolup-18-en-28-oic acid N-2-isopropyl-phen-1-yl acetamide;
3β-O-Acetoxy-21-oxolup-18-en-28-oic acid N-4-fluoro-phen-1-yl acetamide;
3β-O-Acetoxy-21-oxolup-18-en-28-oic acid N-quinazolin-2-yl acetamide;
3β-O-Acetoxy-21-oxolup-18-en-28-oic acid N-(1-methyl-1H-tetrazol-3-yl)-acetamide;
3β-O-Acetoxy-21-oxolup-18-en-28-oic acid N-(5-methyl-isoxazol-3-yl)-acetamide;
3β-O-Acetoxy-21-oxolup-18-en-28-oic acid N-(1,3-dihydro-isoindol-2-yl)-acetamide;
3β-O-Acetoxy-21-oxolup-18-en-28-oic acid N-(4,4-difluoro-cyclohexylmethyl)-acetamide;
3β-O-Acetoxy-21-oxolup-18-en-28-oic acid N-4,4-difluoro-piperidine acetamide;
and pharmaceutically acceptable salts thereof.

19. A compound selected from:
3β-O-Hydroxy-21-oxolup-18-en-28-oic acid N-methylamide;
3β-O-Hydroxy-21-oxolup-18-en-28-oic acid N-isopropylamide;
3β-O-Hydroxy-21-oxolup-18-en-28-oic acid N-cyclohexylamide;
3β-O-Hydroxy-21-oxolup-18-en-28-oic acid N-cyclohexyl methylamide;
3β-O-Hydroxy-21-oxolup-18-en-28-oic acid N-piperidinyl acetamide;
3β-O-Hydroxy-21-oxolup-18-en-28-oic acid N-morpholyl acetamide;
3β-O-Hydroxy-21-oxolup-18-en-28-oic acid N-(4-acetyl piperazinyl) acetamide;
3β-O-Hydroxy-21-oxolup-18-en-28-oic acid N-(4-methyl piperazinyl) acetamide;

3β-O-Hydroxy-21-oxolup-18-en-28-oic acid N-benzamide;
3β-O-Hydroxy-21-oxolup-18-en-28-oic acid N-methyl-N-benzylamide;
3β-O-Hydroxy-21-oxolup-18-en-28-oic acid N-2-chloro-benzylamide;
3β-O-Hydroxy-21-oxolup-18-en-28-oic acid N-3-chloro-benzylamide;
3β-O-Hydroxy-21-oxolup-18-en-28-oic acid N-4-chloro-benzylamide;
3β-O-Hydroxy-21-oxolup-18-en-28-oic acid N-4-methoxy-benzylamide;
3β-O-Hydroxy-21-oxolup-18-en-28-oic acid N-pyridin-2-ylmethylamide;
3β-O-Hydroxy-21-oxolup-18-en-28-oic acid N-pyridin-3-ylmethylamide;
3β-O-Hydroxy-21-oxolup-18-en-28-oic acid N-pyridin-4-ylmethylamide;
3β-O-Hydroxy-21-oxolup-18-en-28-oic acid N-[2-(4-methoxy-phenyl)-ethyl]-acetamide;
3β-O-Hydroxy-21-oxolup-18-en-28-oic acid N-(2-acetylamino-ethyl)-carbamic acid tert-butyl ester;
3β-O-Hydroxy-21-oxolup-18-en-28-oic acid N-pyridin-2-yl-acetamide;
3β-O-Hydroxy-21-oxolup-18-en-28-oic acid N-pyridin-3-yl-acetamide;
3β-O-Hydroxy-21-oxolup-18-en-28-oic acid N-1-acetyl-piperazine-4-carboxylic acid tert-butyl ester;
3β-O-Hydroxy-21-oxolup-18-en-28-oic acid N-1-(4-tert-butyl-dimethyl-silanyloxy-piperidin-1-yl)-acetamide;
3β-O-Hydroxy-21-oxolup-18-en-28-oic acid N-1-acetylamino-piperidine-4-carboxylic acid tert-butyl ester;
3β-O-Hydroxy-21-oxolup-18-en-28-oic acid N-(1-phenyl-ethyl)-acetamide;
3β-O-Hydroxy-21-oxolup-18-en-28-oic acid N-(1-methyl-1-phenyl-ethyl)-acetamide;
3β-O-Hydroxy-21-oxolup-18-en-28-oic acid N-(tert-butyl)-acetamide;
3β-O-Hydroxy-21-oxolup-18-en-28-oic acid N-(8-amino-3,8-diaza-bicyclo[3.2.1]octane-3-benzamide)-acetamide;
3β-O-Hydroxy-21-oxolup-18-en-28-oic acid N-4-piperazi-2-one-acetamide;
3β-O-Hydroxy-21-oxolup-18-en-28-oic acid N-pyrimidin-2-yl-acetamide;
3β-O-Hydroxy-21-oxolup-18-en-28-oic acid N-(4-amino carboxylic acid tert-butyl-ester-1-piperidine)-acetamide;
3β-O-Hydroxy-21-oxolup-18-en-28-oic acid N-4-(1-methyl-piperazi-2-one)-acetamide;
3β-O-Hydroxy-21-oxolup-18-en-28-oic acid N-2-methyl-phen-1-yl acetamide;
3β-O-Hydroxy-21-oxolup-18-en-28-oic acid N-3-methyl-phen-1-yl acetamide;
3β-O-Hydroxy-21-oxolup-18-en-28-oic acid N-4-methyl-phen-1 -yl acetamide;
3β-O-Hydroxy-21-oxolup-18-en-28-oic acid N-8-acetylamino-3,8-diaza-bicyclo[3.2.1]octane-3-carboxylic acid tert-butyl ester;
3β-O-Hydroxy-21-oxolup-18-en-28-oic acid N-pyrimidin-5-yl-acetamide;
3β-O-Hydroxy-21-oxolup-18-en-28-oic acid N-pyridin-4-yl-acetamide;
3β-O-Hydroxy-21-oxolup-18-en-28-oic acid N-3-amino-1-methyl-1H-pyrazole-acetamide;
3β-O-Hydroxy-21-oxolup-18-en-28-oic acid N-5-amino-1-methyl-1H-pyrazole-acetamide;
3β-O-Hydroxy-21-oxolup-18-en-28-oic acid N-4-methyl-pyrimidin-5-yl-acetamide;
3β-O-Hydroxy-21-oxolup-18-en-28-oic acid N-4-methyl-pyrimidin-2-yl-acetamide;
3β-O-Hydroxy-21-oxolup-18-en-28-oic acid N-4-amino-1-methyl-1H-pyrazole-acetamide;
3β-O-Hydroxy-21-oxolup-18-en-28-oic acid N-4,6-dimethyl-pyrimidin-2-yl-acetamide;
3β-O-Hydroxy-21-oxolup-18-en-28-oic acid N-pyrazin-2-yl-acetamide;
3β-O-Hydroxy-21-oxolup-18-en-28-oic acid N-quinolin-3-yl-acetamide;
3β-O-Hydroxy-21-oxolup-18-en-28-oic acid N-(2-pyrrolidin-1-yl-ethyl)-acetamide;
3β-O-Hydroxy-21-oxolup-18-en-28-oic acid N-(5-methyl-[1,3,4]oxadiazol-2-yl)-acetamide;
3β-O-Hydroxy-21-oxolup-18-en-28-oic acid N-isoquinolin-4-yl-acetamide;
3β-O-Hydroxy-21-oxolup-18-en-28-oic acid N-pyrimidin-4-yl-acetamide;
3β-O-Hydroxy-21-oxolup-18-en-28-oic acid N-2-trifluoromethyl-phen-1-yl acetamide;
3β-O-Hydroxy-21-oxolup-18-en-28-oic acid N-(1-methyl-1H-tetrazol-5-yl)-acetamide;
3β-O-Hydroxy-21-oxolup-18-en-28-oic acid N-cyclopropylmethyl acetamide;
3β-O-Hydroxy-21-oxolup-18-en-28-oic acid N-azetidine-1 acetamide;
3β-O-Hydroxy-21-oxolup-18-en-28-oic acid N-(2,2,2-trifluoro-ethyl)-acetamide;
3β-O-Hydroxy-21-oxolup-18-en-28-oic acid N-4-trifluoro-pyrimidin-2-yl-acetamide;
3β-O-Hydroxy-21-oxolup-18-en-28-oic acid N-(1-cyclopropyl-1-methyl-ethyl)-acetamide;
3β-O-Hydroxy-21-oxolup-18-en-28-oic acid N-(4-dimethylamino-piperidin-1-yl)-acetamide;
3β-O-Hydroxy-21-oxolup-18-en-28-oic acid N-(2,2,2-trifluor-1-methyl-ethyl)-acetamide;
3β-O-Hydroxy-21-oxolup-18-en-28-oic acid N-(5-methyl-[1,3,4]thiadiazol-2-yl)-acetamide;
3β-O-Hydroxy-21-oxolup-18-en-28-oic acid N(2,2,2-trifluoro-1,1-dimethyl-ethyl)-acetamide;
3β-O-Hydroxy-21-oxolup-18-en-28-oic acid N-tert-butyl-N-methyl-acetamide;
3β-O-Hydroxy-21-oxolup-18-en-28-oic acid N-(R)-2-acetylaminomethyl-pyrrolidine-1-carboxylic acid tert-butyl ester;
3β-O-Hydroxy-21-oxolup-18-en-28-oic acid N-(S)-2-acetylaminomethyl-pyrrolidine-1-carboxylic acid tert-butyl ester;
3β-O-Hydroxy-21-oxolup-18-en-28-oic acid N-(4,4-difluoro-cyclohexyl) acetamide;
3β-O-Hydroxy-21-oxolup-18-en-28-oic acid N-2-chloro-phen-1-yl acetamide;
3β-O-Hydroxy-21-oxolup-18-en-28-oic acid N-2-isopropyl-phen-1-yl acetamide;
3β-O-Hydroxy-21-oxolup-18-en-28-oic acid N-4-fluoro-phen-1-yl acetamide;
3β-O-Hydroxy-21-oxolup-18-en-28-oic acid N-quinazolin-2-yl acetamide;
3β-O-Hydroxy-21-oxolup-18-en-28-oic acid N-(1 -methyl-1H-tetrazol-3-yl)-acetamide;
3β-O-Hydroxy-21-oxolup-18-en-28-oic acid N-(5-methyhl-isoxazol-3-yl)-acetamide;
3β-O-Hydroxy-21-oxolup-18-en-28-oic acid N-(1,3-dihydro-isoindol-2-yl)-acetamide;

3β-O-Hydroxy-21-oxolup-18-en-28-oic acid N-(4,4-difluoro-cyclohexylmethyl)-acetamide;

3β-O-Hydroxy-21-oxolup-18-en-28-oic acid N-4,4-difluoro-piperidine acetamide;

and pharmaceutically acceptable salts thereof.

20. A pharmaceutical composition comprising a compound according to claim 1 together with one or more pharmaceutically acceptable carrier.

21. A method for the treatment of HIV infections in a subject in need of such treatment comprising administering to the subject a therapeutically effective amount of a compound according to claim 1.

* * * * *